United States Patent
Sanderford et al.

(10) Patent No.: US 11,961,049 B2
(45) Date of Patent: *Apr. 16, 2024

(54) SYSTEM AND METHOD FOR SCHEDULING PATIENT APPOINTMENTS

(71) Applicant: YIPS, LLC, Metairie, LA (US)

(72) Inventors: Shelby Sanderford, New Orleans, LA (US); Britton Sanderford, New Orleans, LA (US)

(73) Assignee: YIPS, LLC, Metairie, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/691,675

(22) Filed: Mar. 10, 2022

(65) Prior Publication Data

US 2022/0198402 A1     Jun. 23, 2022

Related U.S. Application Data

(63) Continuation of application No. 15/344,128, filed on Nov. 4, 2016, now Pat. No. 11,282,041.

(Continued)

(51) Int. Cl.
    *G06Q 10/1093*     (2023.01)
    *G16H 10/60*     (2018.01)

(52) U.S. Cl.
    CPC ......... *G06Q 10/1095* (2013.01); *G16H 10/60* (2018.01)

(58) Field of Classification Search
None
See application file for complete search history.

(56) References Cited

U.S. PATENT DOCUMENTS 8,688,466 B2 * 4/2014 Kharraz Tavakol ........................ G06Q 10/06311
                                                          705/2
2010/0217618 A1 * 8/2010 Piccirillo ............... G16H 40/20
                                                          705/2

(Continued)

FOREIGN PATENT DOCUMENTS

WO    WO-2014071023 A1 * 5/2014 ............... G06N 5/04

OTHER PUBLICATIONS

Qu, X. (2006). Development of appointment scheduling rules for open access scheduling (Order No. 3259977). Available from ProQuest Dissertations and Theses Professional. (305264123). (Year: 2006).*

*Primary Examiner* — Christopher L Gilligan
*Assistant Examiner* — Emily Huynh
(74) *Attorney, Agent, or Firm* — IP & T GROUP LLP

(57) ABSTRACT

A scheduling system and methods for scheduling patient appointments disclosed here utilize any available input to identify a timestamp and a spatial location related to a patient and/or one or more providers in proximity of one or more appointment locations, to allocate a set of procedure resources to each patient appointment based on the timestamps and the spatial locations, and to communicate any revised timing to the patient, thereby minimizing a total waiting time. The scheduling system allows for scheduling of appointments divided into multiple appointment states, each having a predicted timing. After a completed appointment state, individual uncertainty of the predicted timing is replaced with an actual timing and the predicted timing of the remaining schedule is revised. This scheduling system enables adaptive reallocation of resources while avoiding compounding the waiting times that create a multi-state iterative and time-variant problem.

17 Claims, 47 Drawing Sheets

Related U.S. Application Data

(60) Provisional application No. 62/250,929, filed on Nov. 4, 2015.

(56) References Cited

U.S. PATENT DOCUMENTS

| | | | | |
|---|---|---|---|---|
| 2014/0156302 | A1* | 6/2014 | Larsen | G16H 40/20 |
| | | | | 705/2 |
| 2014/0278535 | A1* | 9/2014 | Romeo | G06Q 10/087 |
| | | | | 705/3 |
| 2015/0081327 | A1* | 3/2015 | Mooker | G06Q 10/1095 |
| | | | | 705/2 |
| 2015/0118667 | A1* | 4/2015 | Andrew | G16H 40/63 |
| | | | | 434/236 |
| 2015/0213414 | A1* | 7/2015 | Zuckerman | G06Q 10/1095 |
| | | | | 705/7.19 |
| 2018/0150603 | A1* | 5/2018 | Bullington | G16H 40/20 |

\* cited by examiner

FIG. 2A

Ordered List 1110

| | | Appointment entry components 2000 | | | | | | |
|---|---|---|---|---|---|---|---|---|
| | | Appointment timing 2100 | | | Appointment Type 1133 | | | |
| | Patient ID 1120 | Estimated Appointment Time | Predetermined Appointment Duration (min) | Actual Appointment Duration (min) | | Appointment State(s) | Appointment Location(s) | Procedure Resources 3000 | Patient Status 2200 |
| patient appointment entries | John X. | 8:00 AM | 30 | 35 | First Visit | B[4] | | PR-B-1 | X,@ |
| | Bob Y. | 8:00 AM | 20 | 25 | X-Ray | C[7] | | PR-C-1 | X,@ |
| | Mark Z. | 8:00 AM | 45 | | Follow Up | A[3] | | PR-A-1 | ER3,@ |
| | Dave J. | 8:00 AM | 15 | | Consult | D[3] | | PR-D-1 | ER4,@ |
| | Beth K. | 8:15 AM | 15 | | Consult | D[1] | | PR-D-2 | WR,@ |
| | Mike G. | 8:45 AM | 30 | | First Visit | B[0] | | PR-B-2 | AWR,@ |
| | Shelby S. | 8:45 AM | 30 | | Follow Up | A[0] | | PR-A-2 | --- |
| | Buffer time / null name | | | | | | | | |

Appointment State Diagram A

Appointment State Diagram B

FIG. 2D

| Ordering | Appointment States For Appointment Type A | Appointment Location | PAD | Procedure Resources | Prediction Value(s) |
|---|---|---|---|---|---|
| 0 | Appointment Timing Assigned | | | | |
| 1 | Patient Check-in | | | | |
| 2 | Patient Vitals Taken | | | | |
| 3 | Provider Examination | | 15 min | | |
| 4 | Patient Check-out | | | | |

| Ordering | Appointment States For Appointment Type B | Appointment Location | PAD | Procedure Resources | Prediction Value(s) |
|---|---|---|---|---|---|
| 0 | Appointment Timing Assigned | | | | |
| 1 | Patient Check-in | | | | |
| 2 | Patient Vitals Taken | | | | |
| 3 | Provider Examination | | 10 min | | |
| 4 | Lab Test A | | | | |
| 5 | Provider Consultation | | 10 min | | |
| 6 | Patient Check-out | | | | |

| Ordering | Appointment States For Appointment Type C | Appointment Location | PAD | Procedure Resources | Prediction Value(s) |
|---|---|---|---|---|---|
| 0 | Appointment Timing Assigned | | | | |
| 1 | Patient Check-in | | | | |
| 2 | Patient Vitals Taken | | | | |
| 3 | Provider Examination | | 20 min | | |
| 4 | Lab Test B | | | | |
| 5 | X-Ray | | | | |
| 6 | Provider Consultation | | 20 min | | |
| 7 | Patient Check-out | | | | |

FIG. 2E

Short Ordered List appointment entry components 2000 patient appointment entries

| Patient ID 1120 | Estimated Appointment Time | Predetermined Appointment Duration (min) |
|---|---|---|
| John X. | 8:00 AM | 30 |
| Bob Y. | 8:00 AM | 20 |
| Mark Z. | 8:00 AM | 45 |
| Dave J. | 8:00 AM | 15 |
| Beth K. | 8:15 AM | 15 |
| Mike G. | 8:45 AM | 30 |
| Shelby S. | 8:45 AM | 30 |
| *Buffer time / null name* | | |

FIG. 3D

Patient Status 2200 including Patient State and Proximity-Time
List adaptively increases length as patient moves through office and rooms

| (Abb.) | Patient State 2210 | Patient Location 2220 | Actual Timestamp | Timer/ Duration |
|---|---|---|---|---|
| — | Not arrived, estimate time to arrival | @ | @ | @ |
| AWR | Approaching waiting room | @ | @ | @ |
| WR | In waiting room | @ | @ | @ |
| LWR | Leaving waiting room | @ | @ | @ |
| ER# | 'Registered' in Exam Room | @ | @ | @ |
| LER | Leaving Exam Room | @ | @ | @ |
| PR# | 'Registered' in Procedure Room | @ | @ | @ |
| LPR | Leaving Procedure Room | @ | @ | @ |
| X | Exited office | @ | @ | @ |

FIG. 3E

Methods & devices to establish a Proximity-Time

| State | Patient State 2210 | Methods & devices to establish Proximity-Time |
|---|---|---|
| — | Not arrived, estimate time to arrival | FIG 6 |
| AWR | Approaching waiting room | FIG 6, 7 |
| WR | In waiting room | FIG 6, 7, 10B, 9A, 9B, 11A |
| LWR | Leaving waiting room | FIG 6 |
| ER# | 'Registered' in Exam Room | FIG 6, 7, 9A, 9B, 10B, 11B, 11C |
| LER | Leaving Exam Room | FIG 6, 7, 11B, 11C |
| PR# | 'Registered' in Procedure Room | FIG 6, 11B |
| LPR | Leaving Procedure Room | FIG 6, 11B |
| X | Exited office | FIG 6, 7, 9A, 9B, 11A, 11B, 11C |

FIG. 9A
Provider Office Layout
(one level)
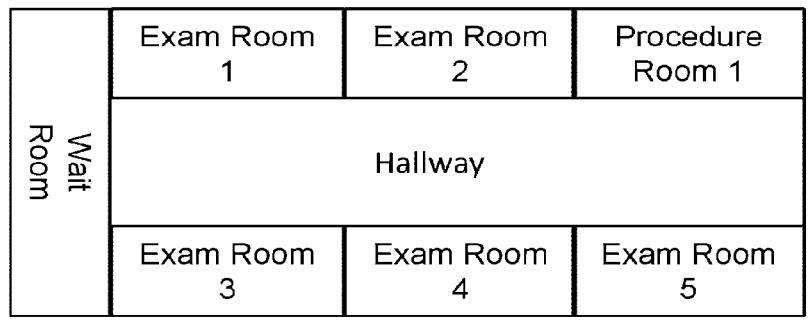
FIG. 9B
Provider Office Layout
(multiple levels)
Level 1
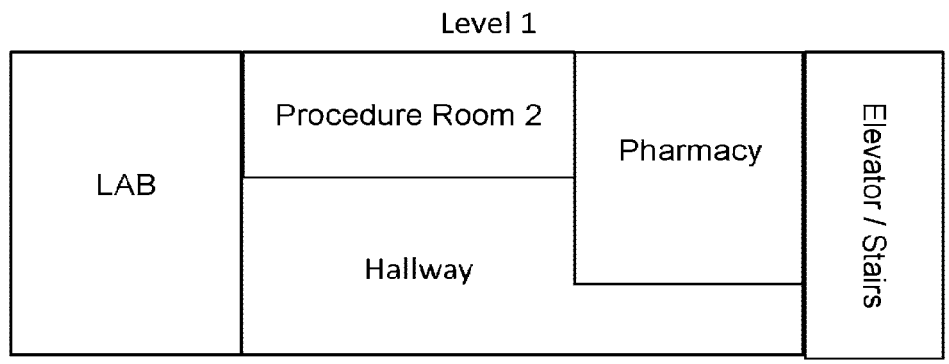
Level 2
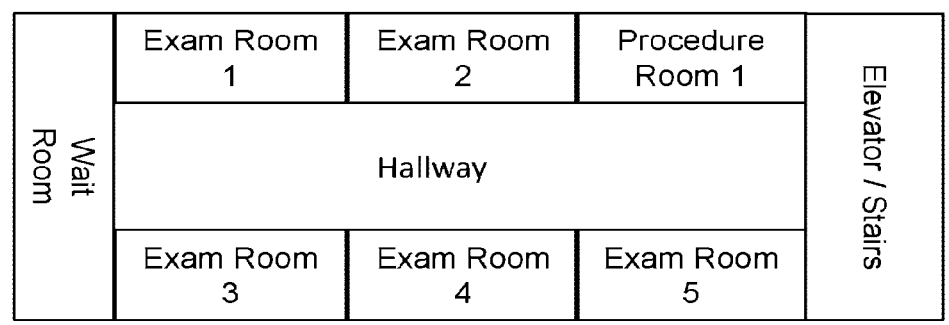

FIG. 13A
PROCEDURE RESOURCE ALLOCATION 3300
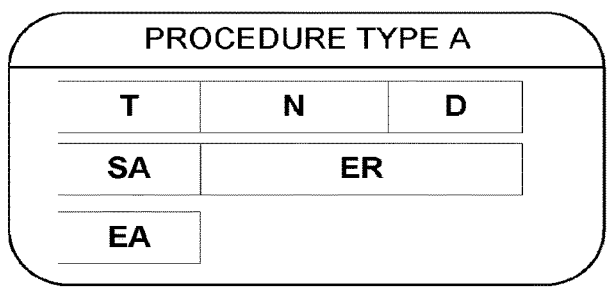
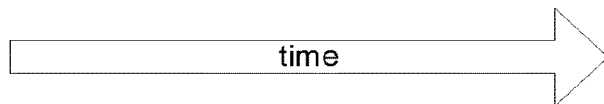
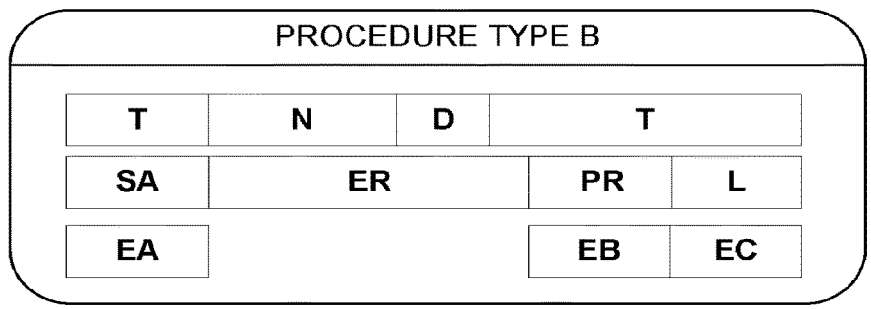
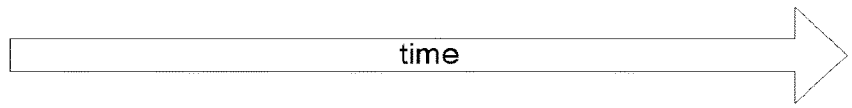
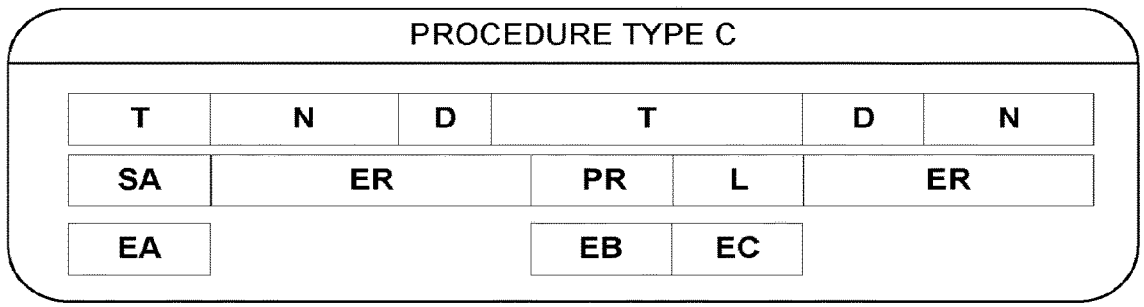
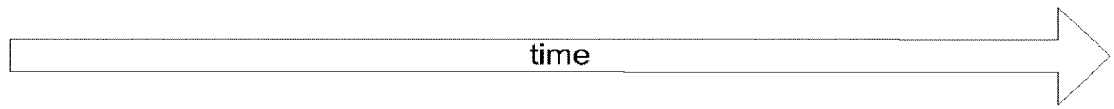

Bubble-up process on a procedure resource availability queue

"Lightest" procedure resource "bubble up" to top of the availability queue

FIG. 19

| KEY |
|---|
| X – ordered list or schedule database<br>pae – patient appointment entry<br>aTiming – appointment timing<br>aType – appointment type<br>aR – appointment resource<br>PS – patient status<br>PID – patient ID<br>P – prediction value<br>$Y_X$ – sensor system data<br>$Y_P$ – sensor system data spatial accuracy factor<br>$A_X$ – archive of patient appointment timing<br>$A_P$ – patient appointment entry component prediction value<br>$A_Y$ – archive of sensor system data spatial accuracy factors<br>$A_1$ – archive 1 ($A_X + A_P$)<br>$A_2$ – archive 2 ($A_1 + A_Y$) |

(1) $$X = \begin{bmatrix} x_{i,j} & \cdots & \square \\ \vdots & \ddots & \vdots \\ \square & \cdots & \square \end{bmatrix}$$

(2) $$x_{i,j} = [pae]$$

(3) $$pae_{i,j} = [appointment\ entry\ components]$$
$$pae_{i,j} = [PID \quad aTiming \quad aType \quad aR \quad PS]$$

(4) $$P = \begin{bmatrix} \square & \cdots & \square \\ \vdots & \ddots & \vdots \\ \square & \cdots & \square \end{bmatrix}$$

(5) $$Y = Y_X \times Y_P = \begin{bmatrix} \square & \cdots & \square \\ \vdots & \ddots & \vdots \\ \square & \cdots & \square \end{bmatrix}_{Y_X} \times \begin{bmatrix} \square & \cdots & \square \\ \vdots & \ddots & \vdots \\ \square & \cdots & \square \end{bmatrix}_{Y_P}$$

(6) $$A_1 = A_X \times A_P = \begin{bmatrix} \square & \cdots & \square \\ \vdots & \ddots & \vdots \\ \square & \cdots & \square \end{bmatrix}_{A_X} \times \begin{bmatrix} \square & \cdots & \square \\ \vdots & \ddots & \vdots \\ \square & \cdots & \square \end{bmatrix}_{A_P}$$

(7) $$A_2 = A_X \times A_P \times A_Y = \begin{bmatrix} \square & \cdots & \square \\ \vdots & \ddots & \vdots \\ \square & \cdots & \square \end{bmatrix}_{A_X} \times \begin{bmatrix} \square & \cdots & \square \\ \vdots & \ddots & \vdots \\ \square & \cdots & \square \end{bmatrix}_{A_P} \times \begin{bmatrix} \square & \cdots & \square \\ \vdots & \ddots & \vdots \\ \square & \cdots & \square \end{bmatrix}_{A_Y}$$

Method for initialization of new (future) day
when appointment type or medical need is unknown

SYSTEM AND METHOD FOR SCHEDULING PATIENT APPOINTMENTS

CROSS REFERENCES TO RELATED APPLICATIONS

This application claims priority from U.S. Ser. No. 15/344,128 filed on Nov. 4, 2016, which claims priority to U.S. Application No. 62/250,929, filed Nov. 4, 2015, the contents of each application are incorporated by reference in its entirety.

BACKGROUND

Accuracy of scheduling of medical appointments is poor, requiring patients to wait for care both prior to an appointment and within one or more appointment states that make up the appointment. A common wait time of 1-2 hours results in lost income and loss of productivity by the patient. Patient satisfaction is influenced by patient exasperation due to excessive total wait time. The total wait time also results in inefficiencies in use of resources. Each appointment state does not have a fixed and certain repeatable order and duration. In a medical appointment, a medical practitioner or provider is required to offer all reasonable care. A provider may not choose to abbreviate an examination by deciding to forgo a consultation, a test, or a medical procedure. Therefore, it is challenging for a clinical office to remain on schedule after a first few appointments have occurred in the day. Scheduling of numerous medical appointments without compounding delays remains a vexing challenge.

A typical doctor's office will attempt to schedule 20-60 appointments in a day. Some doctors allocate a same amount of time for each appointment and simply stop making appointments after 3:00 PM because they know this means the last patient will be seen at 5:30 PM. Some providers will try and divide appointments into two time durations based on whether the patient is new or an existing one, or they may divide the appointment into multiple time durations based on the medical need of the patient. After the first few patient appointments, each individual uncertainty of time duration accumulates. This accumulation becomes significant over a large number of individual appointments, essentially compounding the error in the prediction of the appointment timing 20 or 25 times. This is quite different than the error that can be accumulated by two table turns and corrected by an abbreviated coffee service.

There can be unscheduled emergency visits or regular visits that become emergencies. Further, a typical medical practitioner's office employs the use of more than one patient examination room. If a doctor's office has a typical number of four patient examination rooms, this means any one of those rooms can be in any aforementioned states, further adding to the complexity of prediction. A quick calculation of variability: Exam room states 3 to 5×0 to 2 loops×3 to 15 minutes per state lower bound 9 minutes upper bound 150 minutes (2.5 hours). If the mean duration of an examination or occupancy of an exam room is 45 minutes, and if the status quo can estimate visit duration with 20% accuracy then the 25th patient will have to wait nearly 2 hours before being cared for.

SUMMARY

A scheduling system and methods for scheduling patient appointments disclosed here utilize any available input to identify a timestamp and a spatial location relating to a patient and/or one or more providers in proximity of one or more appointment locations, to allocate a set of procedure resources to each patient appointment based on the timestamps and the spatial locations, and to communicate any revised timing to the patient, thereby minimizing a total waiting time. The scheduling system allows for scheduling of appointments divided into multiple appointment states, each having a predicted timing. An appointment start time is based on a sum of the predicted timing for each appointment state in the schedule. After a completed appointment state, individual uncertainty of the predicted timing is replaced with an actual timing and the predicted timing of the remaining schedule is revised. This scheduling system enables adaptive reallocation of resources while avoiding compounding the waiting times that create a multi-state iterative and time-variant problem.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 2A shows the ordered list shown in a table according to an example;

FIG. 2D shows an embodiment of the appointment state diagram, shown as a list and reflecting the one or more appointment states in a specific ordering according to an example;

FIG. 2E shows a shortened ordered list including a patient ID, an estimated appointment time, and a cumulative pre-determined appointment duration (PAD) for each patient appointment entry according to an example;

FIG. 3D shows the patient status as a growing list, where each entry includes a patient state, a patient location, an actual timestamp, and a respective timer or duration count depending on if the patient state is complete according to an example;

FIG. 3E shows examples of methods and devices to establish a proximity-time; according to an example;

FIG. 9A shows an example of a provider office layout with only one level according to an example;

FIG. 9B shows an example of a provider office layout with multiple levels according to an example;

FIG. 13A shows three examples of a set of procedure resource allocations for the procedure type;

FIG. 19 shows a data structure in the scheduling system according to an example;

DETAILED DESCRIPTION

Figure 1A:
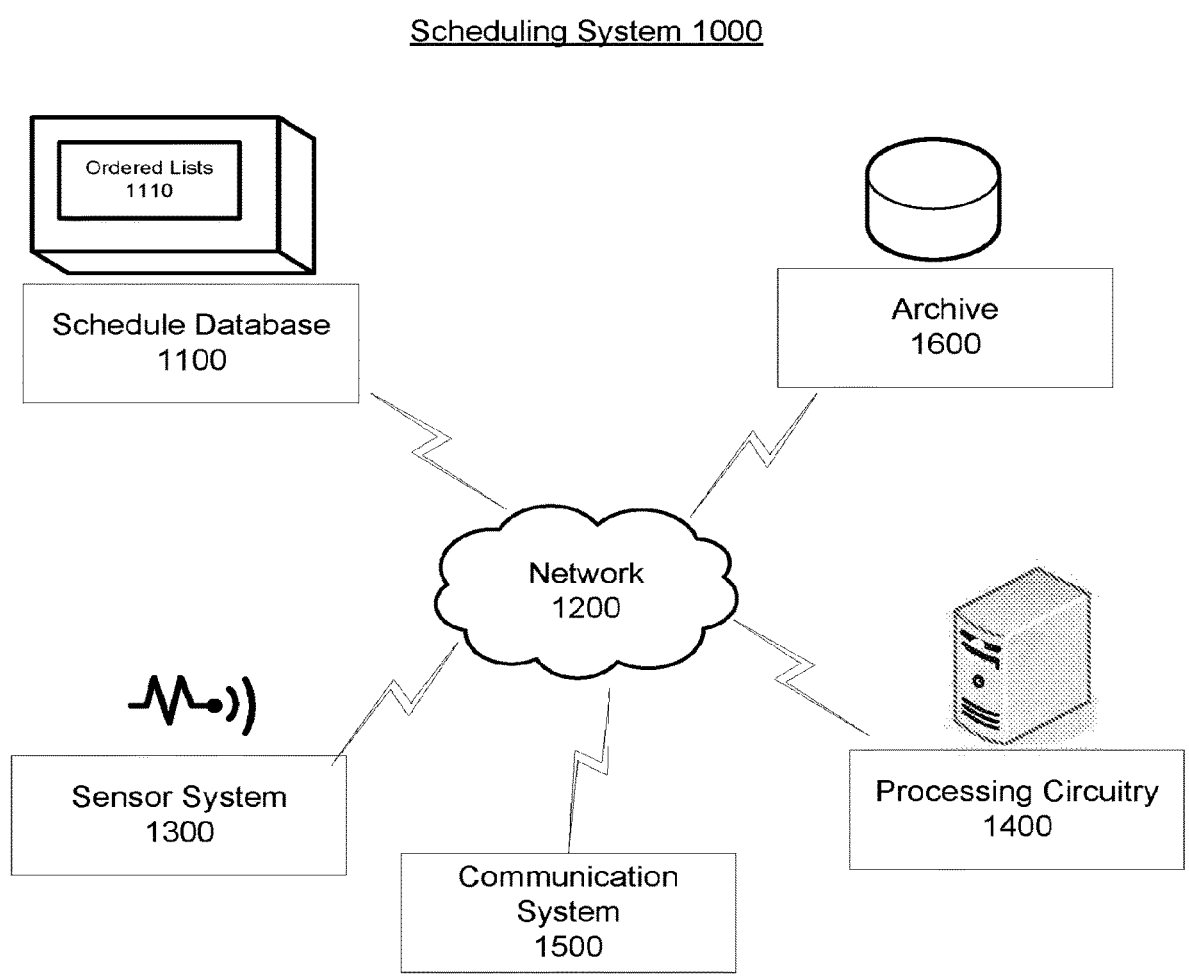
FIG. 1A shows a system for scheduling patient appointments or scheduling system including a network, a schedule database, an archive, one or more sensor systems, one or more communication systems, and processing circuitry according to an example.

A provider can be any healthcare servicer involved in providing patient care. Examples of providers include one or more doctors, physician assistants, physical therapists, chiropractors, nurses, technicians, social workers, clinical support helpers, and administrative support personnel. In some examples, the provider is anyone who uses a scheduling system for managing clinical appointments and/or the related billing for the appointment.

In some cases providers working full time will attempt to schedule tens of patient appointments or appointments in a day. Each appointment may have an appointment type and can be divided into different appointment states or phases each having uncertainty of time duration. After the first few appointments in a given day, the individual uncertainty of each appointment state time duration accumulates and affects the timing of other scheduled appointments. This accumulation becomes significant over the large number of appointments in the schedule. Once the patient leaves the waiting room and enters the exam room, the time durations becomes a multi-state iterative and time variant problem and generate a series of wait times in between each appointment state.

Each appointment state can have a highly variable time component depending upon numerous factors. For example, these factors can include whether the patient is a new or existing patient, elderly or disabled, male or female, overall health and fitness, a medical need, on timing of the test results, as well as the provider's experience with the medical need. Therefore, each appointment state may have unpredictable ordering, duration, and repetition.

Depending on the appointment type and their medical need, the patient may or may not be required to have medical procedures and tests performed throughout the appointment. In some cases the medical procedures and tests include lab testing, medical imaging, and other procedures requiring shared or scarce equipment that require the patient to wait in a queue or to be scheduled. The patient may travel to procedure rooms or equipment may be brought in to the exam room.

Once the patient is ready to be examined by the provider, they are expected to wait an indeterminate amount of time until the provider is available. The provider can be a scarce resource that divides their time amongst the other patients. In some cases, upon a physical examination or results of the medical procedures and tests, the provider can add additional testing and medical procedures, thereby repeating an appointment state and thereby extending the total appointment duration. Upon completion, the patient is then again directed to wait for the provider. As a repeat of an earlier state, the provider can make further deliberation leading to yet another repeated appointment state or upon the provider's satisfaction, a checkout process is initiated.

While this description is described for use in scheduling patient appointments, the systems and methods described here may be easily adapted for other fields such as scheduling appointments for beauty care such as hair salons, nail salons, massage salons, etc., as well as for automotive repairs. Scheduling systems for other fields may be able to improve accuracy of their timing by having sub-components with predictable, repeatable order, and duration. However, as explained, this is not the case for the scheduling of patient appointments. Furthermore, in some cases scheduling of patient appointments requires access to confidential, legally protected, and sensitive information spread among different providers and third party proprietary database systems. Also, private patient information is considered a unique data type that has specific laws regulating its access, storage, and transfer.

There are numerous benefits to addressing inaccuracy of the appointment timing for patient appointments. More accurate appointment timing may reduce the duration and frequency of the waiting times the patient experiences to receive care from the one or more providers. More accurate timing may also influence a patient's satisfaction, which ultimately can be reflected in a review of satisfaction attributed to the provider. In some cases, the satisfaction attributed to the provider is being factored in reimbursement methods, such as in the case of Medicare. Therefore, improving the patient's satisfaction can also affect the provider's financial success. More accurate timing may also allow for increased productivity of the patient in their own work by reducing time needed to take off work or other activities. Increased accuracy of timing may improve useful time of the provider and allow for better tracking of trends of availability to match with a patient's preferences.

This disclosure describes a scheduling system and a set of processes to predict appointment timing with increased accuracy resulting in reduced waiting time for each patient, irrespective of where they are on the schedule. An initial prediction of the appointment timing is done prior to the day of the scheduled appointment and a refined prediction of the appointment timing is calculated based on actual timing of events as they occur. A communication is sent to each patient to convey changes to their appointment timing to further reduce the patient's waiting time, by delaying their arrival. In one example, the scheduling system utilizes an application programming interface to securely access a variety of third party proprietary database systems, each requiring their own security handling of their data. The system and processes disclosed herein accommodate for the variety.

Referring now to the drawings, wherein like reference numerals designate identical or corresponding parts throughout the several views.

FIG. 1A

FIG. 1A shows a system for scheduling patient appointments or scheduling system 1000 according to an example. Here the scheduling system 1000 includes a network 1200 configured for communication between other scheduling system components including a schedule database 1100 for storing future patient appointment timing 2100, an archive 1600 for storing past patient appointment timing, one or more sensor systems 1300 for sensing proximity-time data from one or more communication systems 1500, and a processing circuitry 1400 for processing the proximity-time data and for communicating to the one or more communication systems 1500. The schedule database 1100 includes an ordered list 1110 for maintaining order of the appointment timing 2100 for the one or more patient appointments or appointments in a given day. According to an example, the functions of the processing circuitry 1400 can be distributed among different hardware and software.

FIGS. 1B-1C

Figure 1B:
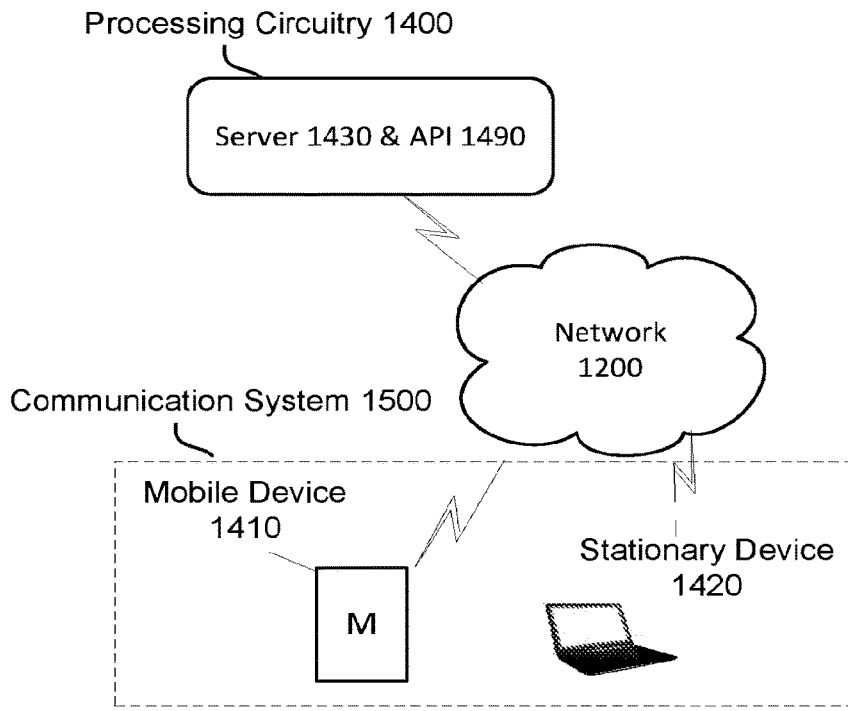
FIG. 1B shows the processing circuitry including a server having an application programming interface in communication with examples of the one or more communication systems including one or more mobile devices and one or more stationary devices, through the network according to an example.

FIG. 1B shows the processing circuitry 1400 including a server 1430 having an application programming interface or API 1490 in communication with examples of the one or more communication systems 1500 including one or more mobile devices 1410 and one or more stationary devices 1420, through the network 1200.

Communication System

The communication system 1500 can be a combination of one or more of the mobile devices 1410 and one or more of the stationary devices 1420. A programmed application, a web app, or mobile app is configured to run on each mobile device 1410 and each stationary device 1420. The mobile device 1410 can be a programmed off-the-shelf electronic device or a proprietary built electronic device, including smartphones, tablets, and wearable technology such as a health band. In another example, the mobile device 1410 includes an accelerometer that is configured to detect movements as footsteps and estimate a distance travelled. The stationary device 1420 can include a web app that is configured to update the scheduling system 1000 on the appointment state and a patient status. In one case, the mobile device 1410 can be configured to access the web app.

The one or more sensor systems 1300 can be configured to sense a spatial position (latitude/longitude) 1310 associated with the mobile device 1410, to associate an actual timestamp 1320 with the spatial position 1310. In another example, each sensor system can identify a spatial accuracy factor 1330 based on a technology or method of sensing.

Figure 1C:
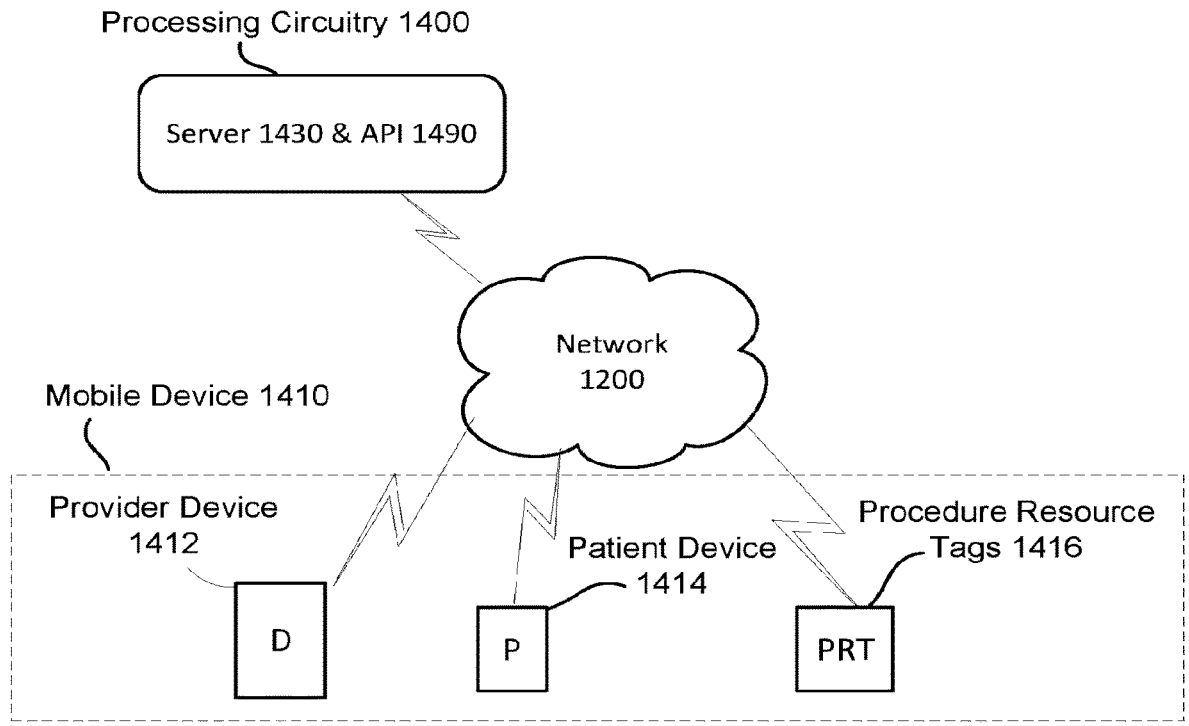
FIG. 1C shows the scheduling system includes more than one mobile device according to an example.

According to an example the scheduling system 1000 includes more than one mobile device 1410 as shown in FIG. 1C. FIG. 1C shows a provider device 1412 which can be a mobile device 1410 assigned to the provider or a provider staff member. In an example, a patient device 1414 can be a mobile device 1410 assigned to the patient. Alternatively, the patient device 1414 can have different forms such as a wristband, a necklace, etc. In an example, one or more procedure resource tags 1416 can be considered a mobile device 1410 each assigned to a procedure resource 3000. In one example, a procedure resource tag 1416 can be an active or a passive RFID sensor.

The provider device 1412 updates the scheduling system 1000 on the one or more provider's locations using the one or more sensor systems 1300. In one example, the provider device 1412 requires a set of security credentials to be activated. The set of security credentials can include a specific local network connection and a passcode. In an example, the provider device 1412 does not store data locally and is mainly pulling from an outside source such that exposure to mismanaged private data is mitigated. In one case, when the provider device 1412 leaves proximity of its original location, or when it becomes connected to a non-authorized network, the mobile app or access to the web app is disabled. In another case, a storage or memory of the provider device 1412 can be wiped clean. All treatment of confidential data will be consistent with regulations set by the applicable agencies, such as HIPAA compliance.

The patient device 1414 updates the scheduling system 1000 with a patient location 2220 using the one or more sensor systems 1300. The patient device 1414 receives communication from the processing circuitry 1400. In one example the communication is a reminder of the appointment timing or a notification that the appointment timing is revised with options to accept or to reject the revised appointment timing. When the revised appointment timing is rejected the next closest appointment timing can be offered or the patient can be offered to request a new appointment timing. In one example, the patient making the new appointment timing request based on the revised appointment timing can be considered a "VIP patient".

In one example, during the appointment, the patient device 1414 logs and monitors a list of available WiFi portals and detects when they substantially change or go out of range. The patient device 1414 does not need to log on the network 1200 to detect a signal strength 1350 of the detected WiFi portals. The patient device 1414 can also detect that the provider device 1414 is within range by using the signal strength 1350 of associated Bluetooth and WiFi signals.

In another example, during the appointment, the patient device 1414 displays a counter with an expected wait time before the next appointment state. The expected wait time can be either before the start of the appointment or during the appointment. This feature will benefit the patient by giving an expectation on their waiting time. With knowing the expected wait time the patient can determine how to use that time best. For example, the patient may want to be productive during the waiting time but they need a minimum duration of time to accomplish a task. Without an expectation of the wait time the patient cannot know if they can accomplish that task. In another example, the patient device 1414 also displays a prediction value reflecting a probability of an accuracy level of the appointment timing or the waiting time. In one example, the accuracy level can be based on the capabilities of one or more scheduling system 1000 components.

Other features the patient device 1414 may have include a warning to indicate when they are getting close to the appointment timing 2100 or if they are at a point of possibly missing their appointment. In one example, the patient location 2220 is detected to determine the patient's ability to make the appointment time. When the patient is too far to arrive by the appointment time due to a distance from the appointment location or a calculated transit time to the appointment location, the provider or the provider staff can be notified to adjust the patient's respective appointment timing 2100 or to cancel the appointment. The transit time can be determined using GPS navigation and traffic monitoring systems such as Google™ maps and traffic. In one case, the patient location is used to modify the prediction value corresponding to their respective arrival time to the appointment location.

The patient location can be used to: define a search filter by proximity of one or more providers relative to the patient location; identify when a patient has arrived to the provider's office by matching the two locations; and infer when a patient has exited the provider's office by un-matching the two locations. In an example, the patient location can be used to identify a provider office that has a lowest waiting time so that the patient can decide between traveling further distance and waiting longer.

Application Programming Interface

According to one example, the API 1490 is configured to maintain secured encryption credentials from multiple electronic medical record (EMR) vendors, representing multiple providers, and multiple patient lists. The API 1490 is configured to query an EMR database to provide the ordered list 1110. The API 1490 is configured for data security to allow confidential competition between different EMR vendors and to address reluctance of more than one provider or EMR vendor to share their patient data due to HIPAA regulation compliance. The API 1490 can use electronic "Chinese walls" to isolate any confidential information from the data shared. According to one example, the API 1490 is configured to gather provider credentials to determine which provider has qualifications to address the patient's medical need, at a time and day requested by the patient.

FIG. 1D

Figure 1D:
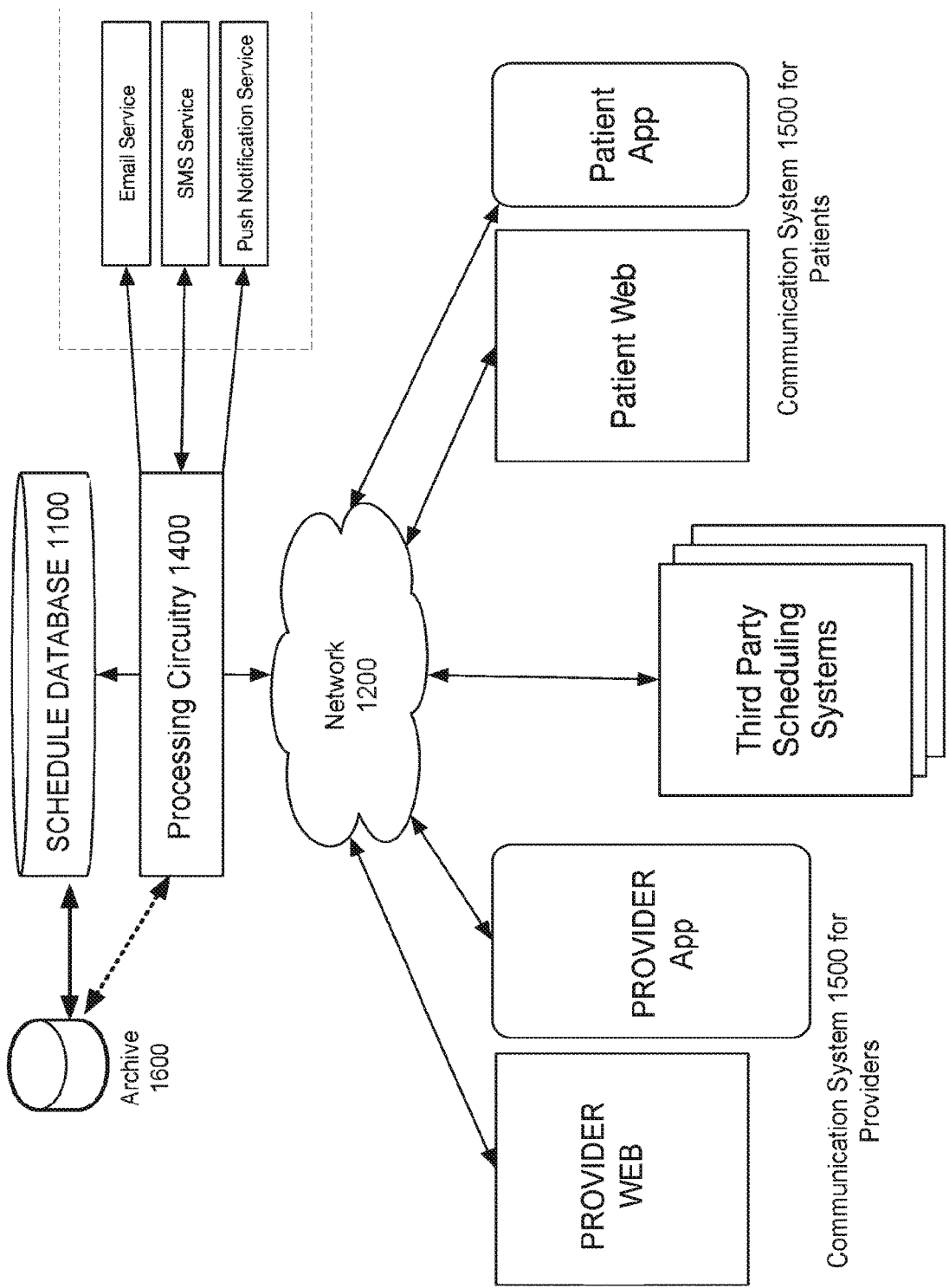
FIG. 1D shows a system overview for an alternate configuration of the scheduling system including the network in communication with the communication system configured for the provider, the communication system configured for the patient, the one or more third party scheduling systems, the processing circuitry, the schedule database, and the archive according to an example.

FIG. 1D shows a system overview for an alternate configuration of the scheduling system 1000 including the network 1200 in communication with the communication system 1500 configured for the provider, the communication system 1500 configured for the patient, the one or more third party scheduling systems, the processing circuitry 1400, the schedule database 1100, and the archive 1600. The processing circuitry 1400 is shown having varying communication services including an email service, a SMS service, and a push notification service. In an example, a push notification and email delivery can be delivered to a third party service (e.g., Apple, Google, etc.). The communication system for the provider is shown including a mobile app specific to the provider operating on the provider device 1412 and a provider web app or interface. Similarly, the communication system for the patient is shown by the programed application specific to the patient and operating on the patient device 1414 and a patient web app or interface.

FIG. 1E

Figure 1E:
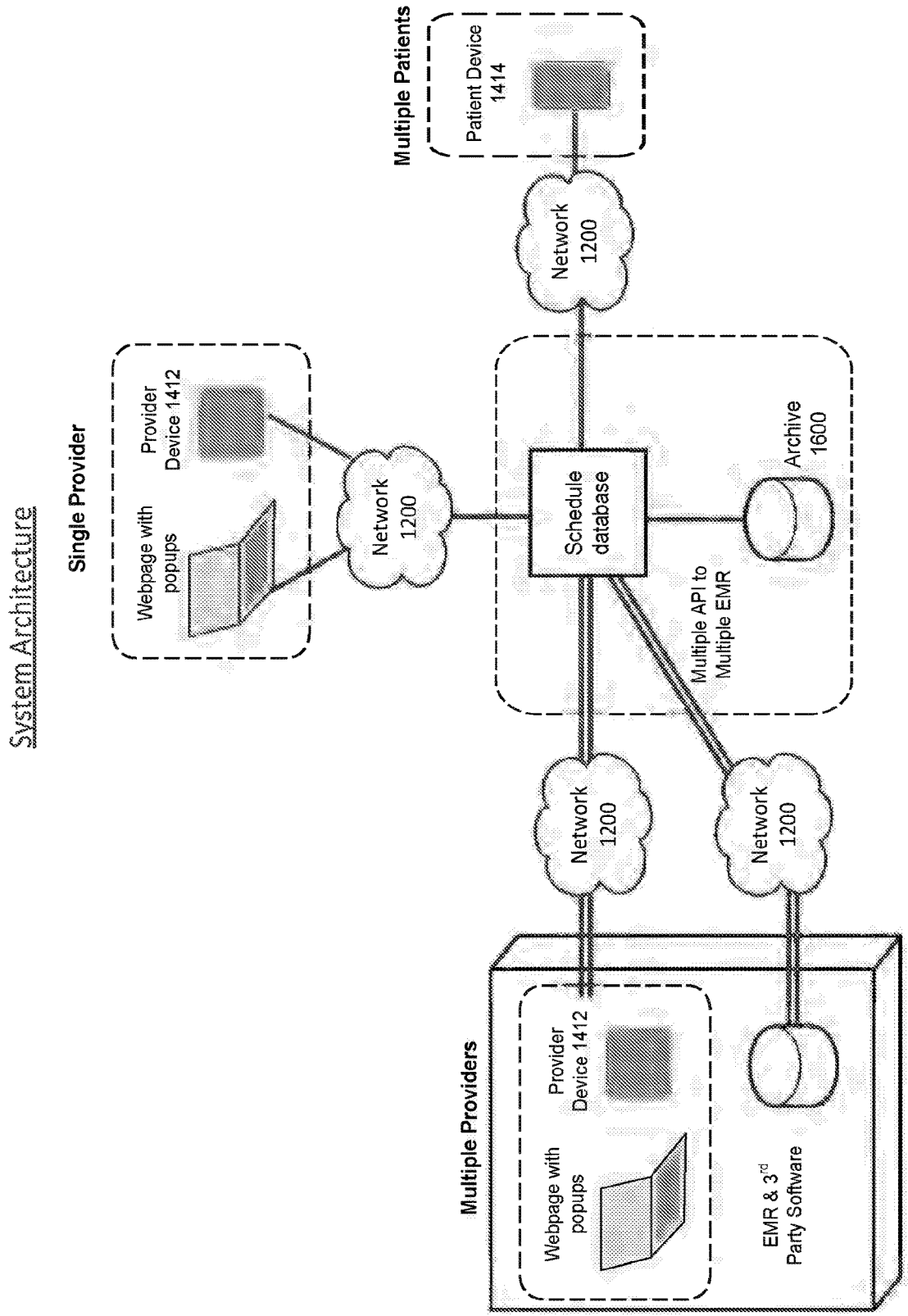
FIG. 1E shows a system architecture of the scheduling system configured for connecting to one or more single providers and multiple providers according to an example.

FIG. 1E shows an example of a system architecture of the scheduling system 1000 configured for connecting to one or more single providers and multiple providers according to an example. In this example, there can be separate networks having different security handling for transferring data. For example, the EMR and third party software in the case of multiple providers can be within a grouped hospital network, whereas the provider device 1412 can use a parallel network connection to the schedule database 1100.

FIG. 1F

Figure 1F:
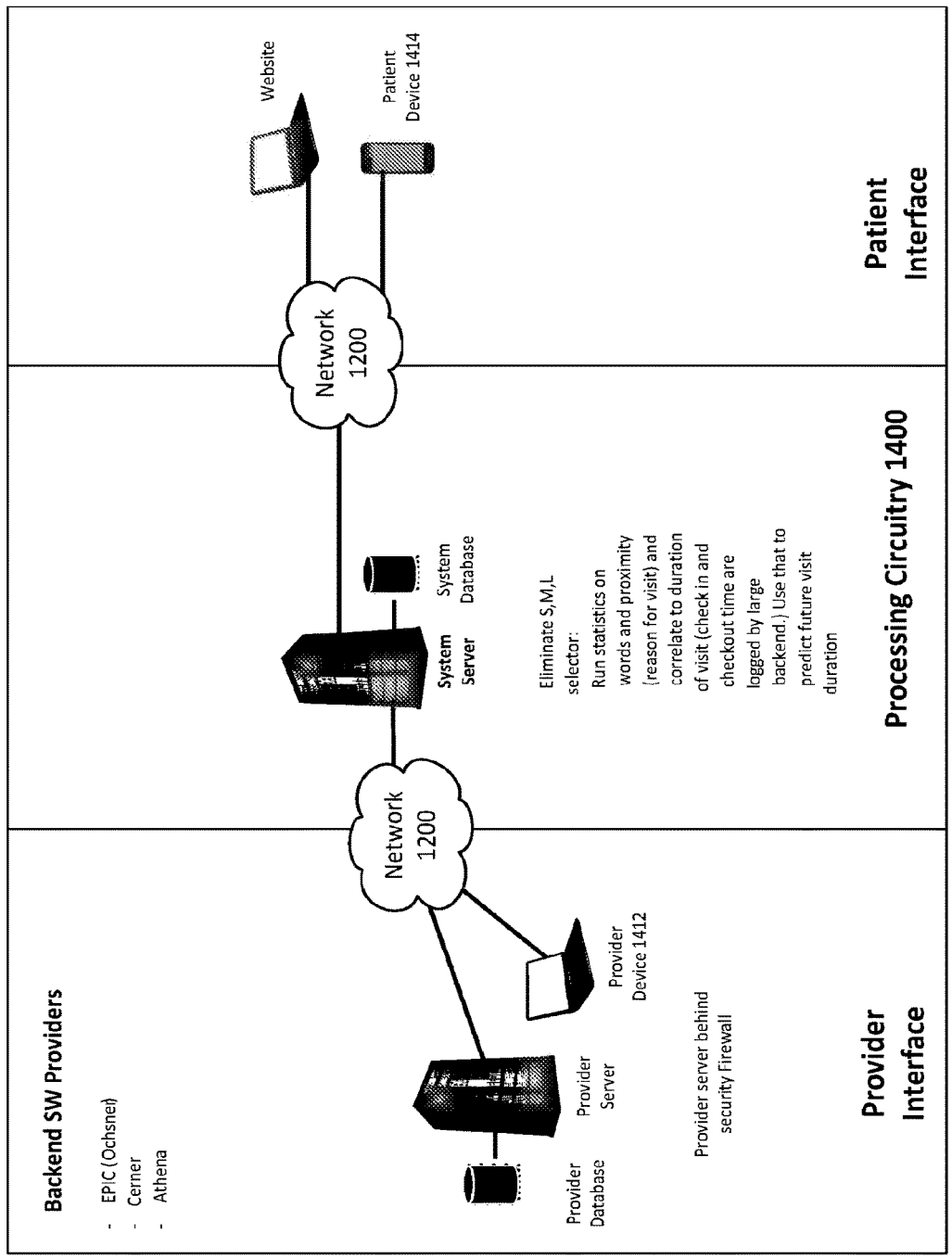
FIG. 1F shows an alternate configuration of the scheduling system showing the network communicating between the scheduling system, the provider, and the patient according to an example.

FIG. 1F shows an alternate configuration of the scheduling system 1000 showing the network 1200 communicating between the scheduling system 1000, the provider, and the patient. Here, the provider includes the provider device 1412, a provider server, and a provider database. The provider server is behind a security firewall and includes one or more third party or backend software providers such as EPIC, Cerner, and Athena. Data and information exchanged by the provider server may be stripped of confidential information and HIPAA protected information. A hash name can be used for maintaining privacy for the patient with the associated patient ID 1120 with appointment information such as the appointment type 1133 and the appointment timing 2100.

FIG. 1G

Figure 1G:
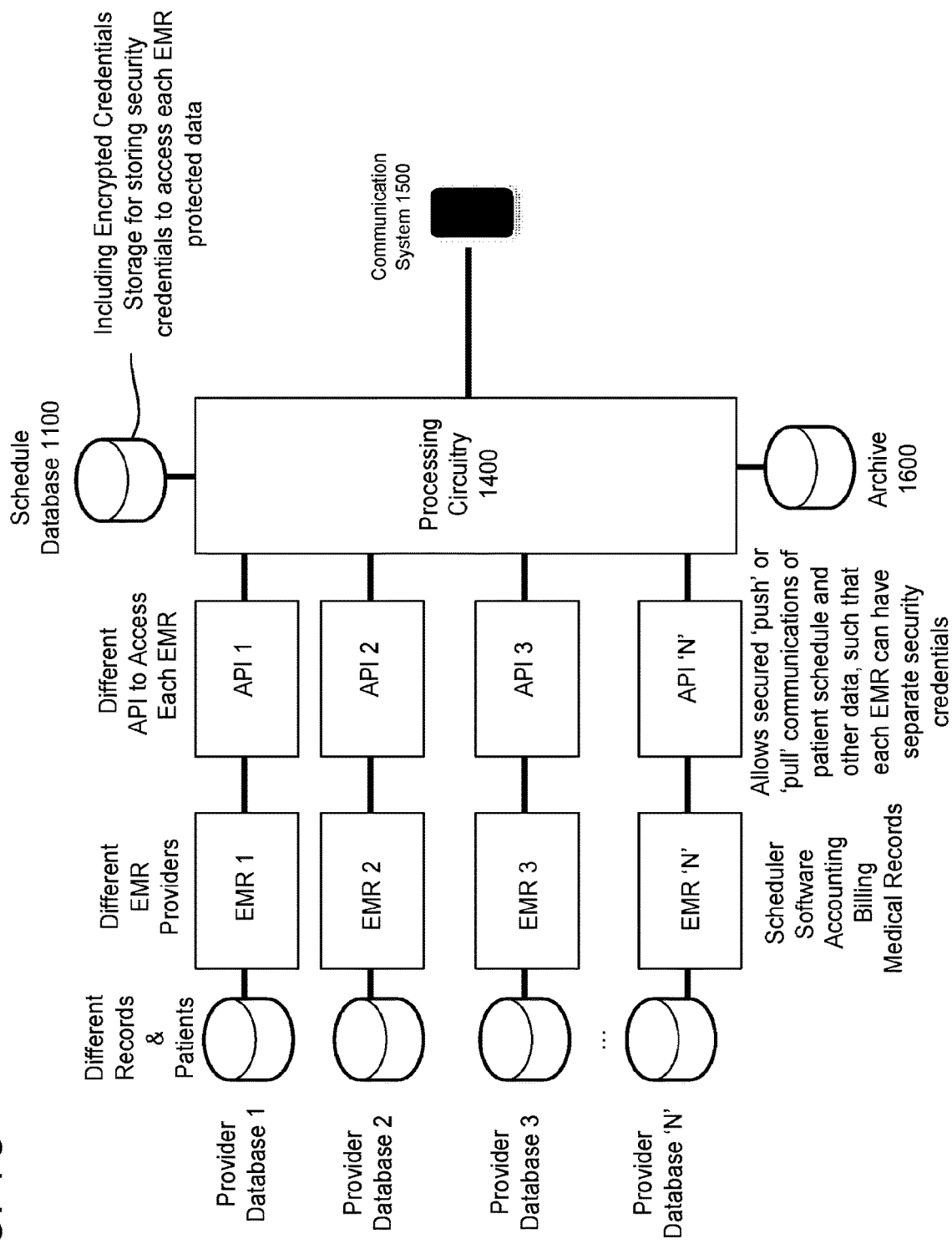
FIG. 1G shows another embodiment of the scheduling system configured for multiple providers according to an example.

FIG. 1G shows another embodiment of the scheduling system 1000 configured for multiple providers. In an example, each provider can have a provider database having a set of patient records accessible to a unique EMR provider. A set of unique APIs can be configured to allow secured 'push' or 'pull' communications of patient schedule and other data, such that each unique EMR can be in communication with the processing circuitry 1400 using separate security credentials access according to an example.

FIG. 2A

FIG. 2A shows an example of the ordered list 1110 shown in a table. Each row of the ordered list 1110 represents a patient appointment entry. Each patient appointment entry includes an associated patient represented by a patient ID 1120 and a set of appointment entry components 2000. According to one example, the set of appointment entry components 2000 can be made of different types of data including the appointment timing 2100, one or more appointment locations 1135, an appointment type 1133, an appointment provider 1134, a patient status 2200, one or more medical procedures or procedure types 1150, and a set of assigned procedure resources 3000. The appointment type 1133 can be divided into or include one or more appointment states.

In one example, the appointment timing 2100 can include one or more of an appointment day, an estimated appointment time or start time, an estimated appointment end time, a set of one or more predetermined appointment durations (PAD), a set of one or more actual appointment timing or actual durations (AAD), and a set of one or more predicted timing corresponding to each assigned procedure resource 3000, which can be predicted durations or predicted timestamps. Each estimated appointment time is a specific time on a day, whereas each PAD is a duration of time. Once each PAD is assigned to the schedule, the scheduled PAD will have a predicted start time or a first predicted timestamp and a predicted end time or a second predicted timestamp with respect to the PAD beginning and end.

The predicted timing can include the estimated appointment time as well as the start and end time for each scheduled PAD. Each appointment state can have a respective PAD that reflects a predicted duration of time for the appointment state. In one example, each appointment PAD can reflect a sum of the set of PADs reflecting the set of all appointment states for that appointment. In one example, the predicted timing includes a first predicted timestamp for a start time of an appointment state scheduled in the ordered list 1110 and the respective PAD for the appointment state determines a second predicted timestamp for an end time of the appointment state scheduled on the ordered list 1110.

In one example, performing each procedure type 1150 requires a specific set of one or more procedure resources 3000 in a generally particular order to that procedure type 1150. Scheduling of the appointment type 1133 therefore schedules one or more procedure types 1150 and the set of one or more procedure resources 3000 in their order and duration in a respective availability queue 3500. In some cases the ordering and duration can be modified as needed by the provider.

In another embodiment, each appointment further includes a set of prediction values 1140 corresponding with each appointment entry component 2000.

The appointment location 1135 includes different types of locations with varying spatial distances and spatial precisions. In one example, the appointment location 1135 further includes a respective spatial accuracy factor. For example, the appointment location 1135 includes one or more of a healthcare facility location, a provider office, a waiting room location, one or more exam room locations, one or more procedure room locations, each of which require different degrees of spatial precision to be identified. The varying spatial distances and spatial precisions result in different precisions for different types of sensing systems. Therefore, in this example, a corresponding set of prediction values 1140 can be assigned to the appointment location 1135 based on the spatial accuracy factor. The spatial accuracy factor with respect to the appointment location can be used to rank or to modify the outputs from the one or more sensor systems 1300 based on their respective spatial accuracy factors.

In this example, the ordered list 1110 includes an ID for the associated patient 1120, the appointment type 1133, an estimated appointment time, the PAD, the AAD, the patient status 2200, a notification status, a procedure type, and a set of procedure resources 3000. The ID for the associated patient 1120 can include one or more of a patient name, a patient registration number, or an EMR database enumeration. In this example, the PAD and the AAD are shown as a cumulative number. In an expanded view, the PAD and the AAD can be shown as the entire set that make up their totals.

The appointment type 1133 can reflect a purpose of the patient appointment that also reflects the expected one or more medical procedures. The estimated appointment time is the scheduled start time of the patient appointment. In one example, the estimated appointment time can be determined by the sum and the ordering of the predicted timing for that day. In this example, the predicted timing can be a sum of all of the PAD's for that day, sum of all the procedure resources 3000 scheduled, the sum of all of the appointment states scheduled, or the sum of all the appointment timing 2100 including any breaks as a whole.

In the example shown, the patient status 2200 is shown as an abbreviated version reflecting the proximity-time of the patient including the patient location 2220 and a respective actual timestamp 1320. The one or more sensing systems 1300 are used to track the spatial position 1310 of the patient with the associated patient ID 1120 and generate the patient location 2220. The patient status 2200 reflects one or more appointment locations 1135 associated with a patient state 2210. The actual timestamp 1320 can indicate a time at the respective spatial position 1310.

In one example, at beginning of an appointment day the ordered list 1110 includes "N" estimated appointment times or start times that are all at or near the office opening time, where "N" equals the number of available exam rooms to be used. The ordered list 1110 is created prior to day of appointment and is continually updated as each predicted timing becomes known by the actual timing.

Network

The network 1200 is any network or circuitry that allows the schedule database 1100, the archive 1600, the one or more sensor systems 1300, the processing circuitry 1400, and the one or more communication systems 1500 to communicate with each other. The network 1200 may include the Internet or any other medium capable of communicating data between devices. Suitable networks can include or interface with any one or more of a local intranet, a PAN (Personal Area Network), a LAN (Local Area Network), a WAN (Wide Area Network), a MAN (Metropolitan Area Network), a VPN (Virtual Private Network), or a SAN (storage area network). Furthermore, communications may also include links to any of a variety of wireless networks, including WAP (Wireless Application Protocol), GPRS (General Packet Radio Service), GSM (Global system for Mobile Communication), CDMA (Code Division Multiple Access) or TDMA (Time Division Multiple Access), cellular phone networks, GPS (Global Positioning System), CDPD (Cellular digit packet data), Bluetooth radio, or an IEEE 802.11 based radio frequency.

As can be appreciated, the network 1200 can be a public network, such as the Internet, or a private network such as an LAN or WAN network, or any combination thereof and can also include PSTN or ISDN sub-networks. The network 1200 can also be wireless such as a cellular network including EDGE, 3G and 4G wireless cellular systems. The wireless network can also be WiFi, Bluetooth, or any other wireless form of communication that is known.

Archive

The archive 1600 can include a database including one or more of a list of past appointment entries 1610 or a list of appointment types. Each past appointment entry 1610 can include a respective patient appointment having a respective archived timing 1620 associated with each appointment entry component 2000. In one example the archived timing 1620 can be a trend formula that correlates the timing duration to other factors such as a duration of the patient's prior appointment, the patient's seniority or age, the time of day, the provider, the appointment location, the medical need, etc.

Sensor Systems

Each sensor system 1300 senses at least one of a discrete signal 1340 corresponding to a manual input of the sensed spatial position 1310 and the actual timestamp 1320, and a signal strength 1350 of a continuous electromagnetic wave, an acoustic pressure, or an optical light associated with the patient, enabling the determination of the sensed spatial position 1310, the actual timestamp 1320, and the spatial accuracy factor 1330.

According to an example, the one or more sensor systems 1300 can be configured to sense the spatial position 1310 associated with one or more appointment entry components 2000 or the one or more procedure resource tags 1416, enabling determination of the spatial position 1310 associated with the patient with the associated patient ID 1120 relative to one of the appointment locations 1135 or the one or more procedure resource tags 1416.

According to an exemplary example, the scheduling system 1000 includes at least two sensor systems 1300 with different spatial accuracy factors 1330 to distinguish two spatial positions 1131 of two different appointment entry components 2000. For example, a GPS system is not adequate to distinguish different levels of a multi-leveled structure. In another example, the spatial accuracy factor 1330 of the GPS signal cannot distinguish a location separated by a physical boundary. Also, when approximately 10 feet inside in a building, roughly 20-30 dB of signal attenuation occurs at 1.6 GHz caused by common office building construction. Therefore, a second sensor system 1300 is used to determine the spatial position 1310.

A time-of-flight radio location becomes highly inaccurate in buildings due to changes in multi-path environment, resulting from small changes in distance. The signal strength 1350 of a valid (e.g. CRC/error validation) message is more predictable. Use of multiple 'channels' of independent information can further improve accuracy.

In an example, the signal strength 1350 can vary from −100 dB to 0 dB. An expected variance of the signal strength 1350 due to signal fading is 10-20 dB. Signal variation and attenuation by shading is expected in buildings, parking garages, etc., and have a particularly large effect for satellites near the horizon. Other time-of-flight radio location systems within a building become unreliable due to severe multipath signal variation, for example inches of antenna position delta can cause 500 ns signal delays, which can cause approximately 500 foot errors. These signal changes are compounded with that of attenuation due to entering or exiting a room.

According to an example, the sensor system 1300 can include a signaler. The signaler or beacon can be a pre-built, off-the-shelf signaling device such as a Bluetooth beacon or utilizing Near Field Communication hardware, hardware configured to communicate with the WiFi network, hardware to communicate an electronic image (e.g. encode an image on a device) or a physical image (e.g., QR sticker), or a proprietary or off-the-shelf electronic device producing audible or in-audible tone. In the case of the physical image, a scanning device (e.g., camera) can be installed at various locations in the office as a part of the sensor system (i.e., QR stickers will be scanned upon entry to a waiting area and an exam room). The Bluetooth beacon is configured to perform a close proximity (5-10' ft) digital 'handshake', which yields high proximity-temporal accuracy-reliability. The signaler is configured to generate a transmitted signal or signal such as a raw or encoded message sent or interpreted electronically, as well as to sense locations of the one or more communication systems 1500. In an example, the beacon can be an active or a passive RFID sensor.

In the alternative, the signaler can use WiFi, or the like, which operates at a longer range. The signaler can switch power outputs from 100 mw to 10 mw to 1 mw (whisper/shout), further the receiving side can measure a signal to noise (SNR) of valid data packs so as not to be confused with colliding signals from other WiFi systems.

In the alternative the provider device 1412 can emit a coded audible tone at approximately 16 kHz, but at low amplitude so that it is not easily heard. The patient device 1414 can listen for this tone, and integrate over 1,000-10,000 cycles resulting in 30-40 dB of detector gain. The emitted signal is configured to achieve process gain or to uniquely identify sender.

In one example, the provider device 1412 can function as the sensor system 1300 to provide the discrete signal 1340 and thereby generate the actual timestamp 1320. In another example, the patient device 1414 can function as the sensor system 1300 to provide the discrete signal 1340 and thereby generate the actual timestamp 1320.

According to an example, the stationary device 1420 can function as the signaler or a mobile device 1410 that is placed in a holder at an assigned location.

Table 1 shows examples of proximity determination method with availability, location, and time accuracy.

more of the provider device's 1412 capabilities when outside a proximity of the provider office. For example, the capability to access encrypted data from an unsecure network. This feature reduces the risk of mishandling confidential information.

In another example the sensor system 1300 will sense that the patient has left proximity to the provider's office and trigger the processing circuitry 1400 to send the patient an appointment survey regarding their appointment. In one case the appointment survey can include preferences about the appointment states and about the assigned procedure resources 3000. The appointment survey responses can be saved in the archive 1600 and used for the scheduling of future appointments.

In another example the sensor system 1300 will sense the patient location 2220 and use it to search for providers with appointment availability in the vicinity. In another example, the sensor system 1300 is used to trigger a notification of the patient's arrival to the office and to provide a digital copy of the patient's check-in paperwork such as their photo ID, insurance information, and health questionnaire or survey etc., to the provider device 1412. In another example, the sensor system 1300 will track a patient's distance from the appointment location 1135 and notify the provider device 1412 when the patient is expected to be late.

Virtual Zones

In one embodiment the one or more sensor systems 1300 can be used to establish one or more virtual boundaries or virtual zones. Each virtual boundary or virtual zone can be

TABLE 1

| TYPE | RELIABILITY | AVAILABILITY | ACCURACY |
|---|---|---|---|
| GPS Radio location service | Good outside the building, poor inside a building | Everyone with a phone (may become unavailable inside a building) | Accurate outside the building but becomes less accurate within the building |
| WiFi, Bluetooth | Proximity/signal strength of WIFI's detected at time of appointment | Everyone with WiFi, Bluetooth | Very accurate |
| Accounting system, patient info | Very reliable | Not always available | Excellent accuracy |
| Nurse clicks done button | Excellent reliability | When nurse has the device to click | Excellent, when the nurse complies |
| Patient clicks done button | Excellent reliability | When patient has the device to click | Excellent, when the patient complies |
| Optical emitters | Excellent, short rang, line of sight | Available in some mobile devices, else requires installation of hardware | Very accurate to room level precision |
| Patient barcode to Provider barcode | Excellent reliability | When both devices are available to read barcode | When the patient/doc complies |
| Camera Recognition | Reliable | When the device is in office | High accuracy (maybe not always perfect) |
| Audio Recognition | Reliable | When the device is in office | High accuracy (maybe not always perfect) |
| Accelerometer action | Reliable | When the patient has a smart phone | Excellent accuracy |
| Eye Scanner | Excellent reliability | When the doc office has an eye scanner | Excellent accuracy |
| Finger acknowledgement | Excellent reliability | When the doc office has a finger scanner | Excellent accuracy |
| Text message, email, phone call, voicemail | Somewhat reliable | When patient checks frequently | When the patient complies |

Sensor System Functions

The sensor system 1300 can be used to perform different functions according to different scenarios. In one example, the sensor system 1300 can be used to deactivate one or used to define or to identify any of the appointment locations 1135. The appointment locations 1135 include hospital, clinic, patient waiting rooms, lab rooms, examination room, procedure rooms, etc. The one or more providers include the doctor, the physician assistant, the nurse, the technician etc. The procedure resources 3000 can include pieces of equipment and supplies carts, etc. In one example the virtual zones are one or more fixed zones. In another example the virtual zones include one or more mobile zones.

Each virtual boundary or virtual zone can be configured to monitor a communication system or a procedure resource 3000. The one or more virtual boundaries can be further configured to monitor the mobile procedure resources 3100 within the fixed procedure resources 3200 that represent a location. In this example, the ordered list 1110 includes at least one procedure type 1150 requiring at least one fixed procedure resource 3200 and one mobile procedure resource 3100.

The virtual zones can be configured for the purposes of monitoring one or more enclosed, intersecting, or disjoint fixed appointment locations 1135, one or more providers, one or more mobile assets, and one or more patients being cared for. Each location, provider, procedure resource, and patient can be monitored and associated with intra-appointment analytics of patient care by services provided and reimbursement codes billed.

In one example, each unique sensor system and beacon can be registered in software to track their respective identities and to associate their spatial location with a respective appointment location. In one example, the timestamps of an intersection between the virtual zone and an entity being monitored, the archive of appointment records, and a set of reimbursement codes can be used to calculate the analytics of the intra-appointment services provided during the appointment, whereby the detailed analytics provide a means for enhanced prediction of appointment scheduling.

In this case, division of the intra-appointment analytics by intersection and time are taken with specificity as required. In one case the specificity is used to track provider service efficiency, medical event tracking (e.g. handling of emergencies such as a "code blue"), and quality of patient care. Here, the appointment time duration is divided into segments indicating when a service is being actively being provided to the patient and when the patient is waiting.

In one example, the sensor systems 1300 can include sensors and beacons of different types of devices having different signal types and/or strengths, specifically and judiciously placed at selected locations to increase sensitivity, reduce signal interference, and better differentiate the virtual zones. In another example, an audio, visual and/or motion tracking system can be used to confirm identification of the entity being tracked, to distinguish virtual zones, and to trigger activation of another sensing system 1300. In another example, the virtual zones can be used in concert with other systems and sources of patient information such as an insurance verification system at check-in and a payment system for any final payments during the check-out process.

In an example, a virtual zone can be established by installing a beacon in each room and allowing patient devices to detect the beacons based on a signal strength. In an example, a virtual zone can be established by assigning a beacon to each patient and installing a sensor system (e.g. gateway, beacon detector) in each room that can be triggered upon entry of each patient or provider.

Processing Circuitry

According to an example, the processing circuitry 1400 is configured to communicate with the schedule database 1100, the archive 1600, the one or more sensor systems 1300, and the one or more communication systems 1500. The processing circuitry 1400 is also configured to perform multiple schedule modification processes to the schedule database 1100 as further described herein.

The processing circuitry 1400 is configured to communicate notifications and alerts to the one or more communication systems 1500. In one example, the processing circuitry 1400 transmits a communication or notification over the network 1200 to activate the mobile app on the mobile device 1410, which causes the notification to display on the mobile device 1410 or the stationary device 1420 and enables connection of the mobile device 1410 or the stationary device 1420 to the processing circuitry 1400 when they are in communication with the network 1200. The processing circuitry 1400 can be configured to communicate the revised appointment timing 2100 to an affected patient. Alternatively, the office staff can initiate the communication manually. In one case, the office staff can use the web app. A location service update for determining the patient distance relative to the provider or an appointment location can be updated continuously. However, the location service update can be different from how often the patient will be notified of any change. In one example, the notification can also function as a button to accept or to refuse the revised appointment timing. When the revised appointment timing is rejected the next closest appointment timing can be offered or the patient can be offered to request a new appointment timing. In one example, the patient making the new appointment timing request based on the revised appointment timing can be considered a "VIP patient". In another example, the one or more probability values corresponding to the appointment timing are also sent.

FIG. 2B

Figure 2B:
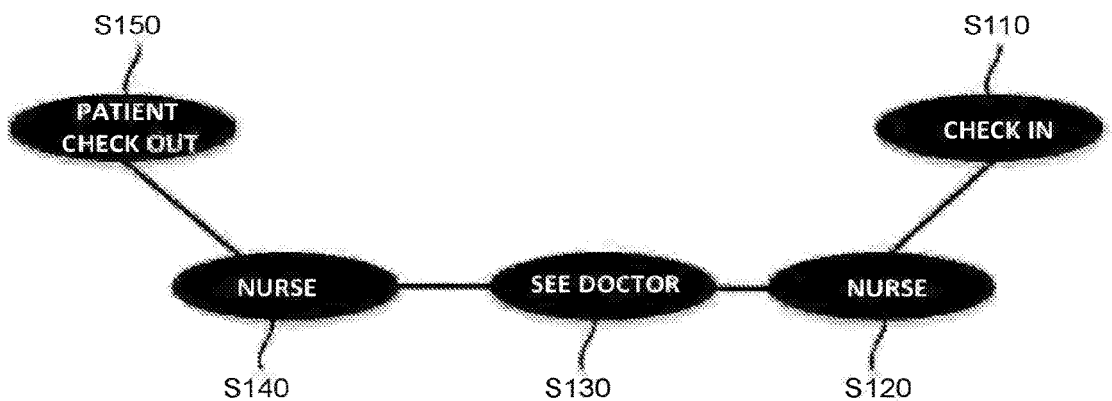
FIG. 2B shows an appointment state diagram, appointment state diagram A, having a set of appointment states making up an appointment according to an example.

FIG. 2B shows an example of an appointment state diagram, appointment state diagram A, of a set of appointment states making up an appointment according to one example. The one or more appointment states can be determined by the appointment type 1133, the medical need, one or more billing codes used for reimbursement. In another example, each appointment state can be described by a service being performed during a patient visit or by the patient state 2210.

In the example shown, at appointment state S110 (check in) the patient arrives to the waiting room and enters into a 'check-in' appointment state. Determination that the patient arrived to the waiting room can be done by several scenarios. In one example, the scheduling system 1000 matches the patient location 2220 to the location of the waiting room. In an example, when within a time close to the scheduled appointment, the time of the appointment can be used as the actual timestamp 1320 reflecting the arrival time. In another example, when within a close time to the scheduled appointment, the actual timestamp 1320 from the sensor system 1300 can be used as the arrival time.

As an example, the patient location 2220 can be detected by at one of satellite triangulation, cell or micro-cell SNR, signal strength 1350 or CDMA time of flight or communications with a radio data system in the waiting room or provider's office such as WiFi, Bluetooth or the like, an alternative radio beam, an acoustic signature audible or ultrasonic, IR or other optical spectrum, or by check in with the provider's staff.

At S120 (nurse) the nurse leads the patient to an assigned exam room resulting in completion of the 'check-in' appointment state and start of the following appointment state. In one example, the patient leaving the waiting room can be a proxy for entering the exam room. Alternatively, any one of a change in a cellular or micro-cellular SNR signal strength 1350, or change in the WiFi signal strength 1350, or reduction in acoustic strength, or optical sensor, or other wireless beacon, or waiting room administration log-in the event or a computer, or staff logging patient state 2210 on the provider device 1412 or the stationary device 1420, or the patient device 1414 communicating with the stationary device 1420 mounted/located in the exam room can be used to determine the patient is in the assigned exam room.

At S130 (see doctor) the doctor visits the patient for the first time. The completion of the examination by the doctor can be indicated by methods including the provider staff changing the appointment state or the patient state 2210 using the provider device 1412 or the stationary device 1420.

At S140 (nurse) a nurse completes any needed procedure type 1150 or steps. In another example, the nurse escorts the patient out of the exam room and back to the waiting room. Determination of the patient exiting the examination room is indicated by methods including detection of a change in cellular or micro-cellular SNR or signal strength 1350, or change in the WiFi signal strength 1350, or reduction in acoustic strength, or optical sensor, or other wireless beacon, or that the patient's device 1414 can no longer communicate with the stationary device 1420 assigned to the exam room, or that the signal strength 1350 is significantly reduced, or by manual input by the provider staff.

At S150 (patient check out) the patient checks out of the appointment. The detection of the patient checking out is done by a variety of means. One or more of the sensor systems 1300 detects that the patient location 2220 is no longer the appointment location 1135, thereby triggering the appointment state to change to "Patient checked out." Other examples include the patient location 2220 matches the patient location 2220 prior to check in, the GPS signal associated with the patient recognizes that the patient is outside the provider's office, the WiFi ID within or near the provider's office no longer senses the patient device 1414, as well as the provider or clinical staff manually inputting to the scheduling system 1000 that the appointment is complete and the exam room is available.

According to one example, the appointment states that can be most influential to provide spatial-temporal information in the scheduling system 1000 include 1) the actual timestamp associated with the patient arriving at the waiting room, 2) the actual timestamp associated with when the patient arrives to the assigned exam room, and 3) the actual timestamp associated with when the patient is leaving the exam room to begin the 'check-out' appointment state. More granular appointment states can further enhance accuracy of the schedule timing.

FIG. 2C

Figure 2C:
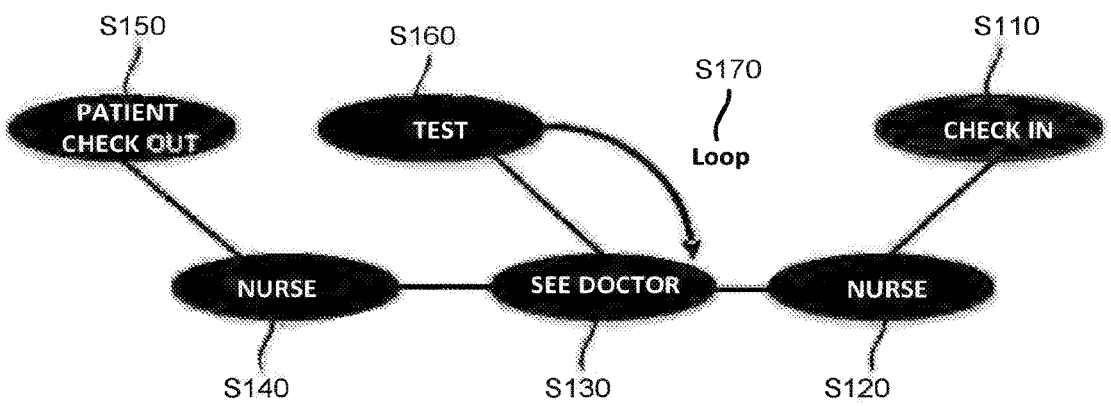
FIG. 2C shows another example of the appointment state diagram, appointment state diagram B, further including a test state and a loop state where the test state is repeated according to an example.

FIG. 2C shows another example of the appointment state diagram, appointment state diagram B, further including a S160 (test) a test state and a S170 (loop) loop state where the test state is repeated. At S160 (test) a test or procedure type 1150 is performed. In one example the patient is moved to another room such as a procedure room. In another example, the patient remains in the assigned exam room and the equipment required for the procedure type 1150 is brought in. At S170 (loop) the test step is repeated as necessary. In one example, the provider reviews a test result with the patient. In another example the provider reviews the test result at another location. In this case, although the patient may be alone in the exam room or the procedure room, the provider is actively working on providing a service to the patient, and therefore, any timer tracking the patient waiting time can be configured to reflect that.

FIG. 2D

FIG. 2D shows another embodiment of the appointment state diagram, shown here as a list and reflecting the one or more appointment states in a specific ordering that reflect the one or more procedure types 1150 required for the appointment type 1133 according to an example. In this example, each appointment state includes the appointment location 1135, the one or more PADs, the one or more procedure resources 3000, and their respective prediction value. Here, three appointment states are shown reflecting three appointment types with differing content. In this example, the appointment types are described by the appointment states of the appointment including the timing expected for certain ones that can reflect different procedure types 1150. For example, the time duration of a provider's consultation relates to the billing codes used for reimbursement. In one case the provider's consultation is twice as long, which is reimbursed at a higher rate. According to one example, the actual timestamps are used to modify the appointment type 1133 or the procedure types 1150 in the ordered list 1110, and thereby changing the billing code used for reimbursement.

FIG. 2E

FIG. 2E shows an example of a shortened ordered list 1110 only including the patient ID, the estimated appointment time and only one cumulative PAD for each patient appointment entry as the appointment entry components 2000.

FIG. 3A

Figure 3A:
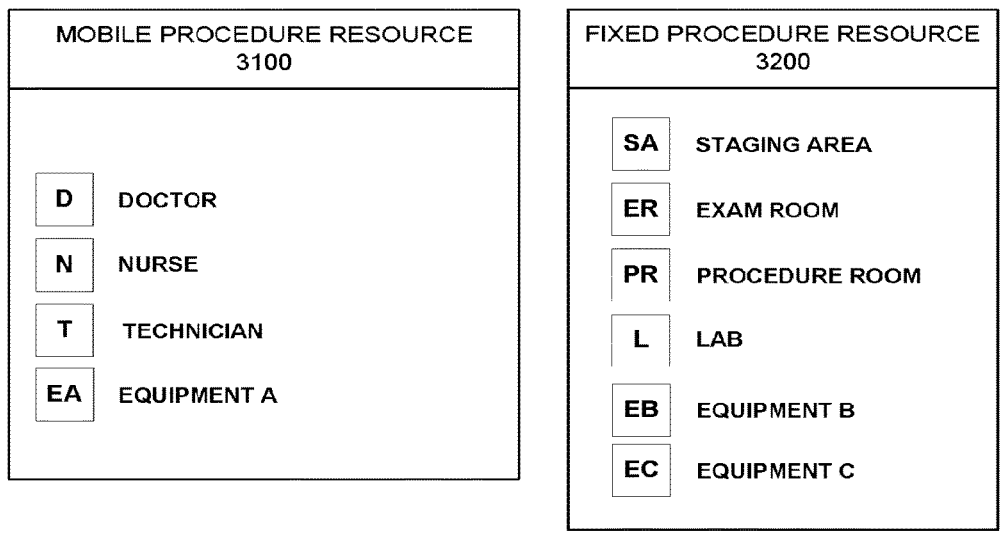
FIG. 3A shows a key for designation of a set of procedure resources for a procedure type associated with the patient appointments according to an example.

FIG. 3A shows a key for designation of a set of procedure resources 3000 for the procedure type 1150 associated with the patient appointments. Each procedure resource 3000 includes a combination of a set of mobile procedure resources 3100 and a set of fixed procedure resources 3200. Examples of mobile procedure resources 3100 include a provider, a doctor, a nurse, a technician, and an equipment type A. The equipment type A is one that is shared between different appointment locations 1135. Examples of the fixed procedure resources 3200 include a staging area, an exam room, a procedure room, a lab, an equipment type B, and an equipment type C. The equipment type B is one that is assigned to an appointment location 1135. The equipment type C is one that is used for performing a procedure task, but does not require a mobile procedure resource 3100 to be present to be performing the service, such as lab equipment for performing blood tests.

FIG. 3B

Figure 3B:
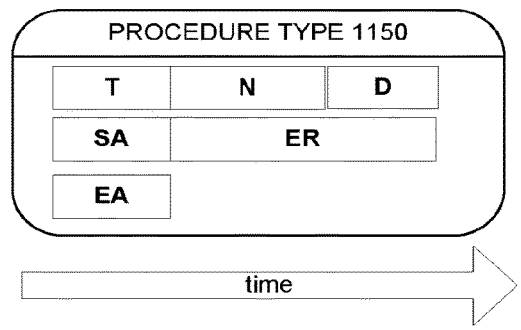
FIG. 3B shows the procedure type including a set of assigned procedure resources according to an example.

FIG. 3B shows an example of the procedure type 1150 including a set of assigned procedure resources 3000. Each procedure type 1150 requires a set of one or more procedure resources 3000 in a generally particular order. In some cases the ordering can be modified.

FIG. 3C

Figure 3C:
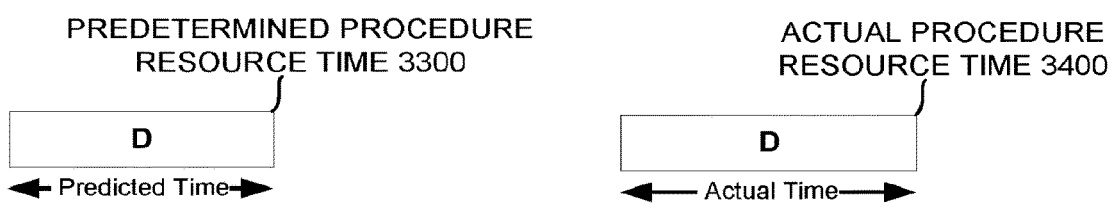
FIG. 3C shows an elongated indicator indicating a pre-determined procedure resource time (PPRT) and an actual procedure resource time (APRT) on the schedule according to an example.

FIG. 3C shows an elongated indicator indicating a predetermined procedure resource time 3300 (PPRT) and an actual procedure resource time 3400 (APRT) on the schedule. The PPRT 3300 reflects the PAD or the time each scheduled procedure resource 3000 is allocated on the schedule. The APRT 3400 reflects the AAD or the actual time duration each scheduled procedure resource 3000 was in use on the schedule. Upon completion of each scheduled procedure resource 3000, the actual duration will be known, the PPRT 3300 is changed to reflect the APRT 3400, and the restacking method can be triggered. The PPRT 3300 and the APRT 3400 indicators can be used to allocate the set of procedure resources 3000 to each procedure type 1150, to minimize any unassigned resource time and avoid duplicate allocations, as well as to calculate any changes to the appointment timing.

FIG. 3D

FIG. 3D shows an example of the patient status 2200 as a growing list, where each entry includes the patient state 2210, the patient location 2220, the actual timestamp, and a respective timer or duration count depending on if the patient state 2210 is complete. In one example both the beginning and ending timestamps, as well as the duration are recorded for each patient state 2210. The scheduling system 1000 can compare the timestamps of each patient state 2210 with those of the allocated procedure resources 3000 associated with the patient appointment to determine the waiting time for each appointment state.

In another embodiment, the ordered list 1110 can include a provider status that is similar as the patient status 2200 and has a similar growing list as the patient states 2210. In this case the provider status and the patient status 2200 list can be compared for different functions. In one example, a provider location can be tracked similar to the patient location and used to update the provider status. The provider location can also be used to identify when a provider has arrived or left the provider's office and to define a search filter by proximity indicating the provider's location within the patient's search result for available appointments.

In one example, the comparison of the patient status 2200 and the provider status can function to determine the total waiting time and to verify if the procedure types 1150 were accurately billed. In another example, the patient status 2200 and the provider status can function to identify delays in the schedule and trigger the restacking process. For example, when the patient has not checked-in yet reflecting the patient state 2210 as "not arrived" or "in the waiting room", and the provider state indicates to go to the exam room to see the patient. Another case is when the provider state and the patient state 2210 indicate that they are remaining in the exam room beyond the predicted timing duration for a "Primary doctor visit" appointment state. In these cases restacking of the ordered list 1110 and or schedule is triggered due to misalignment of the provider state and the patient state 2210 or due to unexpectedly longer appointment state.

FIG. 3E

FIG. 3E shows examples of methods and devices to establish the proximity-time. The methods and devices in the chart refer to different figures in this disclosure.

FIG. 4A

Figure 4A:
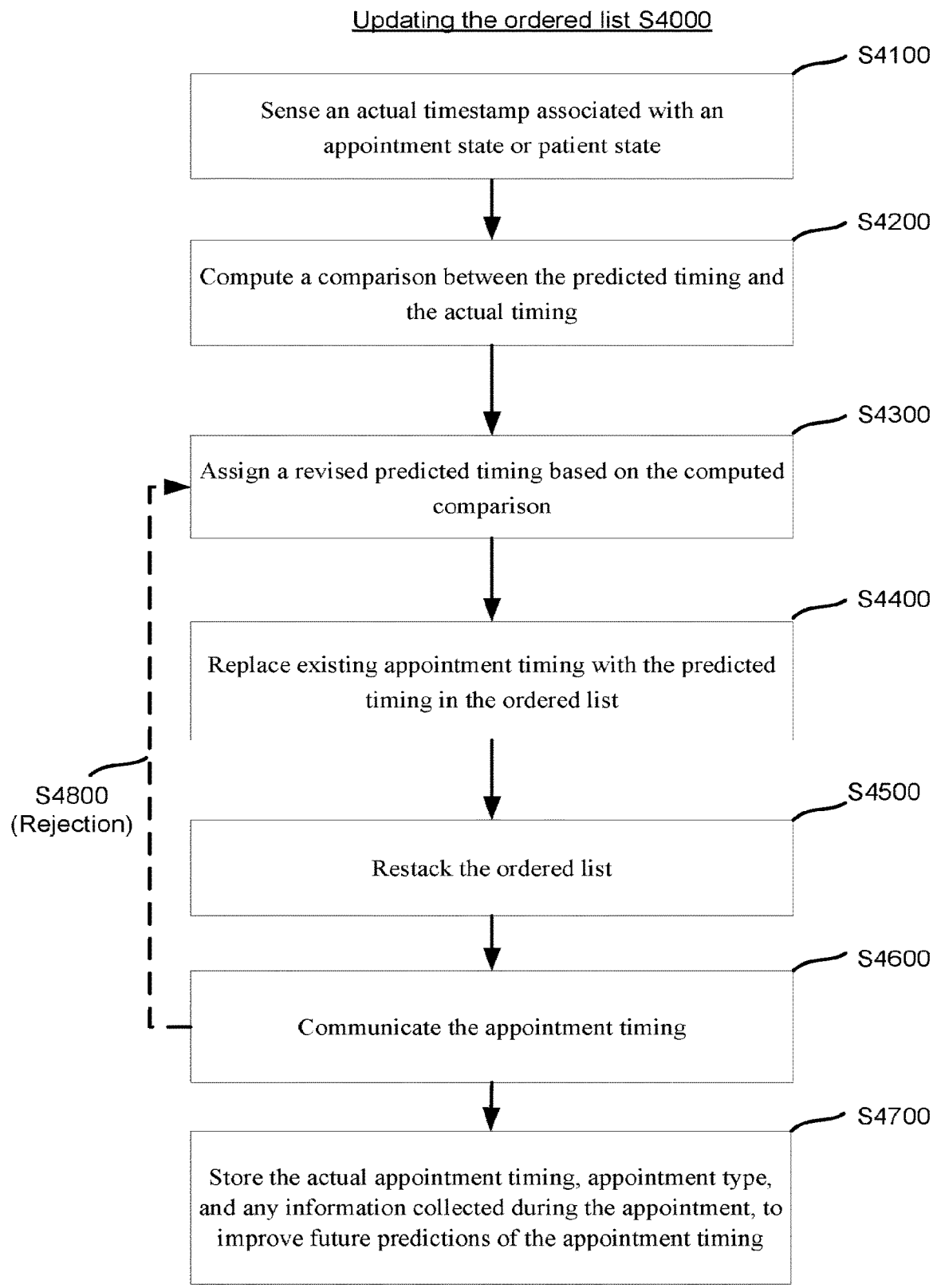
FIG. 4A is a flow diagram illustration of a method for updating the ordered list according to an example.

FIG. 4A is a flow diagram illustration S4000 for updating the ordered list 1110 according to an example. Flow diagram S4000 includes steps to sense an actual timestamp associated with an appointment state or patient state (S4100), to compute a comparison between the predicted timing and actual timing (S4200), to assign a revised predicted timing based on the computed comparison (S4300), to replace the existing appointment timing with the revised predicted timing in the ordered list (S4400), to restack the ordered list (S4500), to notify affected patients of the scheduled time or subsequent change to the appointment timing (S4600), and to store the actual appointment timing, the appointment type, and any information collected during the appointment, to improve future predictions of the appointment timing (S4700).

Step S4100

Step S4100 of sensing the actual timestamp 1320 may be done through several scenarios. The spatial position 1310 and the actual timestamp 1320 are sensed by the one or more sensor systems 1300. In this case the spatial position 1310 is associated with the patient or the communication system 1500 that can provide the patient location 2220. The actual timestamp 1320 and a spatial accuracy factor of the sensor system 1300 associated with the time of the sensed spatial position are also recorded. In another example, the patient can trigger the actual timestamp 1320 by several scenarios as well. In one case, the patient device 1414 can detect the patient location 2220 and determine that the patient is unlikely to be able to make the appointment timing 2100. In this case the prediction value associated with the 'patient check-in' appointment state will be lowered and a communication can be sent to the patient to see if they need to reschedule. In another case the patient can input into the patient device 1414 that they are unlikely to meet the expected appointment time and can provide an amount of expected delay.

FIG. 4B

Figure 4B:
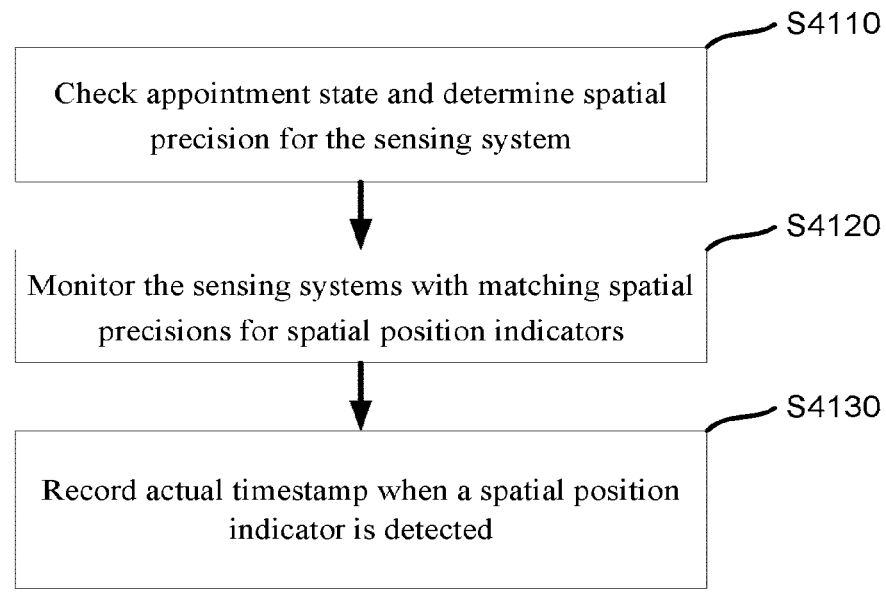
FIG. 4B shows an example of a step of sensing a spatial position and an actual timestamp.

As shown in FIG. 4B, according to one example sensing a spatial position and an actual timestamp S4100 is done by several steps including checking the appointment state and determining the spatial precision needed for the sensing system (S4110), monitoring the sensing systems with matching spatial precisions for spatial position indicators (S4120), and recording the actual timestamp when the spatial position indicator is detected (S4130).

Figure 7A:
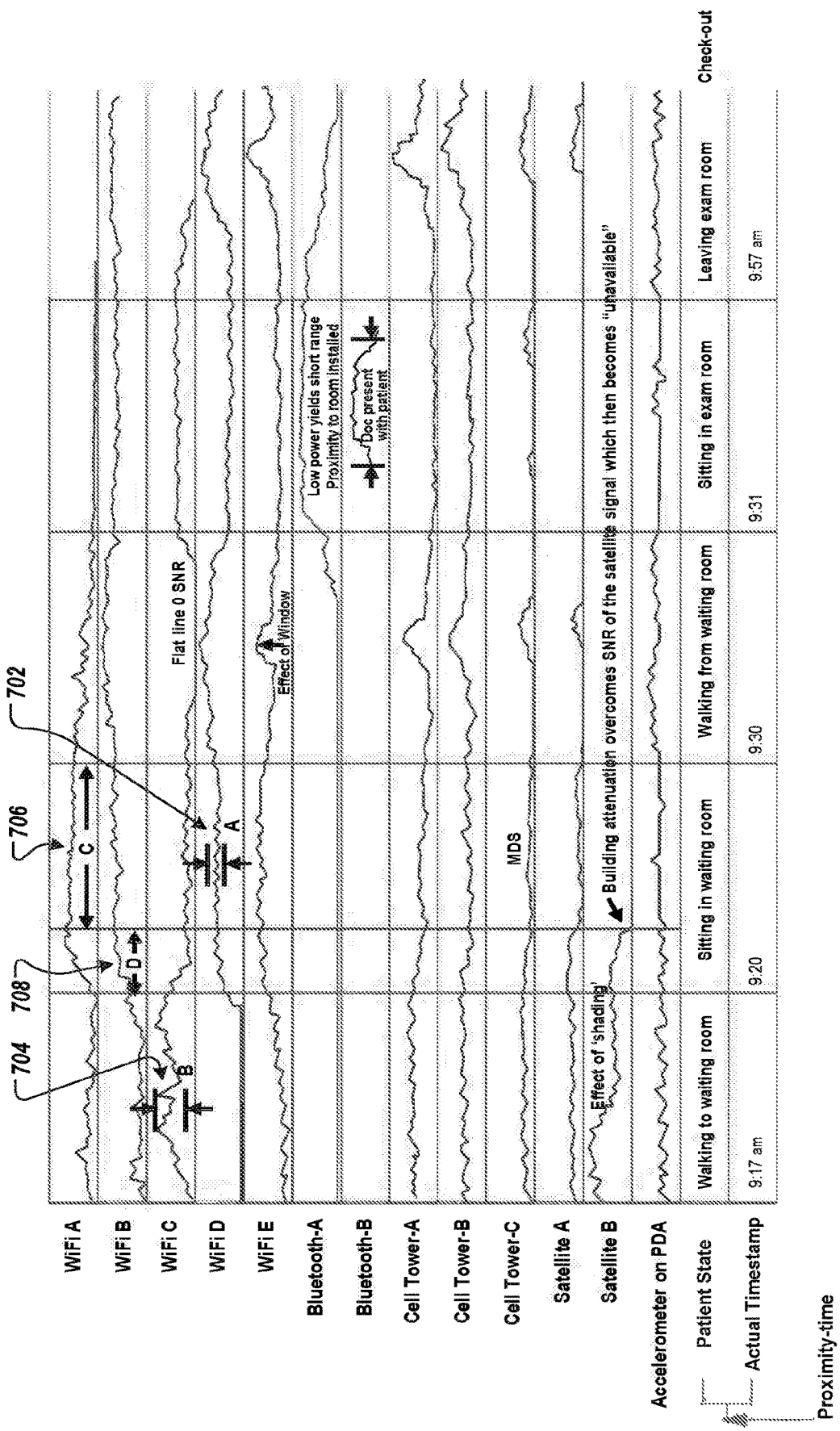
FIG. 7A shows a chart showing examples of the methods to sense a spatial position and an actual timestamp to determine the proximity-time according to an example.

In one example, step S4100 can be done according to the steps described in FIG. 7A. The sensing of the new actual timestamp or the new appointment state is done by comparing the multiple inputs from the one or more sensor systems 1300. The comparison the multiple inputs from the one or more sensor systems 1300 results in the proximity-time or the change in the appointment state. The spatial position 1310 and the actual timestamp 1320 are sensed by the one or more sensor systems 1300. The spatial position 1310 is associated with either the patient or the provider or both. The actual timestamp 1320 and a spatial accuracy factor 1330 of the sensor system associated with the sensed spatial position are also recorded.

Step S4200

Step 4200, computing a comparison between the predicted timing and the actual timing, can be done by several scenarios. In one example, step 4200 includes computing a comparison of the appointment entry component 2000 with the spatial position 1310 and the actual timestamp. Here the appointment entry component 2000 can be the appointment timing 2100 including the estimated appointment time and the set of PAD's. The predicted timing may be one stored in the schedule database 1100 or the archive 1600. The actual timestamp can be generated from the one or more sensor systems 1300.

According to another example, the predicted timing can include any other appointment entry component 2000 such as the prediction value 1140 and the spatial accuracy factor 1330. The comparison may be done using one of simple arithmetic, linear quadratic estimation, a Kalman algorithm, a least squares method, and a multi-fractional order estimator. (See FIG. 7B)

Step S4300

Step S4300 includes a step of assigning a revised predicted timing based on the computed comparison from step S4200. In one example this step includes assigning, based on the computed comparison, one of a revised PAD, a revised appointment timing 2100, a revised prediction value with respect to the appointment entry component, and a revised appointment entry component including the revised respective prediction value. Any revised appointment timing and revised prediction value are assigned to the respective ordered list 1110 in the schedule database 1100. In an example, only a revised prediction value 1140 of the respective appointment entry component 2000 is assigned. In another example, both a revised appointment entry component 2000 and a respective revised prediction value 1140 are assigned. In one example the revised PAD or the revised prediction value can be considered as an appointment adjustment factor.

FIG. 4C

Figure 4C:
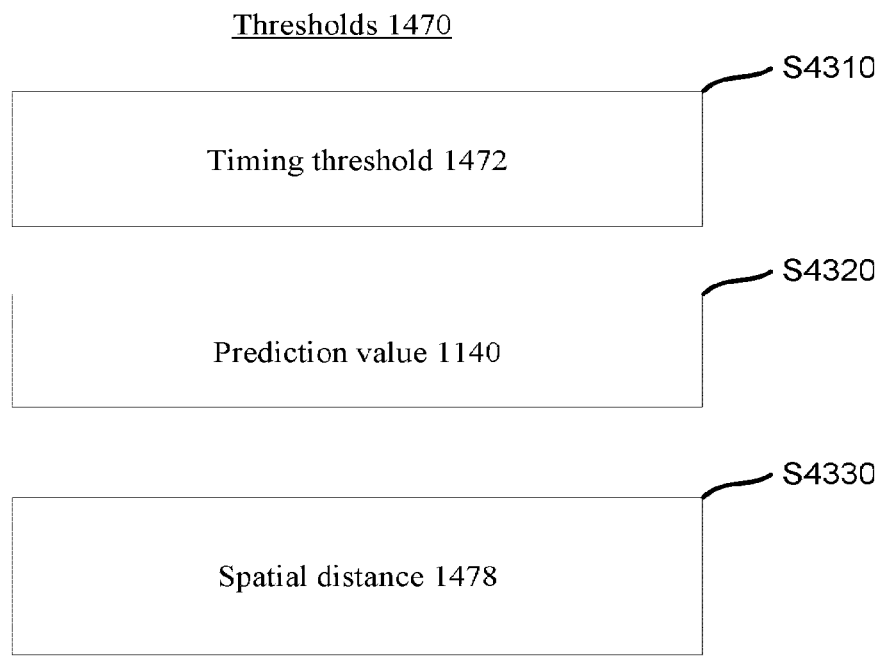
FIG. 4C shows an example of a step of assigning based on the computed comparison including a threshold.

FIG. 4C shows that the step of assigning based on the computed comparison S4300 can be based on a threshold 1470 according to an example. In one scenario the threshold 1470 can be one of a timing criteria or timing threshold 1472, a spatial distance 1474, or the prediction value 1140. The timing threshold 1472 can be a set time, a time duration, or a relative time based on any timer. The spatial distance 1474 threshold can be a set distance or a relative distance based on one of the sensing system 1300, the appointment location 1135, and the patient location 2220. The prediction value 1140 threshold can be a fixed value based on any prediction value associated with any appointment entry component.

In another scenario the threshold 1470 can be a change in one of the timing threshold 1472, the spatial distance 1474, or the prediction value 1140. In another scenario the threshold 1470 is a combination of a set value, a difference, or a combination. In one example, the threshold 1470 can be a combination of any one of the timing threshold 1472, the spatial distance 1474, the prediction value 1140, the timing difference 1476, and the spatial distance difference 1478.

According to an exemplary embodiment, each sensor system 1300 output is ranked by its respective spatial accuracy factor 1330. The output from the highest ranked sensor system 1300 can be selected for further processing.

Step S4400

At step S4400, replacing of the existing predicted timing with the actual timing and new predicted timing in the ordered list is done according to several scenarios. As the appointment day progresses, each PAD is replaced with the respective AAD. At each occurrence of the sensing of an actual timestamp, the ordered list 1110 can be restacked and one or more revised PAD's can be generated to more accurately predict the timing of the remaining schedule.

Step S4500

At step S4500 the ordered list 1110 is modified by using a restacking method. The restacking method modifies the ordered list 1110 in the schedule database 1100 as a result of any of several occurrences. In one case the restacking method modification can shift the appointment timing 2100 for all appointments in the ordered list 1110 up or down by a same amount. In this case, the PAD's are maintained and only the predicted timestamps, such as the estimated start time, are modified. For example, if the provider showed up with a delay, the estimated appointment time for each appointment entry in the ordered list 1110 would be shifted by that delay.

In another case, the restacking method includes modifying one or more of the appointment entries while maintaining the predicted timing for their set of appointment states. In a further case, a set of procedure resources 3000 scheduled can be grouped and shifted or reassigned. In another case, the restacking method can include modifying the ordered list 1110 by each appointment state scheduled, thereby changing the appointment timing and the PAD for one or more appointment entry in the ordered list 1110.

In another case, the restacking method includes modifying the procedure resources 3000 scheduled in the ordered list 1110 to affect the appointment timing for each appointment entry, including any revised appointment timing. In another example, when availability of a procedure resource changes such that appointment entries in more than one ordered list are affected, those appointments and appointment states are restacked accordingly throughout the schedule database 1100.

In one case, the restacking method can be done for future appointments starting from a present time or a time after the next appointment entry in the ordered list where the patient hasn't checked in yet. In one case, an appointment entry in the ordered list 1110 can include a null name to force a break the schedule. An average PAD time can be used for the appointment timing for the appointment entry associated with the null name until the break is filled with an actual patient. The provider can fill in the break with any of the one or more patients in the ordered list 1110. An available appointment entry for the break can be added in the ordered list to approximate a lunch time for the provider.

In one example, the patient is sent a notification of the revised appointment timing and is optionally given a choice to accept, to reject, and/or to request an alternative appointment time/day.

Examples of events and triggering the restacking method include:

1) A first patient 'checks out' at the end of their respective appointment, which in turn indicates the availability the respective exam room for the subsequent patient. The check-out of the first patient is done by one of several ways. The compute step S4200 indicates that the patient has entered the check-out appointment state. The provider or office staff can generate the discrete signal 1340 by manually entering into the stationary device 1420 or the mobile device 1410 that the respective patient's appointment is complete. Alternatively, the first patient can indicate the appointment is complete via a computer or mobile app or by sending a text message.

2) A patient's GPS coordinates or information that is known from location services on their cell phone indicate that they have left the provider's office and therefore the appointment is complete.

3) If the provider is late at the beginning of the day, a new start time is assigned and the day's appointments are restacked accordingly. Likewise, if the provider is late upon their return from lunch the following appointments are restacked accordingly.

4) When a patient is late to the appointment location 1135 this can also cause the system to restack appointments.

5) When a patient does not check-in within a certain period of time, a restack occurs to shift the remaining appointments earlier.

6) The patient's GPS coordinates indicates that the patient will not be able to make the appointment on time.

7) An unscheduled patient can be added into the ordered list 1110 for emergency reasons or other reasons, causing the following appointments to restack accordingly.

8) The provider takes a break such as for lunch or another reason.

9) Occurrence of a storm, power failure, or equipment failure causing the scheduled appointments to restack and possibly be canceled.

10) The provider or the provider's staff learns that an appointment will take longer than the PAD and therefore updates the PAD. The updated PAD causes a restack of the scheduled appointments.

Step S4600

At step S4600 a communication or notification is sent regarding the appointment timing. In one example the one or more patients that are affected by the schedule changes are notified of the modified appointment timing and have an opportunity to accept, reject, and/or request alternative appointment timing. In one example, the communication system 1500 or other scheduling system 1000 component transmits a communication or notification over the network 1200 to activate the mobile app on the mobile device 1410, which causes the notification to display on the mobile device 1410 and enables connection of the mobile device 1410 to the scheduling system 1000 when the mobile device 1410 is in communication with the network 1200. In one example, the notification is a button to accept or to reject the revised appointment timing. When the revised appointment timing is rejected the next closest appointment timing can be offered or the patient can be offered to request a new appointment timing. In one example, the patient making the new appointment timing request based on the revised appointment timing can be considered a "VIP patient". In another example, the one or more probability values corresponding to the appointment timing is also sent. The notification of the modified appointment timing for each appointment is sent to only to each associated patient with their appointment timing modified. Here, the mobile device 1410 can be either the patient device 1414 or the provider device 1412, allowing either to send a response to the revised appointment timing.

Step S4700

At step S4700 the appointment entry components with their respective actual durations and their wait times are entered into the archive 1600. In another example, a set of analytics comparing differences between the set of AADs and the set of PADs can also be calculated and saved in the archive 1600 to improve prediction of the appointment timing 2100 for future appointments in this step. Here the AAD represents the final timing for each actual time duration for the appointment, including the appointment states. In one example, the AAD can include one or more of the patient status or the patient state timing, the provider status or the provider state timing, and the set of procedure resource timing to determine the total wait time the patient experiences and efficiency of the providers.

In one case, the step of updating the archive with the actual duration includes revising the appointment entry component 2000, the archived timing 1620, and the respective prediction value 1140 according to the actual timestamp 1320. The archived timing 1620 is the average duration for the associated timing. In another example, the one or more appointment entry components 2000 and the respective prediction value 1140 in the archive 1600 are updated according to a calculation between the archived timing 1620 and the actual timestamp 1320 from the sensor system 1300. The calculation may be one of an average, and a multiplication factor including a standard deviation of the average. The updated timing duration from the actual timestamps recorded in the archive 1600 are associated with the appointment type 1133 and other information collected during the appointment to improve future predictions of appointment timing 2100.

Step S4800

According to one example, the process includes a step S4800 (Rejection) after step S4600 where the restacked ordered list from step S4500 is approved or rejected. When the restacked ordered list 1110 is rejected, the process is repeated at step S4300. Rejection of the restacked ordered list can be done by the provider and/or the patient.

FIG. 4D

Figure 4D:
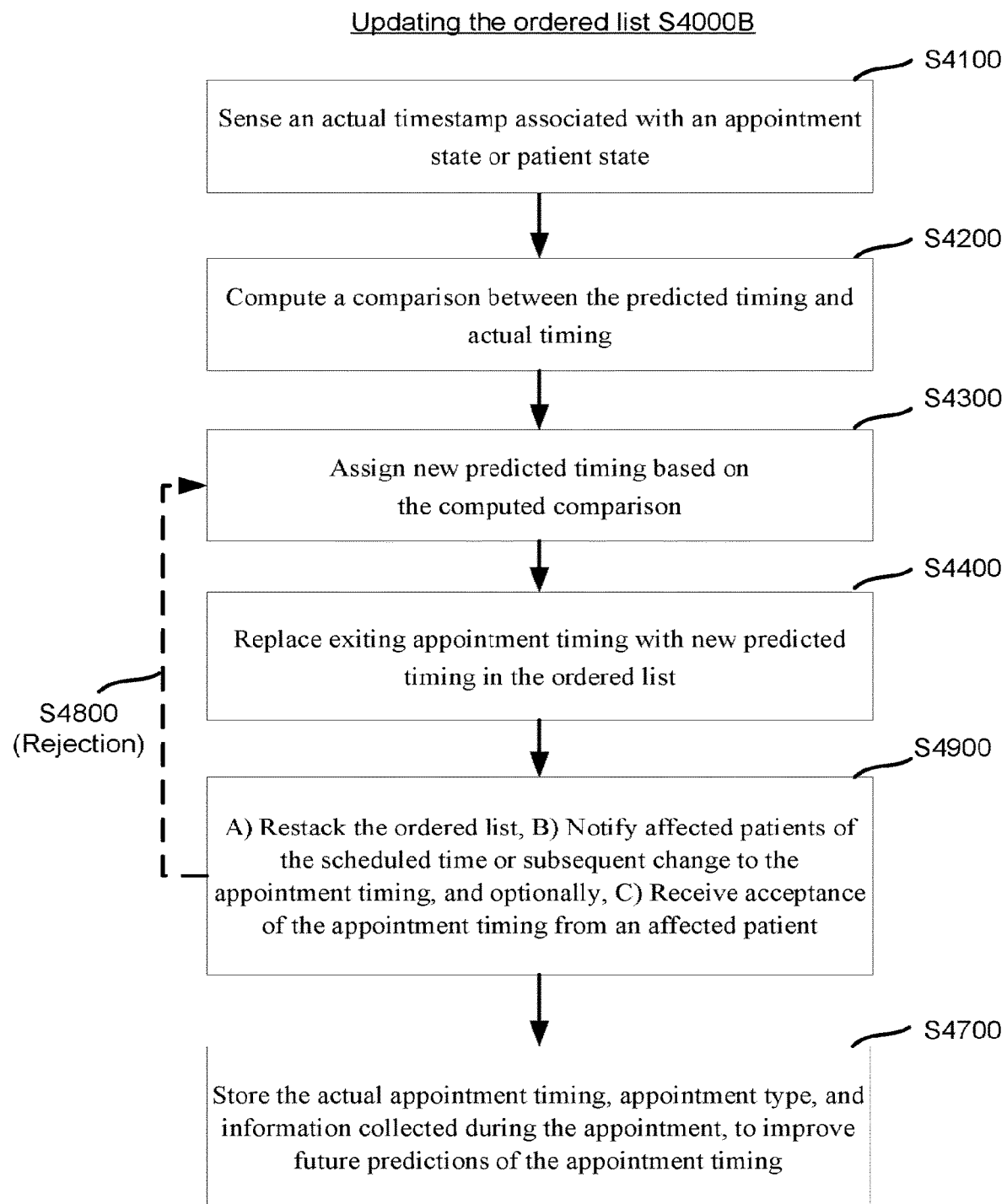
FIG. 4D is a flow diagram illustration of a method for updating the ordered list according to another example.

FIG. 4D shows flow diagram illustration S4000B, which is another example of the flow diagram illustration S4000 for updating the ordered list. Flow diagram S4000B replaces steps S4500 and S4600 of FIG. 4A with step S4900.

Step S4900

Step S4900 includes steps of A) Restacking the ordered list, B) Notifying the affected patients of the estimated appointment time or the revised appointment timing 2100, and optionally, C) Receiving acceptance of the appointment timing 2100 from an affected patient. The communication of the acceptance of the revised appointment timing 2100 by the affected patient can be done in several ways. In one example, the affected patient can communicate directly to the provider or the provider staff. In another example, the affected patient can enter an input into the patient device 1414.

In one example, receiving acceptance from the affected patient can be receiving an affirmative response. In another example, receiving acceptance from the affected patient can be done by the communication system 1500 or by the processing circuitry 1400 receiving a confirmation that the communication was delivered and a rejection response was not returned. In this case, there can be a time limit set and a response timer for the patient to input their response. After the response timer exceeds the time limit the patient's response will be considered as an acceptance. In case the patient rejects the revised appointment timing 2100, the step S4800 is initiated to repeat step S4300.

FIG. 4E

Figure 4E:
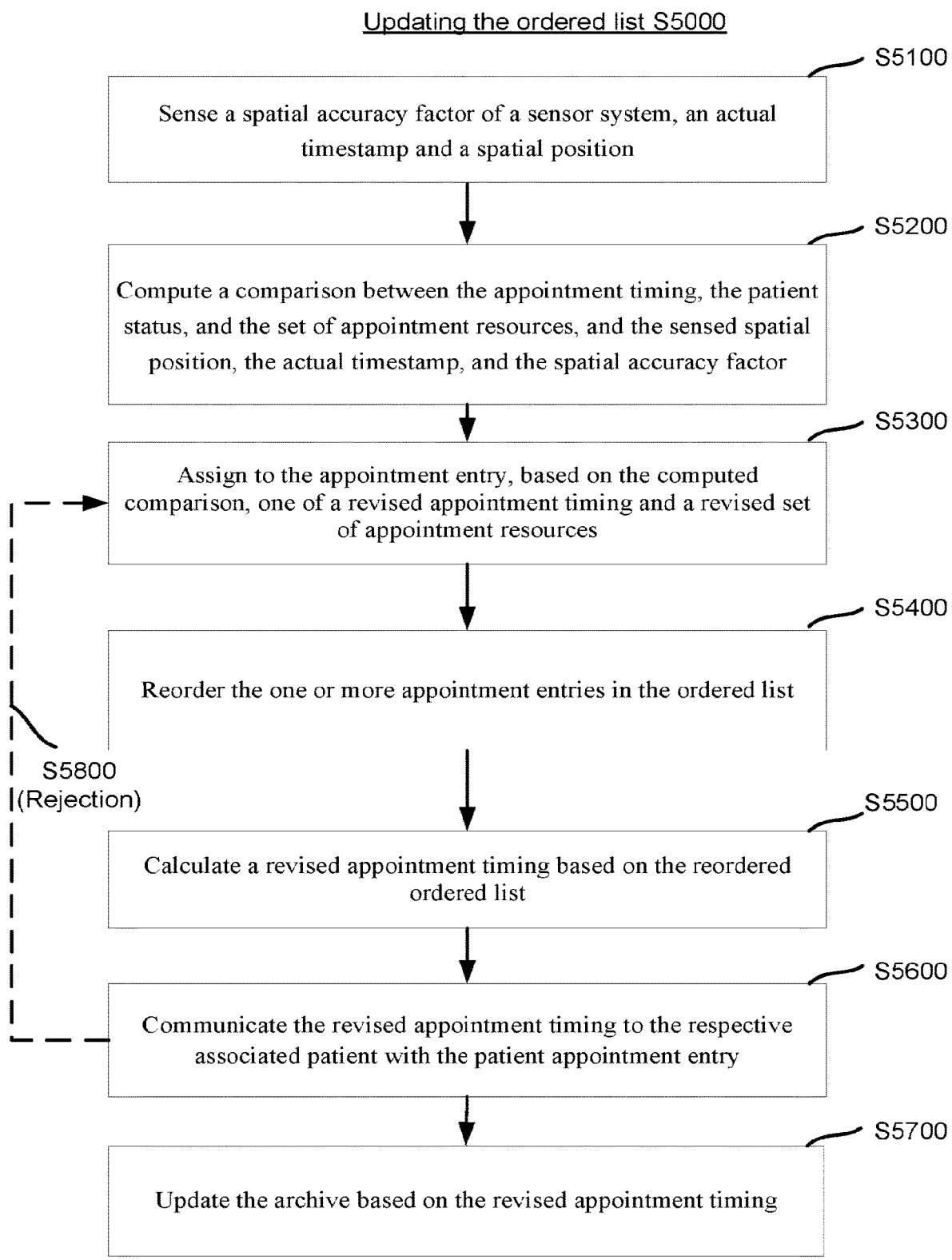
FIG. 4E is a flow diagram illustration of a method for updating the ordered list according to another example.

FIG. 4E is a flow diagram illustration for updating the ordered list according to another example (S5000). At step S5100, sense a spatial accuracy factor of a sensor system, an actual timestamp and a spatial position. At step S5200, compute a comparison between the appointment timing, the patient status, and the set of appointment resources, and the sensed spatial position, the actual timestamp, and the spatial accuracy factor. At step S5300, assign to the appointment entry, based on the computed comparison, one of a revised appointment timing and a revised set of appointment resources. At step S5400, reorder the one or more appointment entries in the ordered list. At step S5500, calculate a revised appointment timing based on the reordered ordered list. At step S5600, communicate the revised appointment timing to the respective associated patient with the patient appointment entry. At step S5700, update the archive based on the revised appointment timing. In case the patient rejects the revised appointment timing 2100, the step S5800 is initiated to repeat step S5300.

FIG. 5

Figure 5:
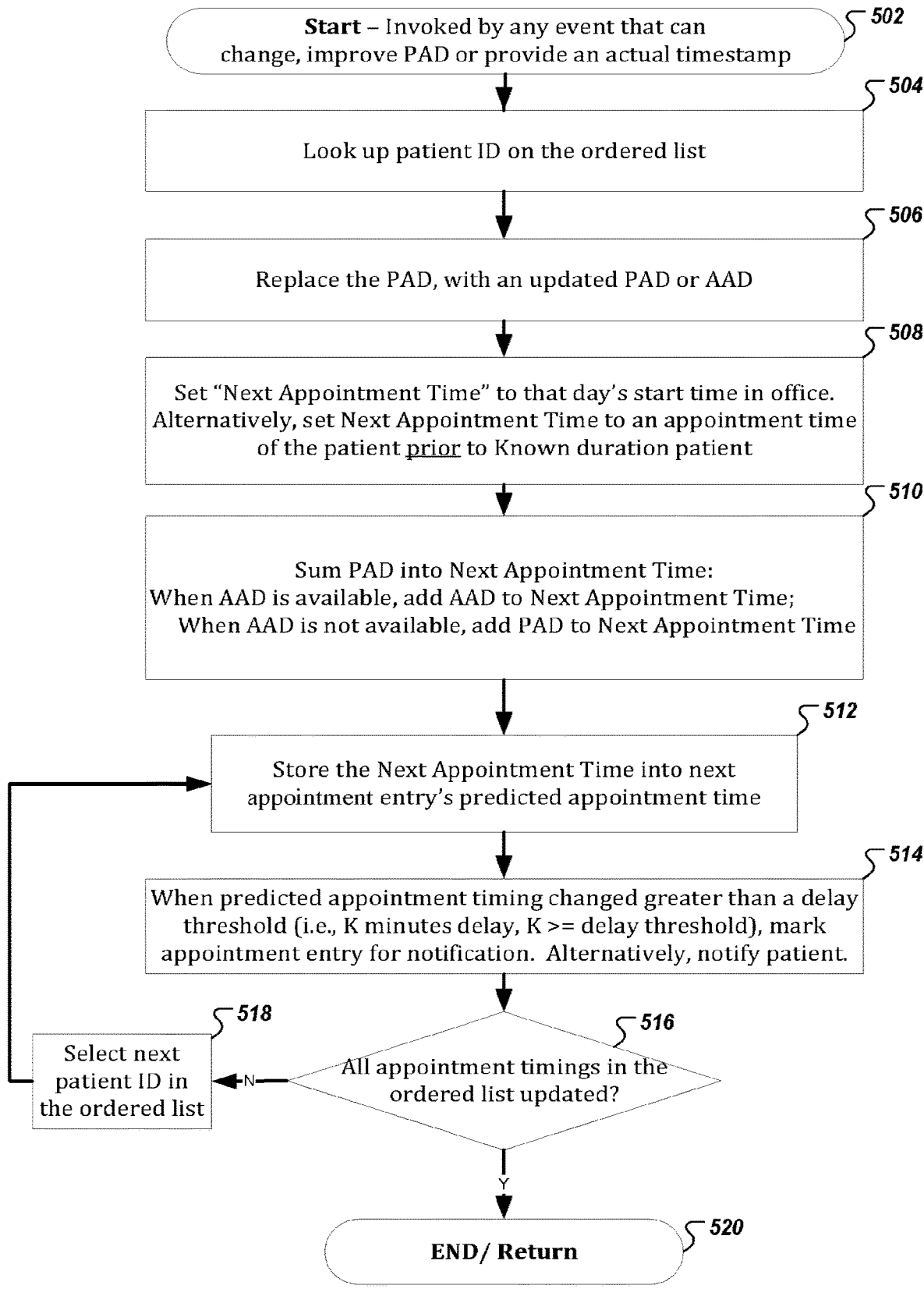
FIG. 5 shows a flowchart of a method for updating each appointment entry in the ordered list according to an example.

FIG. 5 shows a flowchart of a method 500 for updating each appointment entry in the ordered list 1110 according to an example. At step 502, the method 500 can be invoked by any event that can change, improve the PAD or provide an actual timestamp. At step 504, look up a patient ID on the ordered list 1110. At step 506, replace the PAD with an updated PAD or AAD. At step 508, set "Next Appointment Time" that day's start time in office. Alternatively, set Next Appointment Time to an appointment time prior to an appointment entry having a known duration. At step 510, sum the PAD into the Next Appointment Time. When the AAD is available, add the AAD to the Next Appointment Time. When the AAD is not available, add the PAD to the Next Appointment Time. At step 512, store the Next Appointment Time into the next appointment entry's predicted appointment time. At step 514, when the predicted appointment timing changed greater than a delay threshold (i.e., K minutes delay, K>=delay threshold), mark the appointment entry for notification. Alternatively, notify patient associated with the appointment entry. At step 516, check if all appointment timings in the ordered list updated. When all appointment timings in the ordered list are updated (YES), proceed to step 520 and end. When all appointment timings in the ordered list are not updated (NO), proceed to step 518. At step 518, select a next patient ID in the ordered list.

FIG. 6

Figure 6:
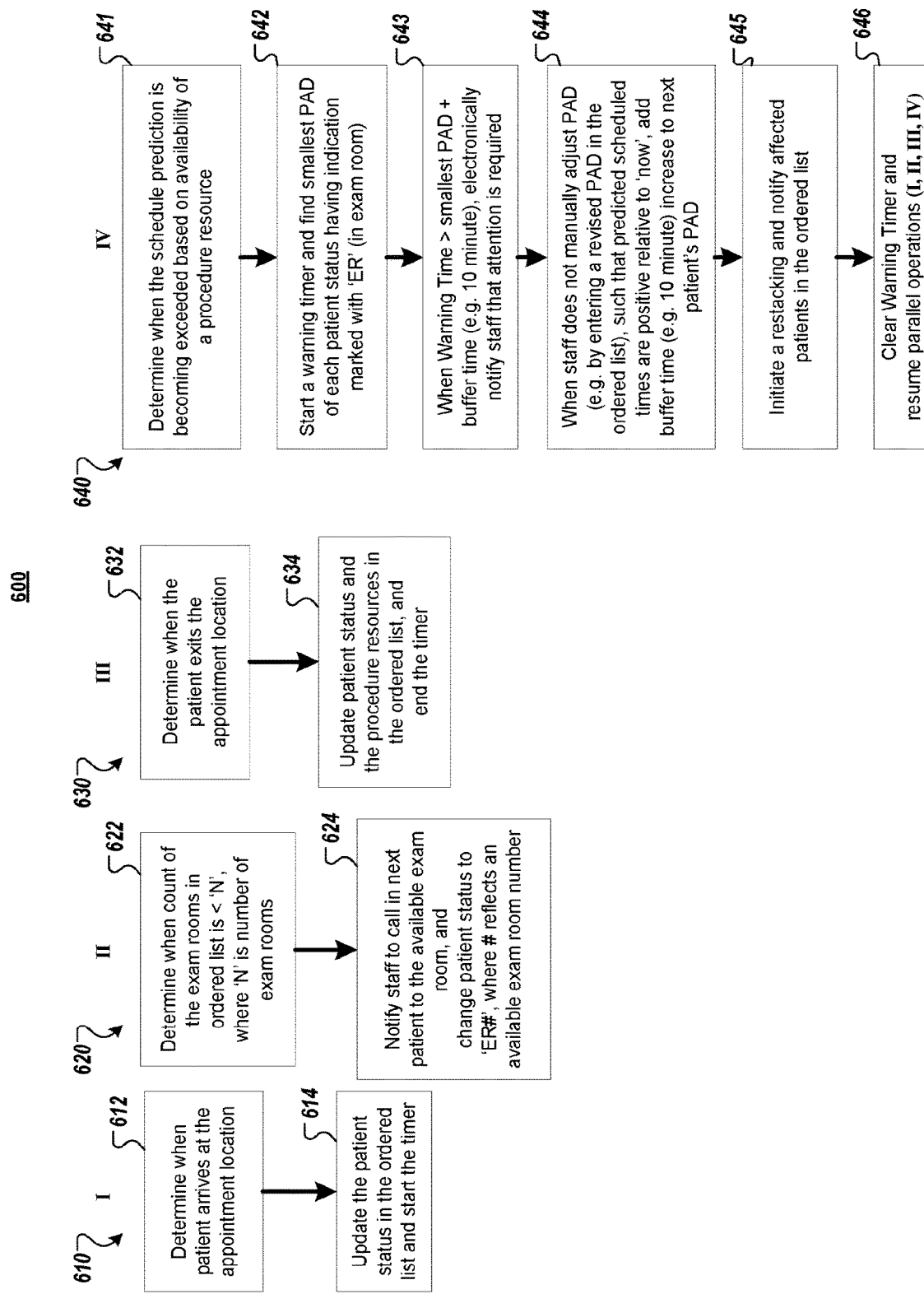
FIG. 6 shows an algorithm for coordinating the procedure resources and the ordered list according to an example.

FIG. 6 shows an algorithm 600 for coordinating the procedure resources 3000 and the ordered list 1110 according to an example. In an example, the algorithm 600 includes parallel operations 610-640 configured to maintain each row in the ordered list with the patient status and timer.

In an example, the operation 610 (I) is triggered when a determination is made that patient arrives at the appointment location (612). The operation 610 includes updating the patient status in the ordered list 1110 and starting the timer (614).

In an example, the operation 620 (II) is triggered when a determination is made that a count of the exam rooms in ordered list is <'N', where 'N' is number of exam rooms (622). The operation 620 subsequently includes steps of notifying the staff to call in next patient to the available exam room, and changing the patient status to 'ER #', where # reflects an available exam room number (624).

In an example, the operation 630 (III) is triggered when a determination is made that the patient exits the appointment location (632). The operation 630 includes steps of updating the patient status and the procedure resources in the ordered list, and ending the timer (634).

In an example, the operation 640 (IV) is triggered when a determination is made that the schedule prediction is becoming exceeded based on availability of a procedure resource patient arrives at the appointment location (641). When the step 641 is met, the operation 640 starts a warning timer and finds a smallest PAD of each patient status having indication marked with 'ER' (in exam room) (642). At step 643, when the Warning Time>smallest PAD+buffer time (e.g. 10 minute), the staff is electronically notified that attention is required. At step 644, when the staff does not manually adjust the PAD (e.g. by entering a revised PAD in the ordered list), such that predicted scheduled times are positive relative to 'now', a buffer time (e.g. 10 minute) is added to the next patient's PAD. At step 645, a restacking is initiated and a notification is sent to affected patients in the ordered list. At step, 646, the Warning Timer is cleared and the parallel operations 610-640 (I, II, III, IV) are resumed.

FIGS. 7A-11C

FIG. 7A-FIG. 11C show different scenarios where the different types of the sensing systems 1300 result in different precision of the proximity-time.

FIG. 7A

FIG. 7A shows a chart 700 showing examples of the methods to sense a spatial position and an actual timestamp to determine the proximity-time. Multiple data-streams are shown from different types of sensor systems 1300 in each row of the chart shown. The patient state 2210 can be determined from comparing one or more of the data-streams to identify the patient location 2220. The proximity-time is a combination of the patient state 2210 and the respective actual timestamp. In another example, the proximity-time can also be a combination of the provider state and the respective actual timestamp.

The comparison of the one or more of the data-streams to identify the patient location 2220 can be done in several ways. Several indicators 702-708 are shown on the chart that can be used to identify a marker in the data-stream or signal which can provide information to determine the proximity-time. Sensing of an indicator 702-708 can be used to trigger an update of the appointment state or the patient state, start or stop any timer, and/or initiate a different sensor system to turn on/off or modify the sensitivity to one or more other sensor systems. In an example, a marker can be based on a relative variation to a threshold of the signal strength 1350 in different ranges between −100 dB to 0 dB. In an example, a signal strength 1350 of −50 dB can be considered a sufficient signal to indicate an indicator 702-708 has been met.

Indicator 702 (A) shows the expected variance of the signal strength 1350 of 10-20 dB due to signal fading. Indicator 704 (B) shows variation of the signal strength 1350 due to shading from signal attenuation (e.g. buildings, parking garages, etc.), particularly large effect on satellites near horizon. Indicator 706 (C) shows an example of the patient's device 1414 sensing a stationary WiFi signal after check-in. In an example, the sensing of indicator 706 (C) can be configured to trigger an update in the appointment state and start the timer. Indicator 708 (D) shows a signal change caused by attenuation of entering/exiting a room according to an example.

In one example, multiple WiFi signals are present and are used to determine proximity-times without requiring actually access to the network 1200. Signal WiFi-A shows an example of a signal coming from a mobile device 1410 in a waiting room. Signal WiFi-B shows an example of a signal coming from a general doctor's office, which is not part of the system. Signal WiFi-C shows an example of a signal coming from an unrelated third party on the way to the provider's office. Signal WiFi-D shows an example of a signal coming from a source inside the building of the provider's office. Signal WiFi-E shows an example of a signal coming from a higher floor than the present floor.

In an example, Bluetooth signals are used as stationary locations as well as mobile locations. Signal Bluetooth-A shows an example of a Bluetooth signal emitted by the stationary device 1420 within the exam room. Signal Bluetooth-B shows an example of a Bluetooth signal emitted by the provider device 1412 and sensed by the patient's device 1414. In addition, other procedure resources 3000 may be equipped and tracked with short range sensors for determining the proximity-time corresponding with those resources.

A time-of-flight radio location becomes highly inaccurate in buildings due to severe changes in multi-path environment, resulting from small changes in the signal strength 1350 distance. Therefore, valid (CRC/Error Validation) messages may be more predictable such as using multiple 'channels' if independent information improves prediction.

In an example, the comparison of the one or more of the data-streams to identify the patient location 2220 can be done using different types of data. For example, a data-stream from an accelerometer or gyroscope in the patient device can be used to indicate that the patient is walking. In this case, as the patient walks from the waiting room to an assigned exam room, the data-stream from the one or more beacons can be ignored until the data-stream from the accelerometer or gyroscope rests for a period of time. This data source preference can be configured to prevent from the patient location 2220 being incorrectly assigned to other locations detected along the pathway.

Patient Proximity-Time

The patient proximity-time can be provided by any combination of the scenarios below, each of which can have variant accuracy and availability to the provider and the patient.

a. The provider device can have an identification code matching that of the sensor system 1300. For example, the identification code can be a 5 digit/character/alphanumeric identification code that matches a wireless portal.

b. The provider or the office staff can manually enter the patient state into the provider device 1412 or the stationary device by clicking a button. The provider can enter a completion code on their computer, office computer, the provider device or their cell phone.

c. Completion of an accounting task registers completion of the patient visit, indicating that the patient is out of the exam room, in the waiting room, or is leaving the office.

d. The patient themselves click a completion button on the patient device or by sending a text message, email, phone call, voicemail.

e. The mobile device can have an optical emitter and reader to detect when the patient is in the appointment location and when they leave.

f. The stationary device, the provider device, or the appointment location can have an associated barcode that the patient device reads. The associated barcode can be a physical barcode that is attached or a digital barcode on a display of the mobile device or the stationary device. The provider or the patient can take a picture of the associated barcode upon arrival/completion.

g. The sensor system 1300 detects when the patient device joins the network 1200 (e.g. WiFi) having an associated appointment location.

h. The sensor system 1300 detects the patient by video or camera recognition.

i. The sensor system 1300 detects the patient by audio recognition.

j. When the mobile app is active on the patient device, an accelerometer in the patient device can be configured to track a number of steps and to estimate a distance the patient walked in correlation with the appointment locations.

k. When the mobile app is active on the patient device, the patient device can be configured to track the signal strength of the Bluetooth signal in correlation with the provider device, the stationary device, or any procedure resource tag.

l. When the mobile app is active on the patient device, an GPS feature in the patient device tracks the patient location in correlation with the appointment location.

m. The sensor system 1300 detects the patient by an eye scanner at an appointment location.

n. A user interface action such as the patient pressing a soft button on the patient device 1414 (e.g. an iPhone) denoting that the patient has reached the exam room or is checking-in or checking-out.

o. The estimated appointment time and the PAD can be used to predict when the patient leaves. In this case the PAD will be continuously updated so the respective prediction value of the appointment timing for the completion of the appointment will be very high.

p. The sensor system 1300 detects the patient using a fingerprint sensor at an appointment location, where the fingerprint sensor is a separate verification system.

q. Additional examples for estimation of the completion of the appointment are shown in Table 1 above.

The patient proximity-time provides multiple enhancements. Knowing the time when the patient arrives or leaves the provider's office will enable a future prediction of the PAD to be improved. Knowing the time the patients arrives at the provider's office allows the scheduling system to later improve the future prediction based on how long the patient waited in the office.

The patient proximity-time can also provide a distance in time between the patient's location and the provider's office at any given time. The distance in time can provide information to the provider to help make a decision on canceling an appointment or to communicate to the patient that they will be a delay, when the distance in time results in an inconvenient appointment timing. The cancelation or communication can be done immediately or done when a threshold is met based on the distance in time.

FIG. 7B

Figure 7B:
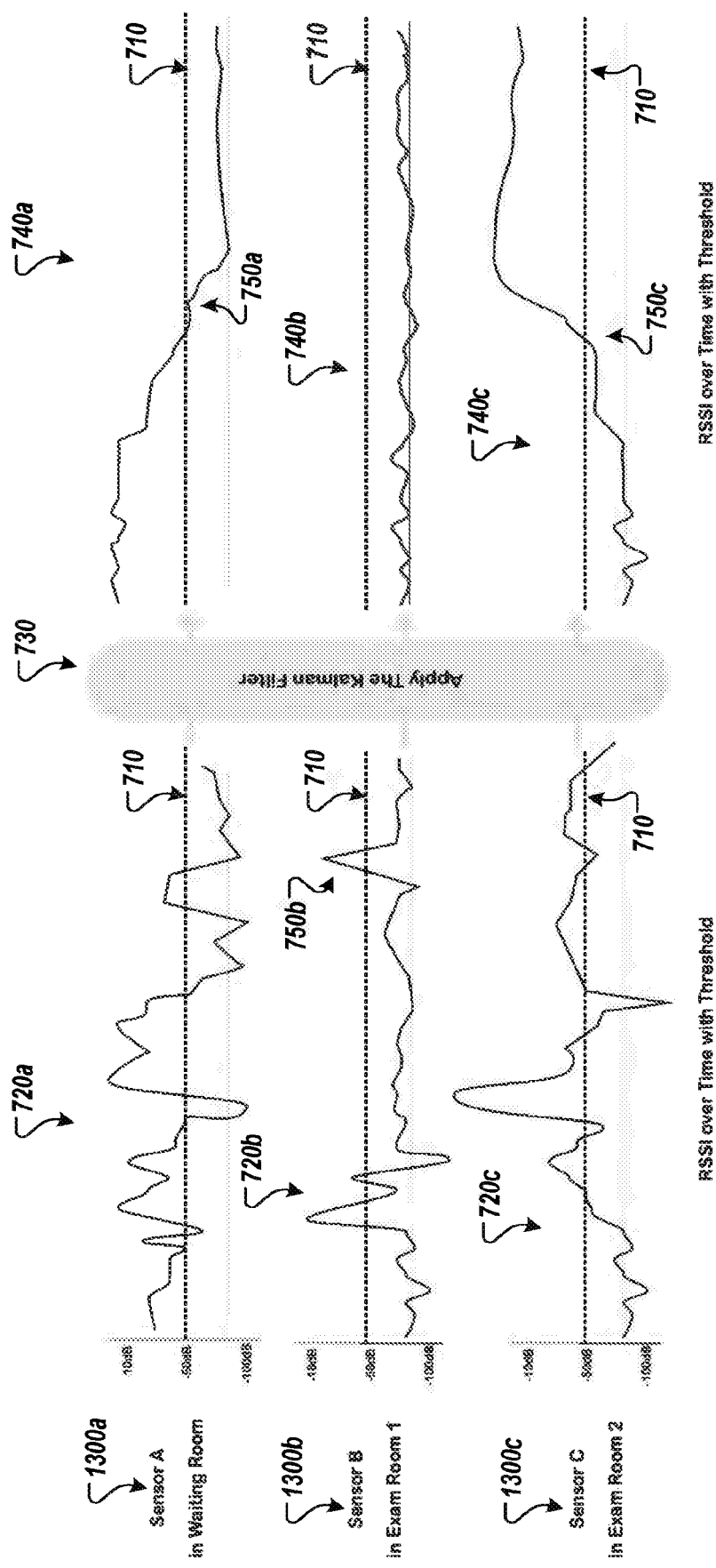
FIG. 7B shows a Kalman filter comparing multiple data-streams from different types of sensor systems according to an example.

FIG. 7B shows a Kalman filter (i.e. processing circuitry applying a Kalman algorithm) comparing multiple data-streams from different types of sensor systems 1300 according to an example. In the example shown, a patient device was detected by three sensor systems 1300*a-c*, each which produced a raw data-stream 720*a-c*, (i.e., received signal strength indicator (RSSI) is a measurement of the power present in a received radio signal, respectively. After applying the Kalman filter (730) with a detection threshold 710 (e.g., 50 dB), each raw data-stream 720*a-c* was modified to a filtered data-stream 740*a-c* respectively.

The data-streams are representative of the patient being initially in the waiting room, then moving past an exam room #1, and arriving at an exam room #2. The Kalman filter is configured to ignore instances where the sensor system 1330*b* was above the detection threshold 710. In an example, the Kalman filter can be configured to ignore input based a time delay (e.g., duration of exposure to a sensor system) and a data type of another sensor system such as accelerometer data to increase accuracy of detecting false positives.

Other filters can be used as well as machine learning for observing trends.

FIG. 8

Figure 8:
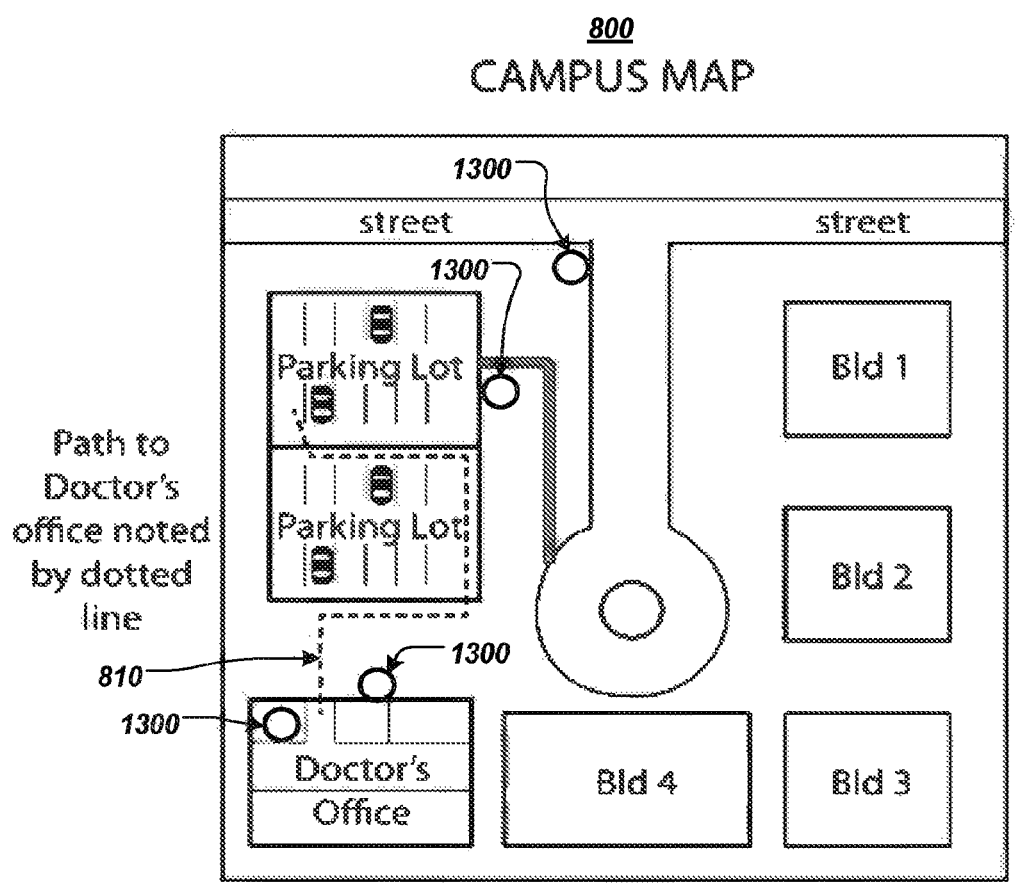
FIG. 8 shows an example of a campus map indicating a pathway to the provider's office from a location on the campus map according to an example.

FIG. 8 shows an example of a campus map 800 indicating a pathway 810 to the provider's office from a location on the campus map 800. In this example, the distance of the pathway can be used to estimate the time of travel from a parking and drop off area to the waiting room. In one example, one or more sensor systems 1300 can be placed along the campus to aid in providing navigation directions to direct the patient to the office, the waiting room, or any other appointment location including a closest pharmacy.

FIG. 9A-9B

FIG. 9A shows an example of a provider office layout with only one level. The waiting room, five exam rooms, and a procedure room are shown separates by a hallway.

FIG. 9B shows an example of a provider office layout with multiple levels. The waiting room, five exam rooms, and a first procedure room are shown on one level, and a second procedure room, a lab, and a pharmacy are shown on a separate level. The office with multiple levels indicates an example where a sensing system 1300 only having only one sensing type, such as GPS, cannot accurately determine the spatial position.

FIG. 10A

Figure 10A:
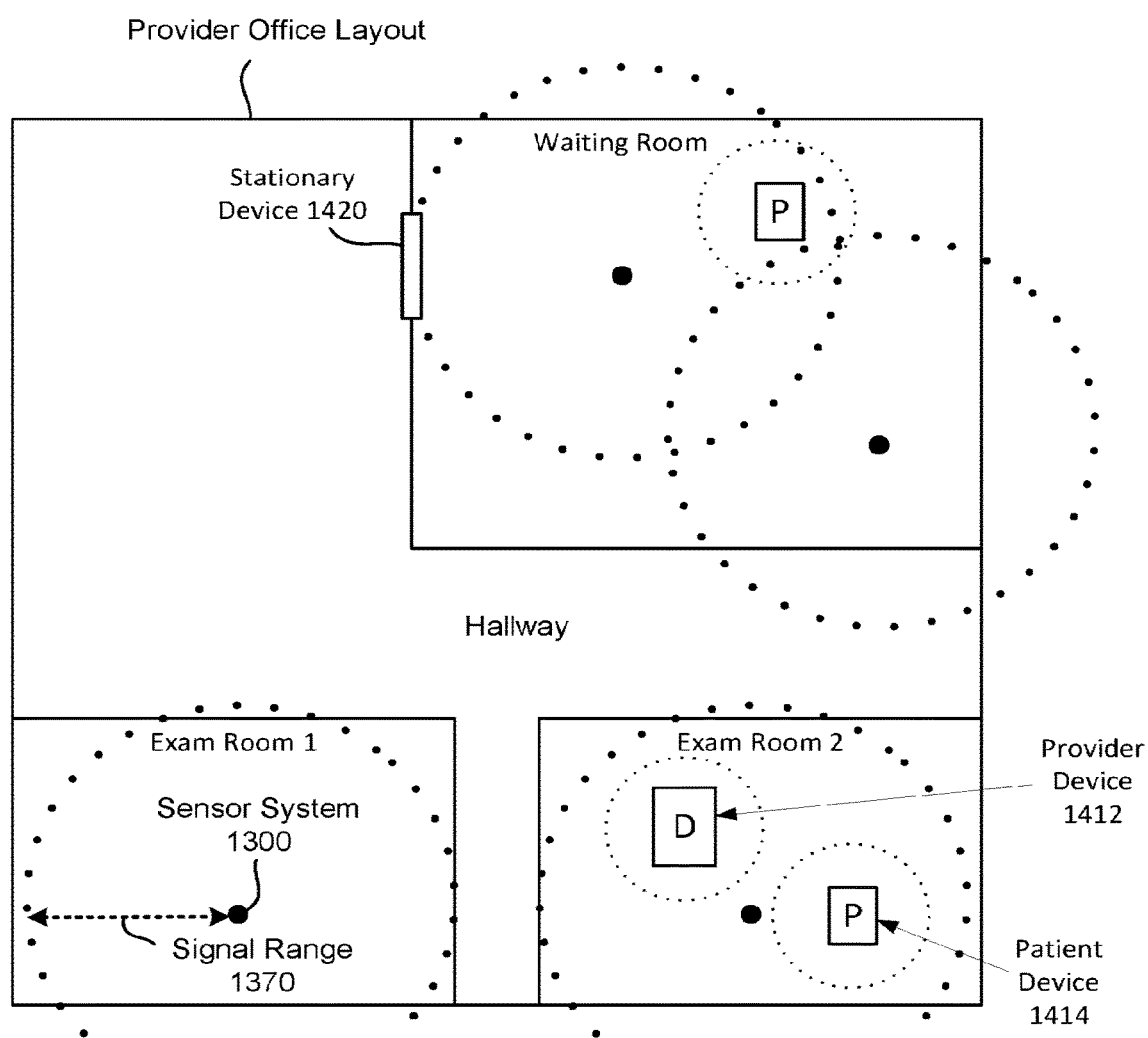
FIG. 10A shows a provider's office layout including the provider device, the patient device, the stationary device, and a sensor system having a signal range according to an example.

FIG. 10A shows another example of the provider's office layout including the provider device 1412, the patient device 1414, the stationary device 1420, and a sensor system 1300 having a signal range 1370. In this example the provider office is shown having a waiting room and at least two exam rooms and the signal range 1370 for each stationary device 1420 and each mobile device 1410 is shown as a symmetrical circle. According to another example, the signal range 1370 can be differently shaped. In this example the two exam rooms are separated by a hallway and the signal ranges 1370 for each respective sensor system 1300 assigned to each exam room are shown to not overlap.

FIG. 10B

Figure 10B:
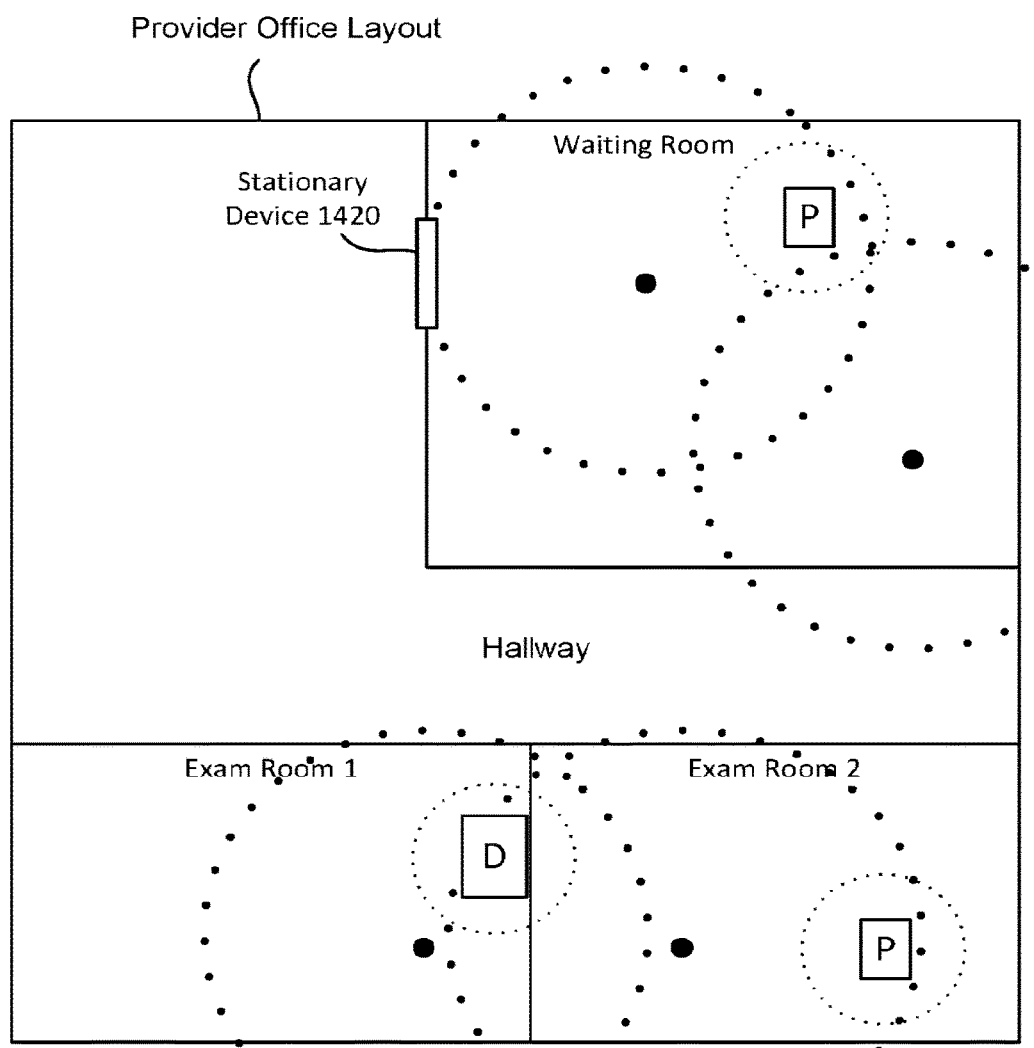
FIG. 10B shows an alternative arrangement of elements in FIG. 10A where two exam rooms share a boundary, the signal ranges for each respective sensor systems assigned to each exam room are shown to overlap, as well as a signal range of the provider device according to an example.

FIG. 10B shows an alternative arrangement of the elements in FIG. 10A where the two exam rooms share a boundary, the signal ranges 1370 for each respective sensor systems 1300 assigned to each exam room are shown to overlap, as well as the signal range 1370 of the provider device 1412. In this example, unless a second sensor system or a signal comparison method is used to differentiate the location of the provider associated with the provider device 1412, the scheduling system 1000 may incorrectly identify the spatial position 1310 of the provider.

FIG. 11A

Figure 11A:
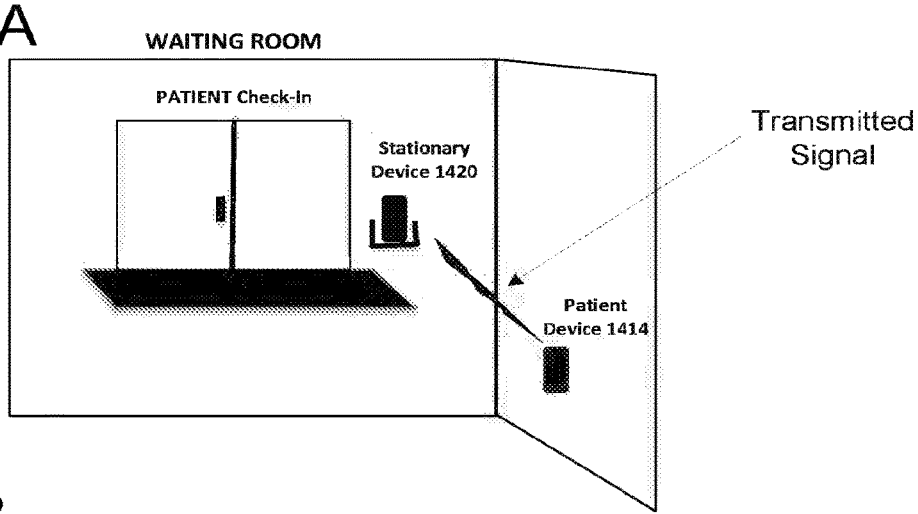
FIG. 11A shows an example of the scheduling system for detecting when the patient arrives at the provider's office, the appointment location, or the waiting room, thereby checking-in according to an example.

FIG. 11A shows an example of the scheduling system 1000 for detecting when the patient arrives at the provider's office, the appointment location 1135, or the waiting room, thereby checking-in. The patient device 1414 is shown communicating with the stationary device 1420 assigned to the waiting room. In an alternative example, the office staff can generate the discrete signal 1340 by manually entering into the scheduling system 1000 that the patient has arrived to the waiting room. In one example, after check-in, the patient device 1414 characterizes the signal strength 1350 from multiple WiFi systems, regardless of who operates them. Then, the patient device 1414 can detect when one or more of their signal strengths 1350 change due to movement.

FIG. 11B

Figure 11B:
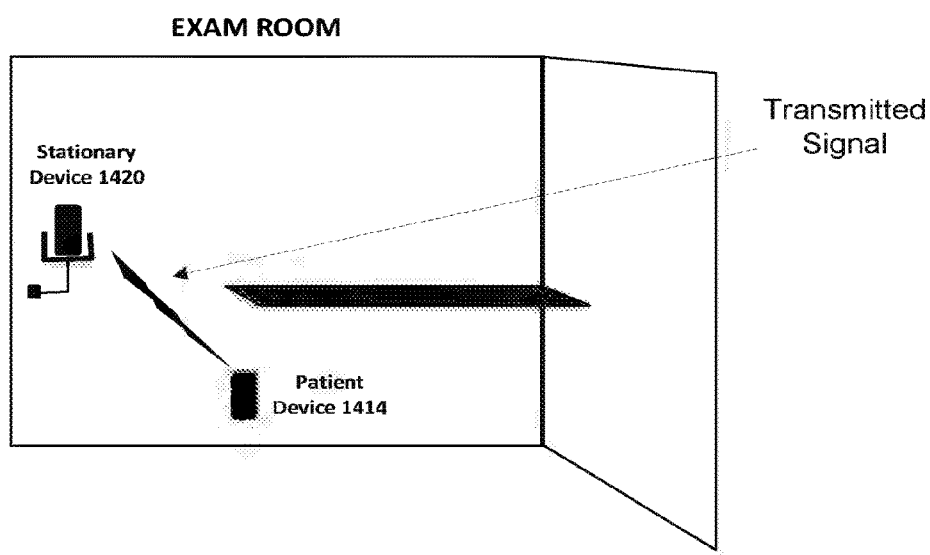
FIG. 11B shows an example of an exam room where the scheduling system automatically detects when the patient arrives in an assigned exam room according to an example.

FIG. 11B shows an example of an exam room where the scheduling system 1000 automatically detects when the patient arrives in the assigned exam room. The patient device 1414 is shown communicating with the stationary device 1420 assigned to the assigned exam room. Examples of preferred sensor systems 1300 include sensors for close proximity (5-10') handshake that yield high proximity-temporal accuracy-reliability, such as Bluetooth or infrared sensors. Both the stationary device 1420 and the patient device 1414 are pre-loaded with code to communicate with each other, as well as to communicate with the stationary device 1420, the network 1200, the processing circuitry 1400 and/or the server 1430.

In the alternative the accelerometer on the patient device 1414 detects movements as "steps" and estimates a distance travelled. A minimum distance can be pre-entered into the system, or customized per office layout. In a similar manner, the scheduling system 1000 can detect when the patient has left the location, using steps alone, or alternatively combined with a Bluetooth close proximity (5-10') handshake. In the alternative, the nurse or office staff can push a button on the stationary device 1420 that the patient is in the exam room.

In the alternative the one or more mobile devices 1410 can use WiFi, or the like, which operates at a longer range. The transmitted signal can switch power outputs from 100 mw to 10 mw to 1 mw (whisper/shout), further the receiving side can measure the SNR of valid data packs so as not to be confused with colliding signals from other WiFi systems.

FIG. 11C

Figure 11C:
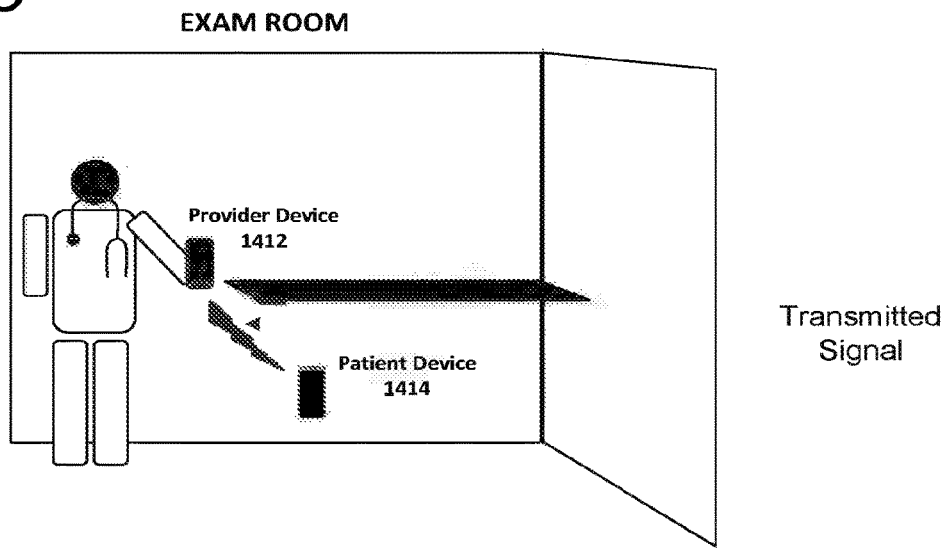
FIG. 11C shows an example where the system automatically detects when the provider arrives in the exam room according to an example.

FIG. 11C shows an example where the system automatically detects when the provider arrives in the exam room. The patient device 1414 is shown communicating with the provider device 1412 assigned to the provider. Examples of preferred sensor systems 1300 include sensors for close proximity (5-10') handshake that yield high proximity-temporal accuracy-reliability, such as Bluetooth or infrared sensors. The one or more sensor systems 1300 either send or receive a transmitted signal.

In the alternative the provider can generate the discrete signal 1340 by pushing a button on the provider device 1412 indicating that they are "meeting with patient" from the ordered list 1110. In the alternative the provider can push a button on the stationary device 1420 if present indicating that the "Provider is meeting with the patient". Other buttons may include "Provider needs assistance", "emergency or Code Blue", "VIP patient", or "Extend PAD". Each button can be configured to perform a respective function.

FIG. 12A

Figure 12A:
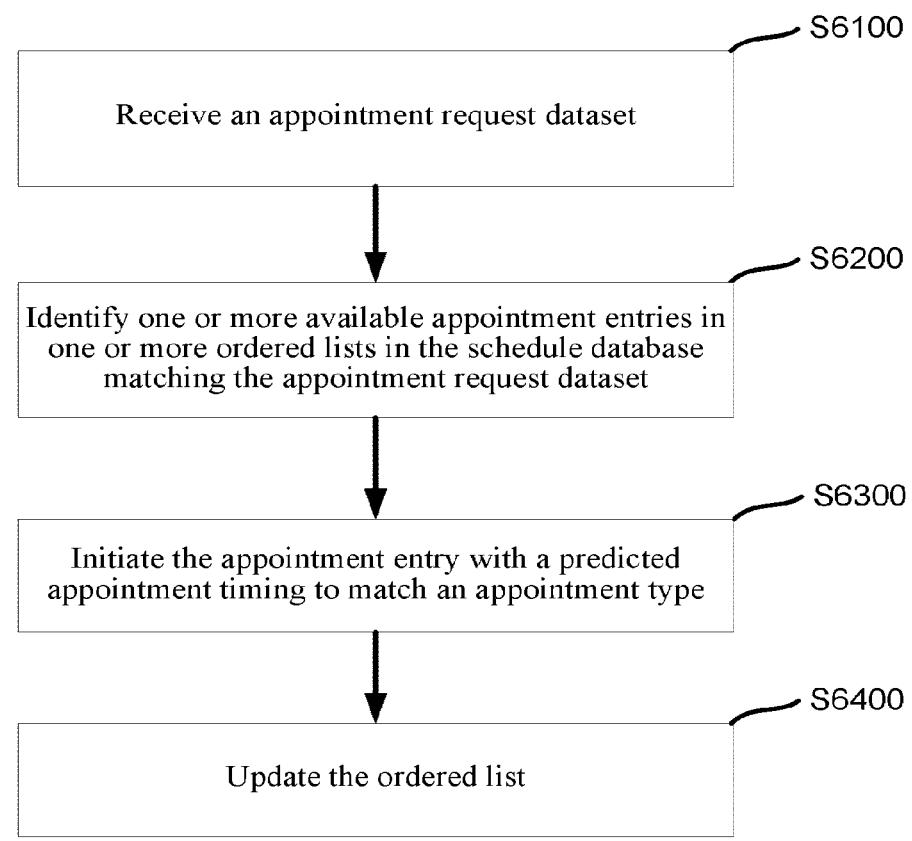
FIG. 12A is a flow diagram illustration of a method for assigning a patient appointment to the schedule according to an example.

FIG. 12A is a flow diagram illustration S6000A for assigning a patient appointment to the schedule according to an example. Flow diagram illustration S6000A includes the steps of receiving an appointment request dataset S6100, identifying one or more available appointment entries in one or more ordered lists in the schedule database matching the appointment request dataset S6200, initiating the appointment entry with a predicted appointment timing 2100 to match an appointment type S6300, and updating the ordered list S6400.

Step S6100

The step of receiving an appointment request dataset S6100 can be done according to several scenarios. In one scenario, the scheduling process is initiated by an appointment request to the API 1490. An appointment request includes one or more appointment request data sets. In one example, the appointment request data set includes a preferred time for the patient's appointment. The preferred time can include a day of the week, e.g. Monday, and a time designation for morning or afternoon, e.g. AM or PM. In one example, the preferred time does not represent a specific date, whereas in another example, the preferred time does represent a specific date. The appointment request data set is used by the API 1490 to query the schedule database 1100 of one or more providers for one or more matching available appointment entry in the future.

Step S6200

The step of identifying one or more available appointment entries in one or more ordered lists in the schedule database matching the appointment request dataset S6200 can be done according to several scenarios. The appointment request initiates a search, based on the appointment request dataset, through a multiplicity of encrypted links via the API 1490 into multiple third party servers and databases. The appointment request dataset is used by the API 1490 to query a provider's office schedule for matching future calendar dates. Matching dates are then searched individually to determine candidate appointment times. The candidate appointment times are returned to the patient to choose from by a software interface.

A candidate appointment time can found by analyzing an ordered list 1110 within the schedule and identifying one or more schedule matches of availability. In one example the schedule match is a block of unallocated time for the entire appointment timing and an acceptable total waiting time. In another example, the schedule match is a set of distributed unallocated times corresponding to the set of appointment states making up the appointment type 1133 including their duration and an acceptable total waiting time.

In one example, each provider's office includes a base appointment duration, e.g. 30 minutes. The base appointment duration defines a minimum schedule match that can be a candidate appointment time. Each schedule match is evaluated to determine if the respective set of procedure resources 3000 are available to fulfill the appointment as well as result within the acceptable total waiting time.

According to another scenario, the available appointment entry is determined by a scheduling algorithm. The scheduling algorithm provides a number of assignable procedure resources 3000 and a corresponding time duration the provider can assign to the ordered list 1110 each day of a schedule. The scheduling algorithm evaluates availability for each procedure resource type individually and in combination with the other procedure resources required to fulfill the expected one or more procedure types 1150 for the appointment type 1133. The scheduling algorithm can be configured to avoid a schedule match that has conflict with the ordered list 1110, as well as to identify a schedule match that maximizing a remaining availability of schedule matches to maximize the number of other procedure types 1150 or appointment types 1133 to be scheduled for the ordered list 1110 that day. For instance, if two schedule matches are available to fulfill the request, the schedule match that results in the schedule having a greater number of options for scheduling procedure types 1150 is ranked higher.

To determine an overlap, the scheduling algorithm evaluates all of the appointment states of the appointments in the schedule by the appointment type 1133. An overlap occurs when the same assigned procedure resources 3000 are assigned to different appointments at the same time.

The appointment states correlate with the patient state 2210 during the day of the appointment. For example, the appointment state of S110 (check in) correlates with the patient state 2210 of 'WR' or "in waiting room."

In this case, the scheduling algorithm can use one or more optimizing methods to minimize the waiting time of the patient, as well as to maximize the use of the most limiting procedure resource 3000. Optimizing methods can include (1) offsetting the base time of the appointment, (2) restacking the ordered list 1110, (3) reassigning the procedure resources 3000, and (4) alerting the provider to add one or more additional procedure resources 3000 to assign to the schedule. An example of the one or more additional procedure resources 3000 is requesting an additional nurse to work on the shift for that day. In case the scheduling algorithm failed to find a schedule match in all of the available provider's schedules, the scheduling algorithm will provide the closest matching appointment time to the appointment request data set.

In an alternate embodiment where not all types of providers are scheduled or are being tracked in the schedule system, the schedule system can notify the provider staff to seek alternate procedures resources to fulfil the appointment state by the qualifications of the appointment type 1133.

Upon receiving a set of available appointment entries, the patient can select their preferred appointment entry. The selected appointment entry is then returned to the API 1490, which then adds the appointment entry in the provider's schedule. The appointment entry can be marked as 'pending' until the provider staff either approves the appointment time or adjusts the estimated appointment time, the PAD, or modified the ordered list 1110 to match the appointment request. For example, based on the appointment type 1133 and patient history, the provider may adjust a PAD for a specific procedure resource 3000, such as extending the time duration for a nurse to draw blood samples from a patient that is expected to be more difficult.

Third party patient schedule data must be protected to meet HIPAA requirements and therefore must not be shared between the different EMR systems. Therefore, the scheduling system 1000 accesses a combination of otherwise unavailable data including data from multiple provider's offices, multiple EMR providers, multiple third party patients, and maintains this collective information temporarily and in an encrypted form to accomplish the benefits.

Step S6300

Step S6300, initiating the appointment entry with the predicted appointment timing to match an appointment type, can be done according to several scenarios. The prediction of the appointment timing 2100 prior to the day of the schedule appointment can be done using actuarial data from the archive 1600 according to an example. In this step, the PAD based on the actuarial data related to the appointment type 1133 is associated with a patient ID and assigned in the ordered list 1110. In this example, fitting of actuarial data to new appointments includes correlation, linear regression, interpolation, and least mean fit methods. In another example, the prediction of the appointment timing 2100 is done using input from the provider's office staff. According to another example, the initial prediction of the appointment timing 2100 can be done using reimbursement and billing codes based on the medical procedures 1150 associated with the appointment type 1133. In this example, the scheduling system 1000 can be configured to access one or more third party billing systems.

According to an example, the prediction of the appointment timing 2100 can be based on one or more appointment factors including a type of practice, a set of previous appointment details, a macro adjustor, and a month or season. Examples of the type of practice include various types of healthcare services including dentistry, physical therapy, and subspecialties of medical doctors such as ophthalmology, ENT, internal medicine, pediatric, etc. In another example, clinician earned degrees and certifications such as M.D. Vs D.O, and F.A.C.C. for Cardiologists, etc., can be included in the appointment factors. The set of previous appointment details can include the patient ID 1120, a first visit designation (e.g. new/old), the procedure type 1150, the medical need, and the provider name. The macro adjustors include a time of day and a day of week. The month or season includes secular and religious holidays, a day before a holiday, and other defined personal days.

The appointment entry includes an associated patient, a set of appointment entry components, and a set of prediction values corresponding with each appointment entry component by respective archival appointment entries. Each appointment entry component includes an associated appointment location 1135 and the predicted timing. The predicted timing may be done through several scenarios. In this case the predicted timing is generated from the archived timing 1620 for the appointment type 1133.

Step S6400

The step of updating the ordered list S6400 is described by flow diagram S4000 in FIG. 4A.

In one embodiment, when a patient submits an appointment request or an appointment schedule match availability from multiple providers are searched. In one case the multiple providers can compete and there is an additional step for a "negotiation" to "win" an available appointment entry from each competing provider's schedule. In one example the negotiation can be similar to advertising negotiation methods for an advertisement placement. The negotiation can be based on any of the appointment request data and/or any of the patient information mentioned above.

In another embodiment, a patient can pay for an option to restack the ordered list 1110 or the schedule database 1100 to favor their preference in appointment timing. In this case the patient can be considered a "VIP Patient". Similarly, the provider can offer an incentive for patients that have modified appointment timing (e.g. delayed or rescheduled).

Figure 12B:
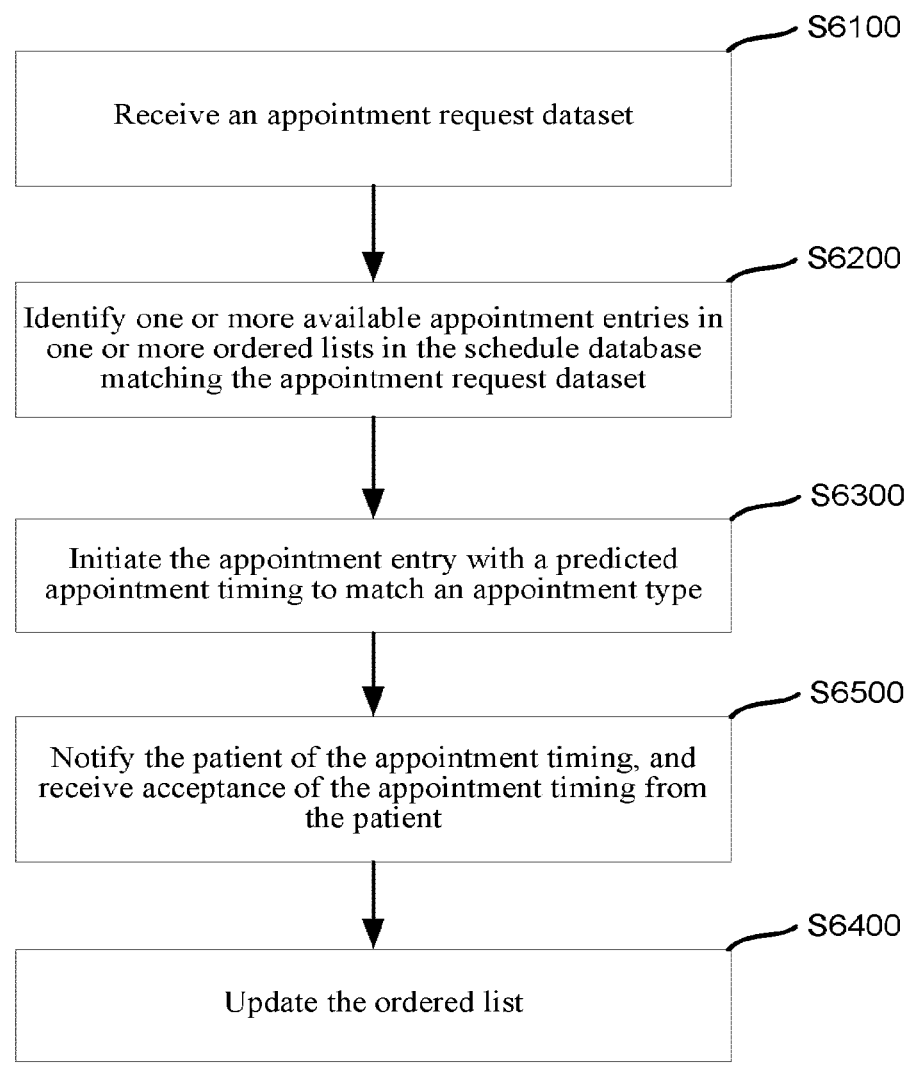
FIG. 12B is flow diagram illustration of a method for assigning a patient appointment to the schedule according to another example.

In another embodiment, a patient loyalty program, similar to a customer loyalty program, can be used to favor the patient's preference in their respective appointment timing.
FIG. 12B FIG. 12B is flow diagram illustration S6000B, which is an alternate example for assigning a patient appointment to the schedule. Flow diagram illustration S6000B includes the steps of flow diagram illustration S6000A and further includes step S6500 to notify the patient of the appointment timing 2100, and receive acceptance of the appointment timing 2100 from the patient. In one example, step S6500 occurs after step S6300. In another example, it can occur after step S6400. In one example, receiving acceptance from the patient can be receiving an affirmative response. In another example, receiving acceptance from the patient can be receiving a confirmation that the communication was delivered and not receiving a rejection response. In this case, there can be a set time limit and a timer for the patient to input their response. After the time limit has expired the patient's response will be considered as an acceptance.

Pre-Check-In Step

In another example, a pre-check-in step can be requested by the provider and communicated to the patient prior to their appointment. In one case, the pre-check-in may require or advise the patient to perform a behavior modification (e.g. fasting) to help a diagnosis. In another case the pre-check-in may require the patient perform one or more medical lab tests, and for the corresponding medical lab test results to be available for review prior to the appointment. In this case, the patient can be pulled out of the ordered list 1110 and added back in after the pre-check-in step is complete.

Figure 12C:
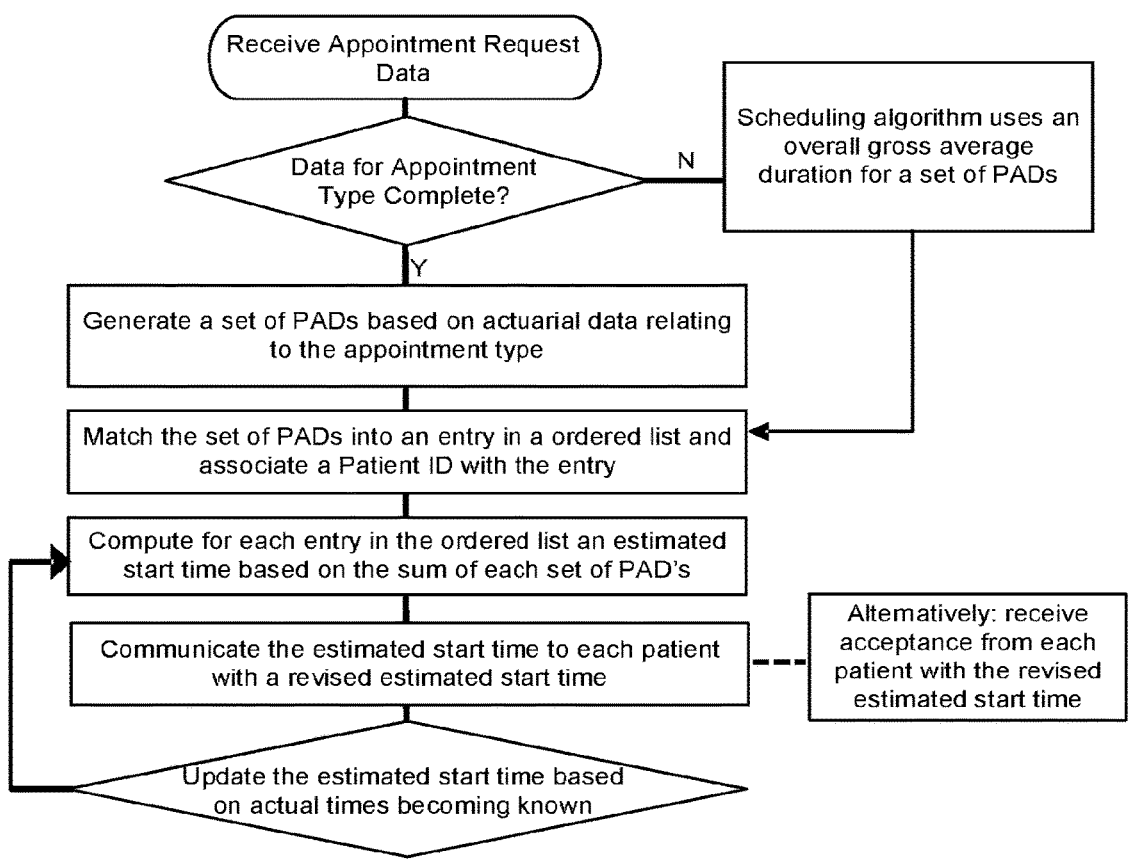
FIG. 12C shows a flow diagram for a method of entering a new patient appointment without an appointment type identified according to an example.
Figure 13B:
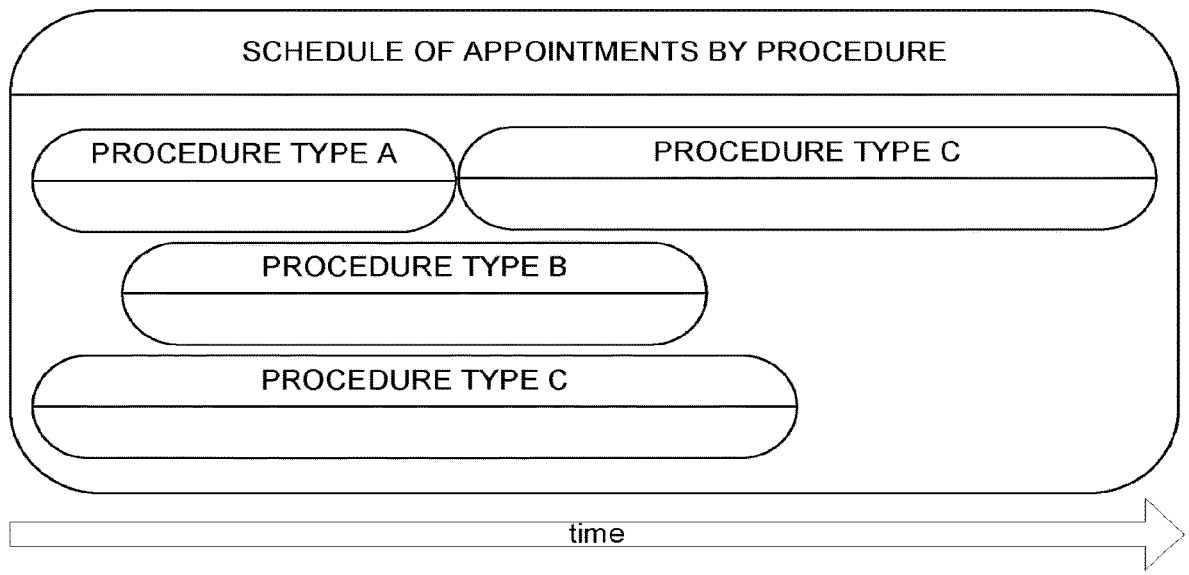
FIG. 13B shows the schedule of appointments by procedures over time according to an example.
Figure 13C:
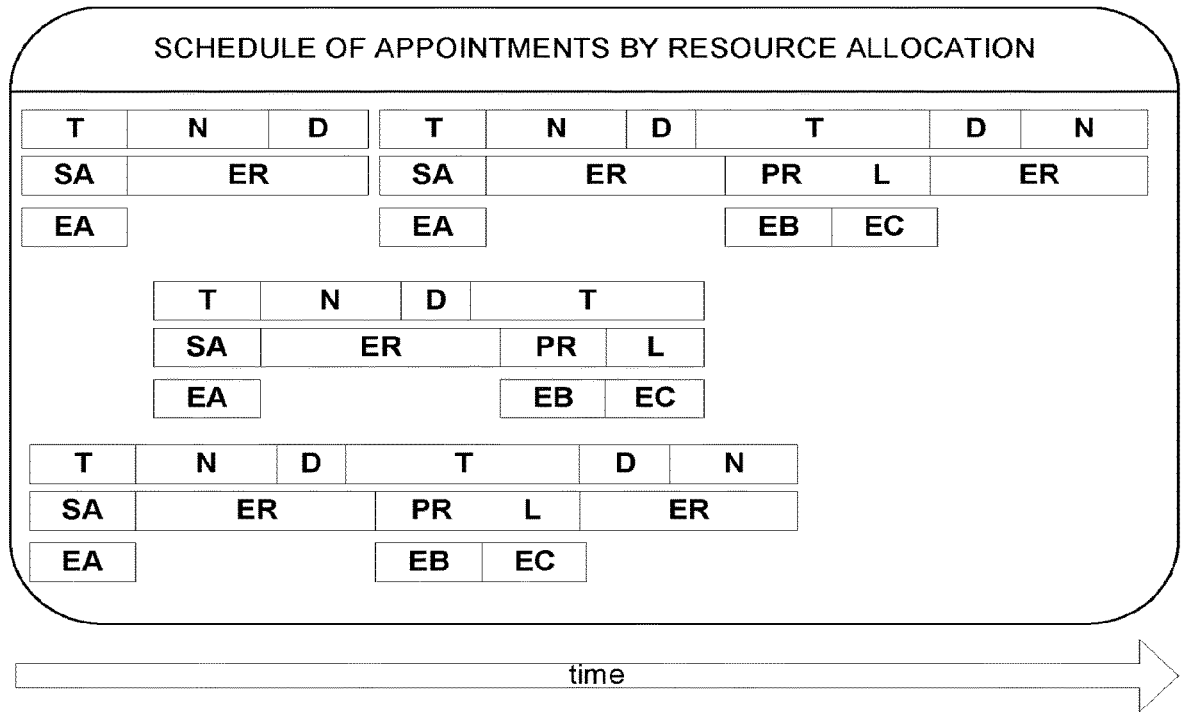
FIG. 13C shows the schedule of appointments with an example of a set of procedure resource allocations allocated for each procedure type according to an example.

In another example, the pre-check-in can include submitting administrative information (e.g., patient identity, payment, and insurance information) electronically. Completion of this pre-check-in step can modify the PAD associated with the appointment entry. The patient can print any pre-check-in documents and complete it at their convenience prior to check in. In an example, at least partial patient information from the pre-check-in documents can be automatically mapped to corresponding fields of the patient appointment entry.
FIG. 12C FIG. 12C shows a flow diagram for entering a new patient appointment without the appointment type 1133 identified according to an example. As discussed above, knowing the appointment type 1133 of the appointment allows the scheduling system 1000 to provide the set of predicted timing durations based on the archived timing 1620. In the case where the appointment type 1133 is unknown, the scheduling algorithm can use a generic appointment type 1133 having gross average durations for the set of appointment states.
FIG. 13A FIG. 13A shows three examples of a set of procedure resource allocations 3300 for the procedure type 1150 where the procedure resources 3000 are shown with the PRT indicated for each resource including the order expected. In a first example, a procedure type A is shown including a technician (T), a nurse (N), and a doctor (D), in parallel with a staging area (SA) and an exam room (ER), also in parallel with a piece of equipment A (EA). In second example shown, a procedure type B is shown including a technician (T), a nurse (N), a doctor (D), and the technician again, in parallel with a staging area (SA), an exam room (ER), a procedure room (PR), and a lab (L), also in parallel with a piece of equipment A (EA), a piece of equipment B (EB), and a piece of equipment C (EC). In a third example shown, a procedure type C is shown including a technician (T), a nurse (N), a doctor (D), the technician (T) again, the doctor (D) again, and the nurse (N) again, in parallel with a staging area (SA), an exam room (ER), a procedure room (PR), a lab (L), and the exam room (ER) again, also in parallel with a piece of equipment A (EA), a piece of equipment B (EB), and a piece of equipment C (EC).
FIGS. 13B-13C FIG. 13B shows an example of the schedule of appointments by procedures over time. Four scheduled procedures are shown having three procedure types.

Figure 13D:
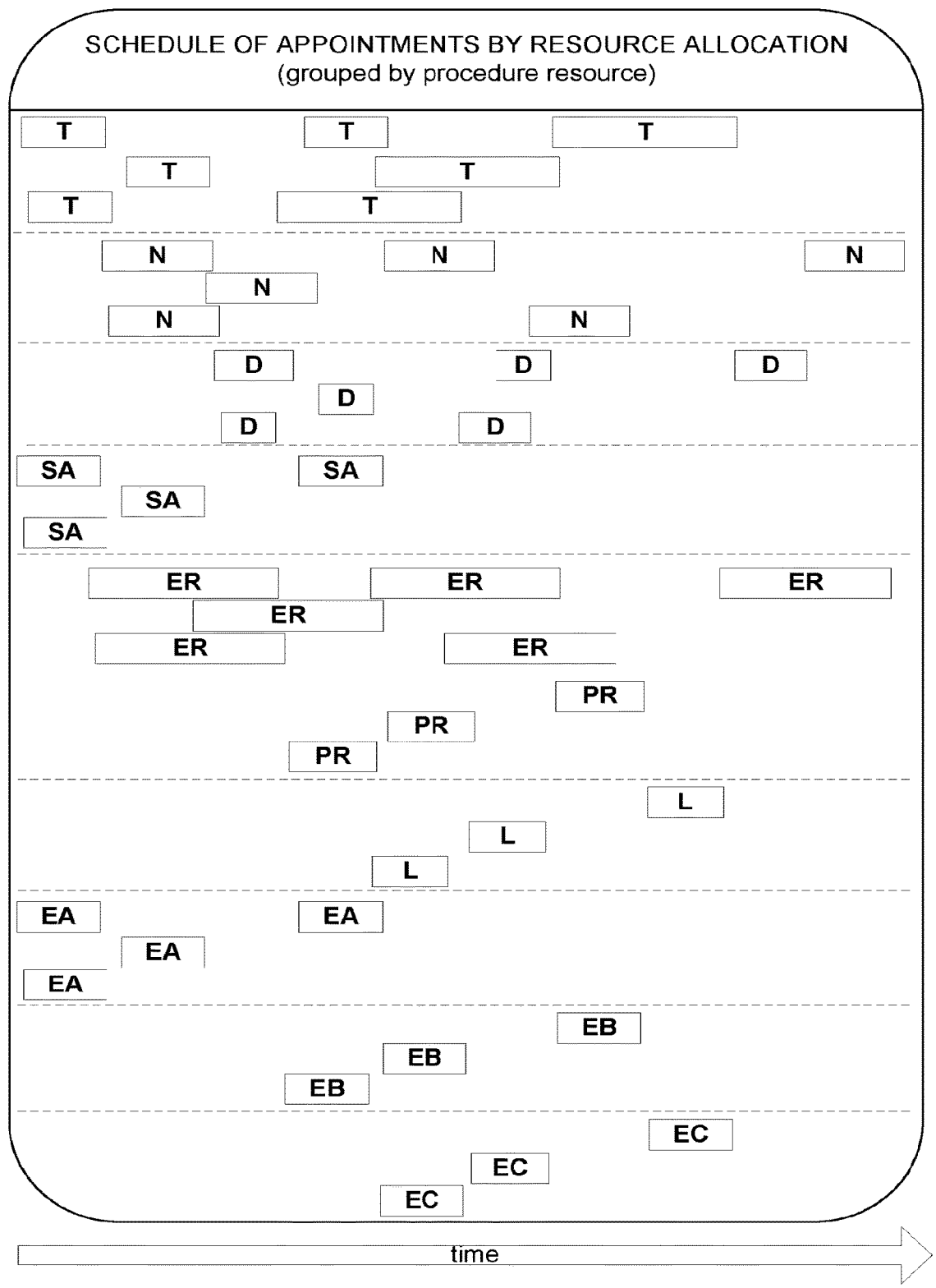
FIG. 13D shows the schedule of appointments by resource allocation as shown in FIG. 13C, only now grouped by the type of the procedure resources according to an example.
Figure 13E:
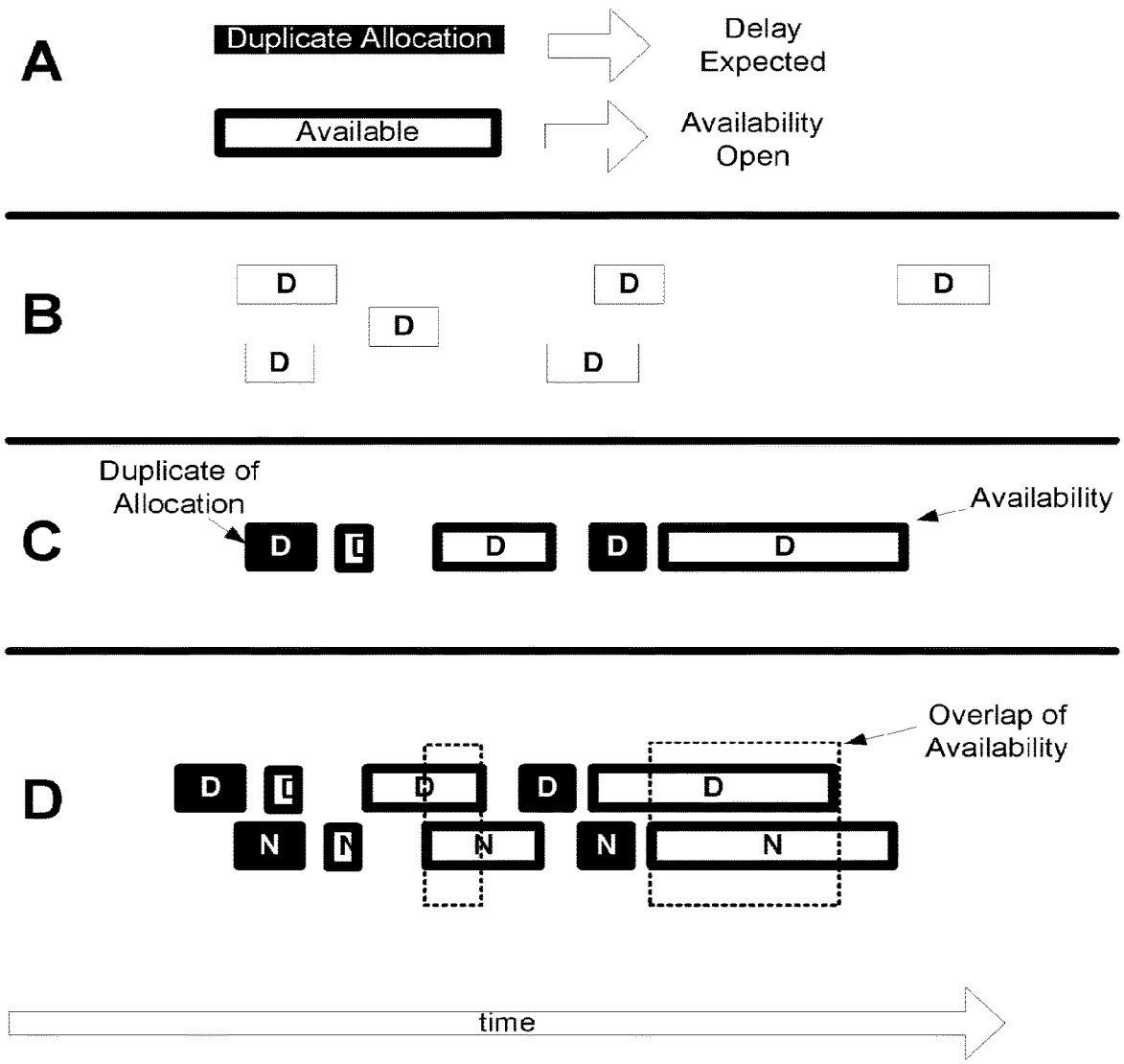
FIG. 13E shows several views of analyzing allocation and availability of the scheduled procedure resource allocations according to an example.

FIG. 13C shows the schedule of appointments with an example of a set of procedure resource allocations 3300 allocated for each procedure type 1150. The procedure resource allocations 3300 allocated for each procedure type 1150 are shown grouped together in a similar arrangement as the procedure types are scheduled in FIG. 13B.
FIG. 13D FIG. 13D shows the schedule of appointments by resource allocation as shown in FIG. 13C, only now grouped by the type of the procedure resources 3000. In this view, the spacing and the overlap of the allocation of the same type of the procedure resources 3000 can be seen.
FIG. 13E FIG. 13E shows several views of analyzing allocation and availability of the scheduled procedure resource allocations 3300 according to one example. At section A, an indictor on the procedure resource allocations 3300 is shown to alert that the procedure resource allocations 3300 is allocated more than once and a delay is expected, and a different indicator is shown to notify that an availability is open. At section B the example of the grouped allocation for the doctor (D) from FIG. 13D is reproduced. At section C, the duplicate allocation for the doctor (D) is shown, as well as the availability meeting the minimum block required for another procedure. In this example, the availability open times that are less than the minimum time block are not shown. In section D, the allocation of the nurse (N) is also included. Here an overlap of availability can be seen between the doctor (D) and the nurse (N).

Figure 13F:
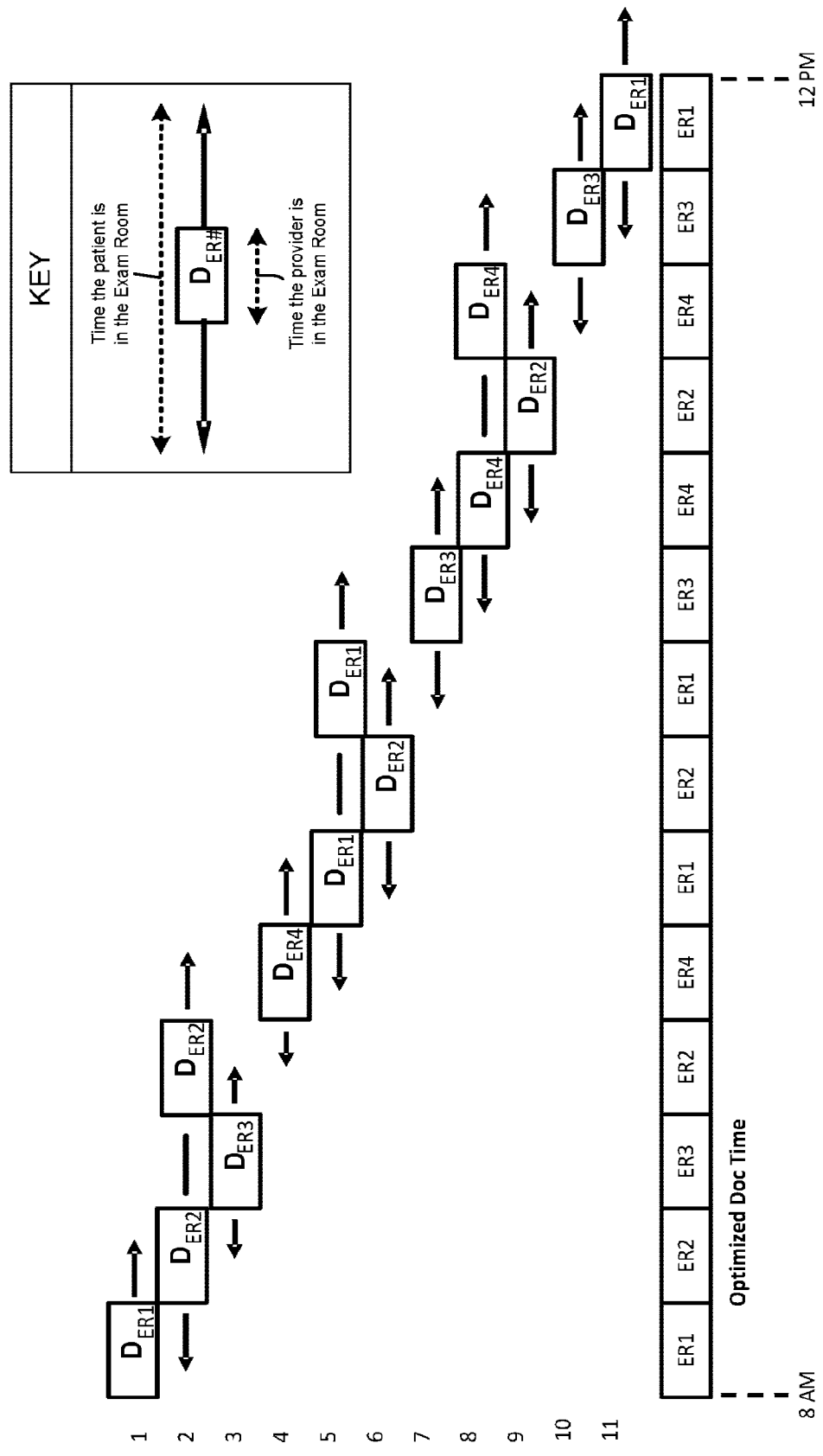
FIG. 13F shows an optimized provider's schedule including the time a patient is in the assigned exam room and the time the provider is in the exam room according to an example.
Figure 14A:
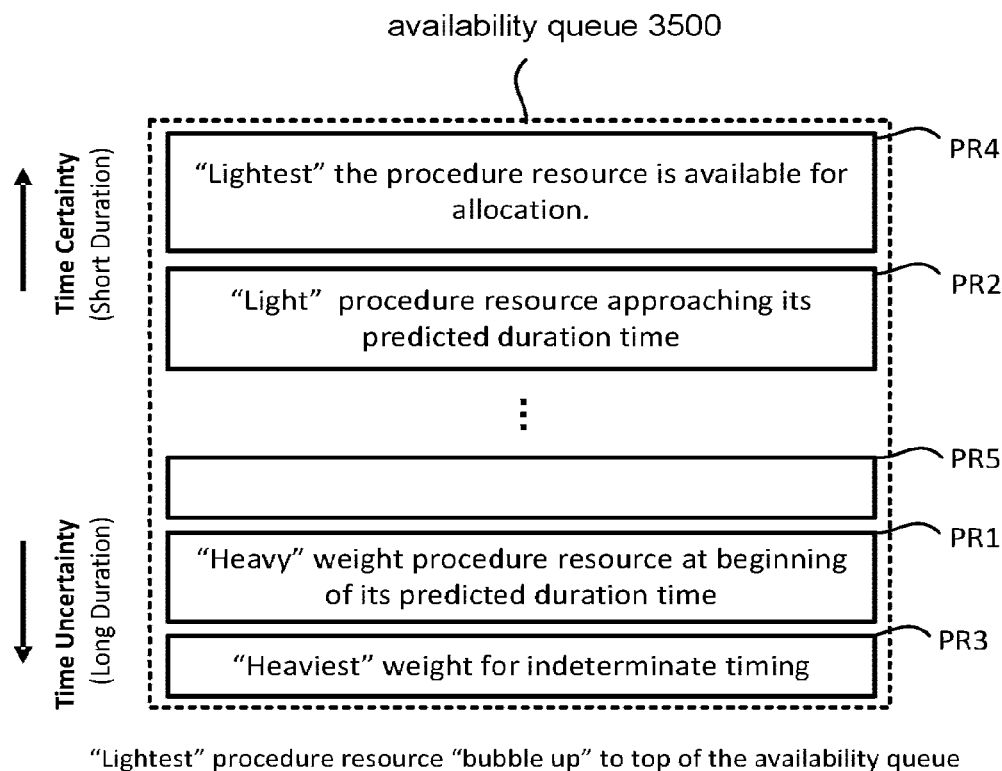
FIG. 14A shows a bubble-up process on a procedure resource availability queue or availability queue for a set of procedure resources having the same type according to an example.
Figure 14B:
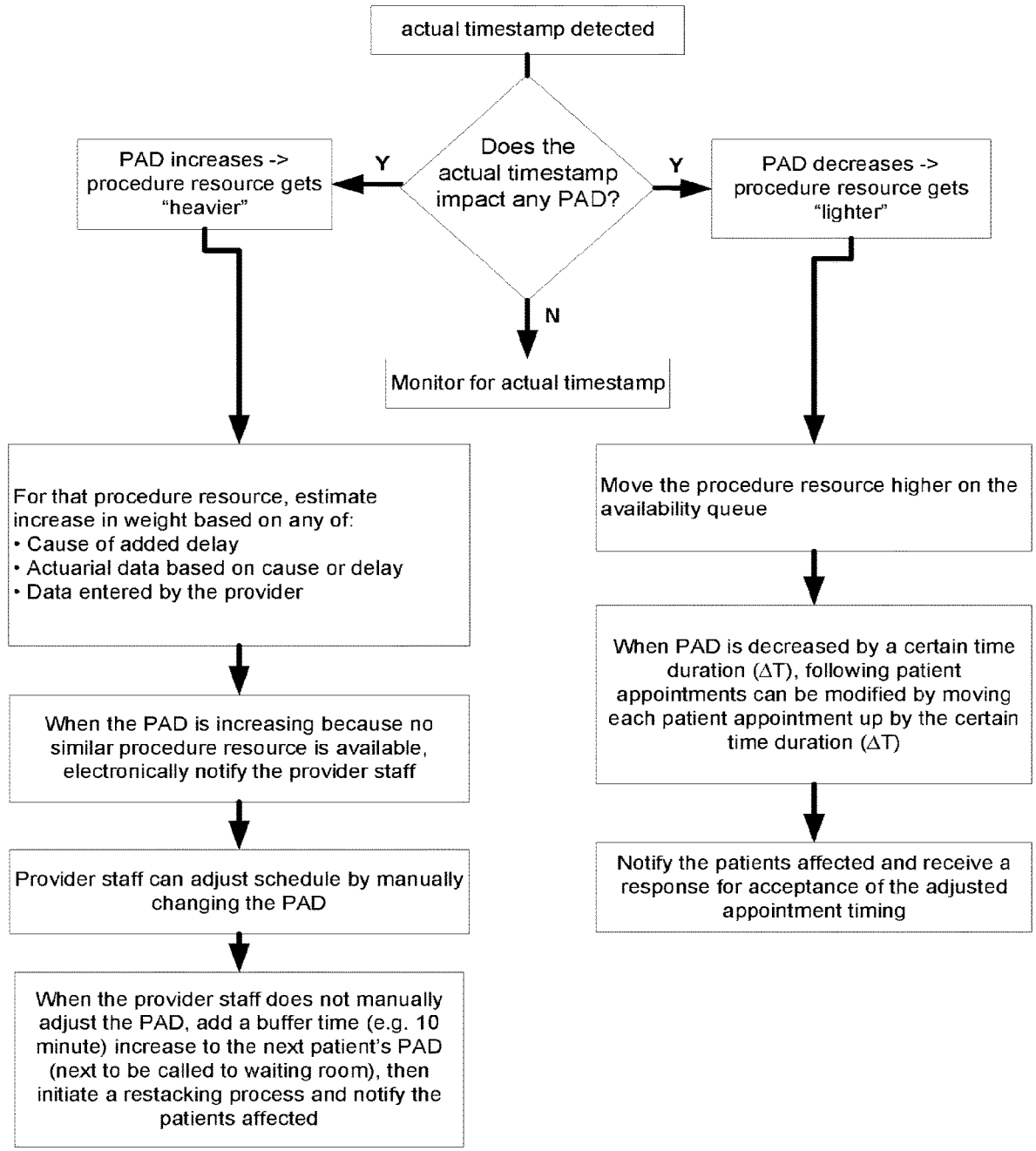
FIG. 14B shows a bubble-up handler configured to monitor how a new actual timestamp affects the PAD's in the schedule and to rank the availability of the set of procedure resources in their respective availability queues according to an example.

In one example, the restacking method functions to compare different scenarios for identifying fragmented availabilities for new appointments and minimizing the total waiting time.
FIG. 13F FIG. 13F shows an optimized provider's schedule including the time a patient is in the assigned exam room and the time the provider is in the exam room. In another example, the schedule is optimized to any procedure resource 3300.
FIG. 14A FIG. 14A shows an example of a bubble-up process on a procedure resource availability queue or availability queue 3500 for a set of procedure resources 3000 having the same type.
FIG. 14B FIG. 14B shows an example of a bubble-up handler C1700 configured to monitor how a new actual timestamp affects the PAD's in the schedule and to rank the availability of the set of procedure resources 3000 in their respective availability queues 3500. In this example, the availability queue 3500 from FIG. 14A is ranked. When an actual timestamp is detected the bubble-up handler C1700 computes the time difference with the respective PAD and determines if the PAD increases, thereby making the procedure resource 3000 "heavier," or if the PAD decreases, thereby making the procedure resource 3000 "lighter."

Examples of when the PAD increases include when the assigned nurse is unavailable, when the provider is staying longer with the patient than predicted, when an unexpected test is ordered, when a piece of equipment is unavailable, and when an emergency procedure is required. Examples of when the PAD decreases include when the provider time duration is shorter than predicted, when a planned test is not needed, when an allocated procedure resource 3000 is not needed in the procedure type 1150 scheduled, and when the patient is rescheduled. In an example, the when the PAD is decreased by a certain time duration (ΔT), following patient appointments can be modified by moving each patient appointment up by the certain time duration (ΔT). Notify the patients affected and receive a response for acceptance of the adjusted appointment timing.

FIG. 14C

Figure 14C:
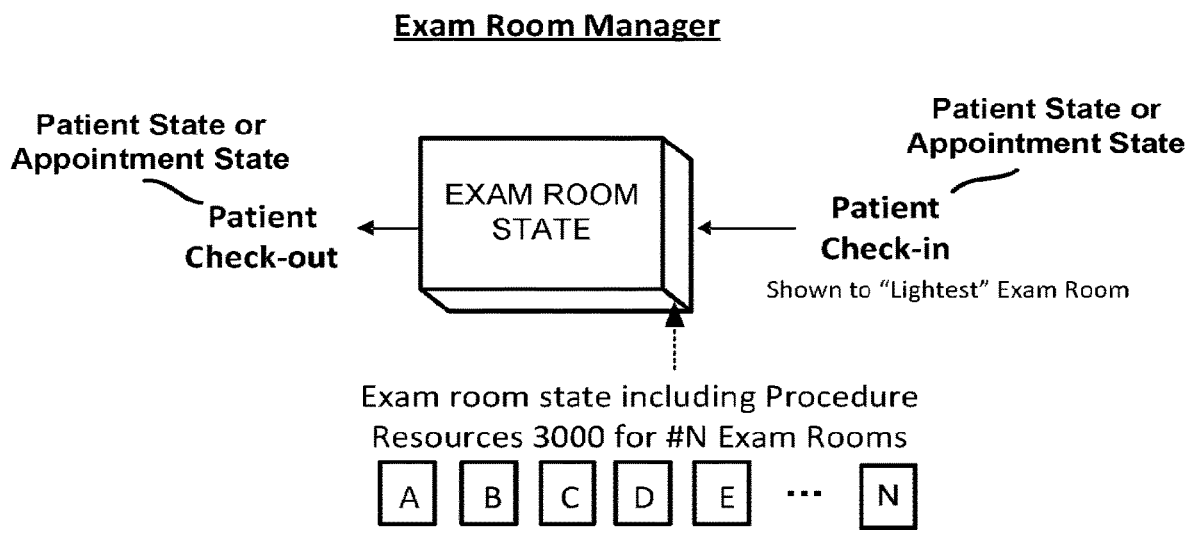
FIG. 14C shows an exam room manager for tracking an availability of a set of exam rooms according to an example.

FIG. 14C shows an example of an exam room manager for tracking an availability of a set of exam rooms. In this example each exam room has one or more exam room states. Each exam room state can include or reflect the patient state 2210, such as the patient check-out and the patient check-in state, as well as the appointment state. An example of the exam room state can include a waiting description such as waiting for nurse, waiting for doctor, waiting for equipment, waiting for medication, etc. The waiting description can be used for analytics on the efficiency of the procedure type 1150. The total number of exam room states can be variable and depend on the appointment type 1133 or number of appointment states and a respective duration for each exam room state is accordingly set.

In an example, the exam room manager can use the bubble up handler to modify the exam room state such that a longer duration of the appointment state or one with an unpredictable PAD is pushed-down/demoted and predictable or a lower PAD is pushed up/promoted such that the lightest element represents an exam room that is either recently vacated or about to become vacated.

In one example, the set of exam rooms are all within a single provider office. In another example, the set of exam rooms can be distributed among different provider offices. According to an example, each exam room state can include the set of allocated procedure resources 3000. Examples of the set of allocated procedure resources 3000 include the one or more assigned providers and the equipment required for the procedure type 1150.

FIG. 14D

Figure 14D:
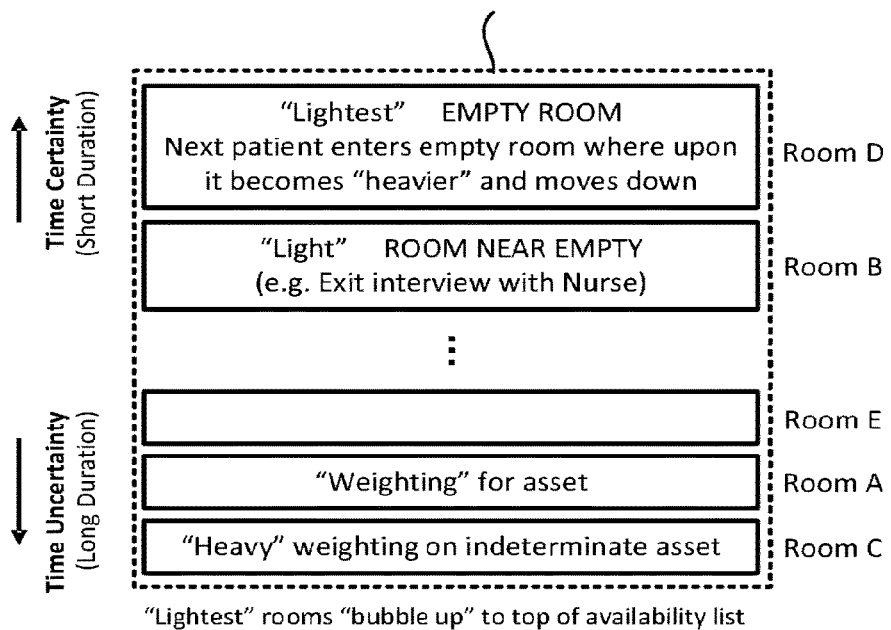
FIG. 14D shows the bubble-up process for determining the exam room availability according to an example.

FIG. 14D shows an example of the bubble-up process for determining the exam room availability. Each exam room can be ranked by its exam room state or a respective predicted timing factor. The predicted timing factor can indicate a predicted time or a time duration until the exam room is available for a new patient. The predicted timing factor is smallest and most certain at the end of the patient appointment, thereby "lighter". Conversely, the predicted timing factor is greatest and least certain when a new patient is checked into the exam room, thereby "heavier". An unknown exam room state becomes the "heaviest" due to unreliability of the estimate. Throughout the appointment, each appointment state or patient state can influence the "heaviness" of the exam room availability. As the patient appointment progresses, the exam room availability becomes "lighter" and a bubble up process advances the exam room state higher toward the top of the availability queue 3500.

FIG. 15

Figure 15:
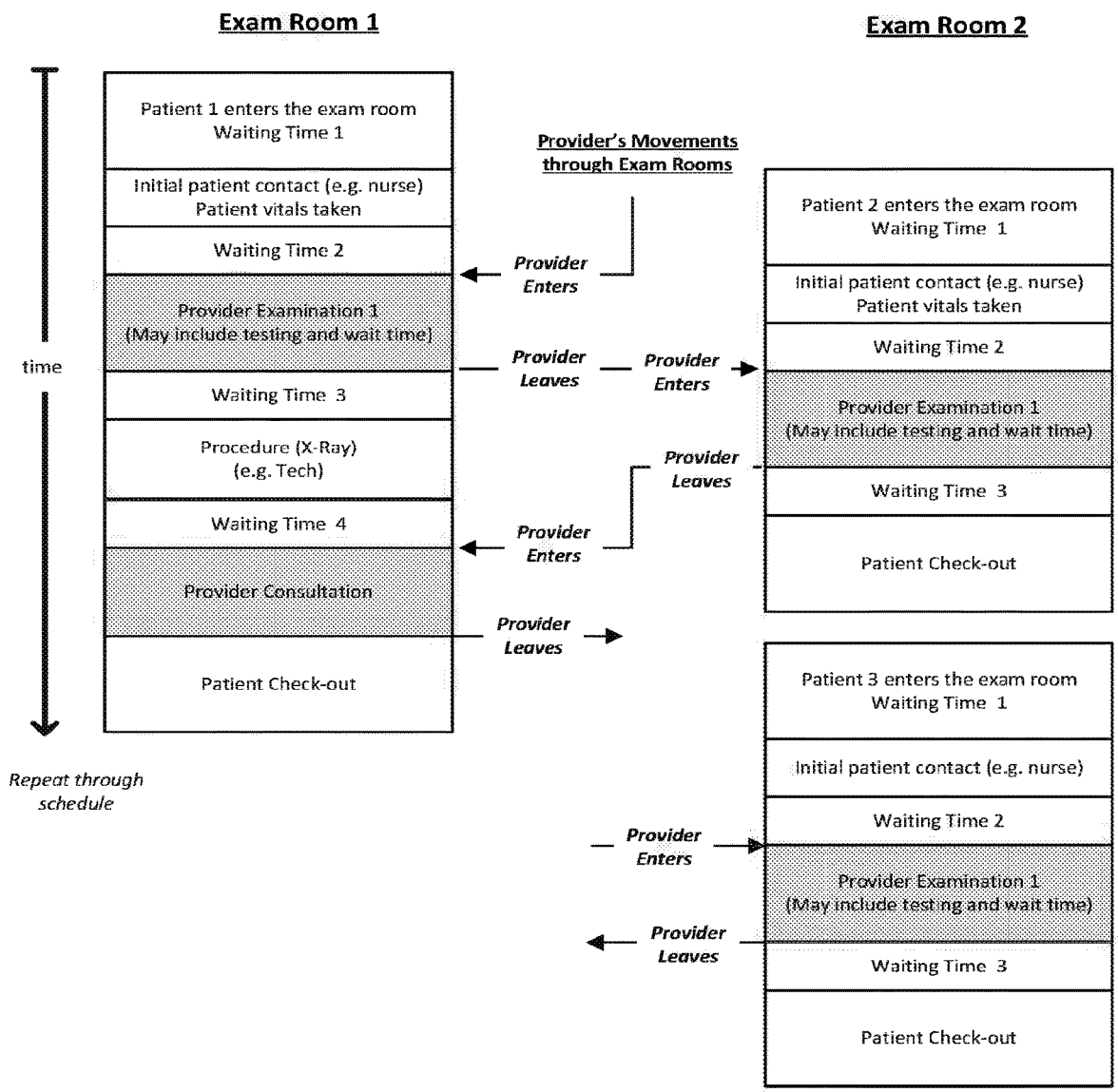
FIG. 15 shows the provider's movements between two exam rooms allocated to different appointments having multiple appointment states, as well as different patient waiting times between the appointment states according to an example.

FIG. 15 shows an example of the provider's movements between two exam rooms allocated to different appointments having multiple appointment states, as well as different patient waiting times between the appointment states. The appointment states are shown with the procedure types 1150 that are being done. With each provider movement into and out of the exam rooms, an actual timestamp 1320 is created and associated with the respective patient appointment. In this example, only the movements of one provider are highlighted even though there are other providers entering and exiting as well (e.g. nurse and tech).

In other words, a provider device or patient device can be configured to detect the beacon or gateway in the room (i.e. event) and to notify the processing circuitry of the event. The processing circuitry can also be notified of the event when the patient scans a QR code at an appointment location, when a facial recognition camera detects the patient, and when a staff member records the event via the provider web or mobile app.

FIG. 16

Figure 16:
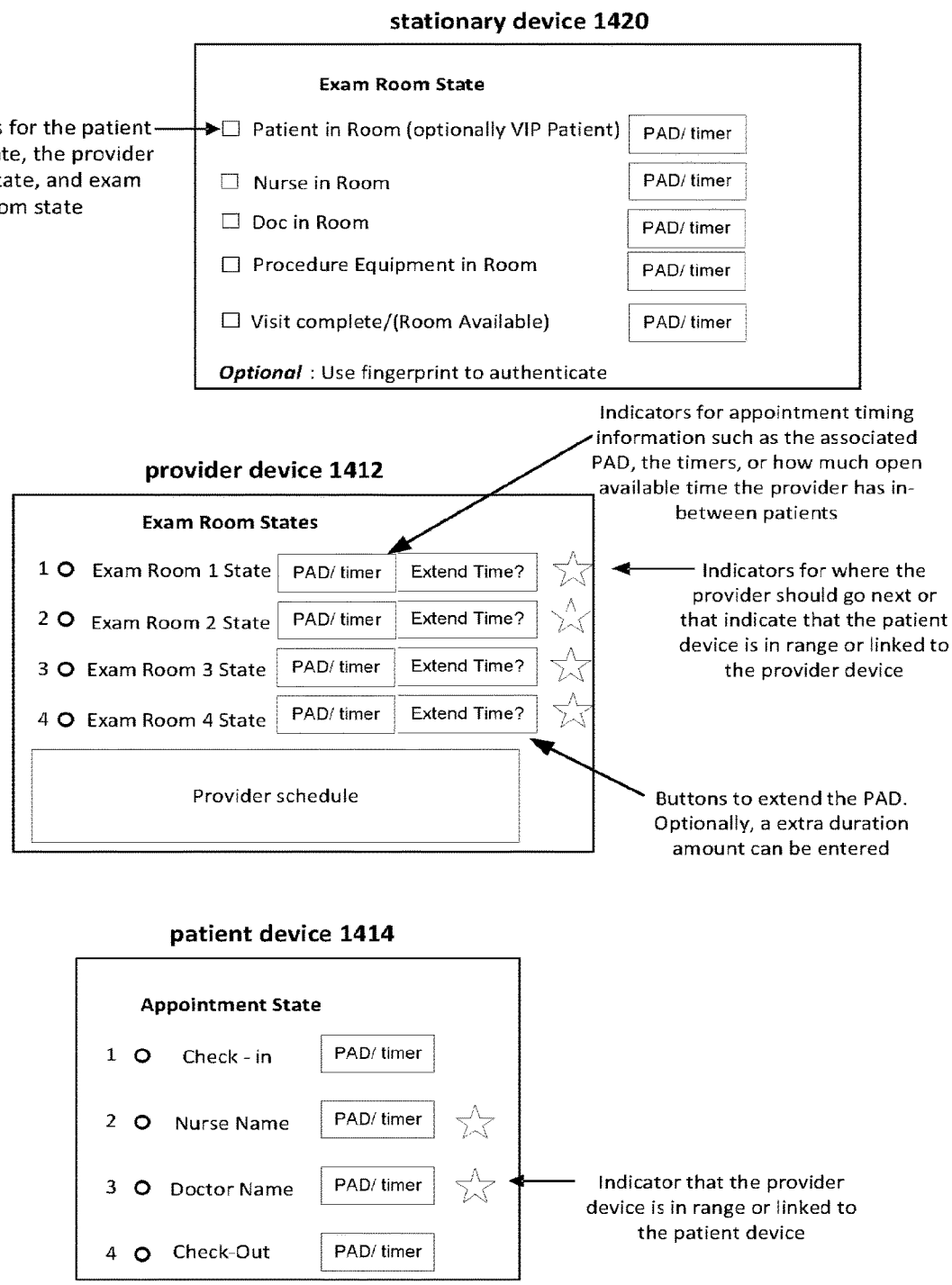
FIG. 16 shows examples of indicators and one or more indicators and buttons for the stationary device, the provider device, and the patient device according to an example.

FIG. 16 shows examples of indicators and one or more indicators and buttons for the stationary device 1420, the provider device 1412, and the patient device 1414. An example of the stationary device 1420 is shown with indicators for the patient status/state, the provider status/state, and the exam room state. An example of the provider device 1412 is shown with indicators for appointment timing information such as the associated PAD, the timers, or how much open available time the provider has in-between each patient, indicators for where the provider should go next or that indicate that the patient device is in range or linked to the provider device, and buttons to extend the PAD. An example of the patient device 1414 is shown with indicators that the provider device 1412 is in range or linked to the patient device.

FIG. 17

Figure 17:
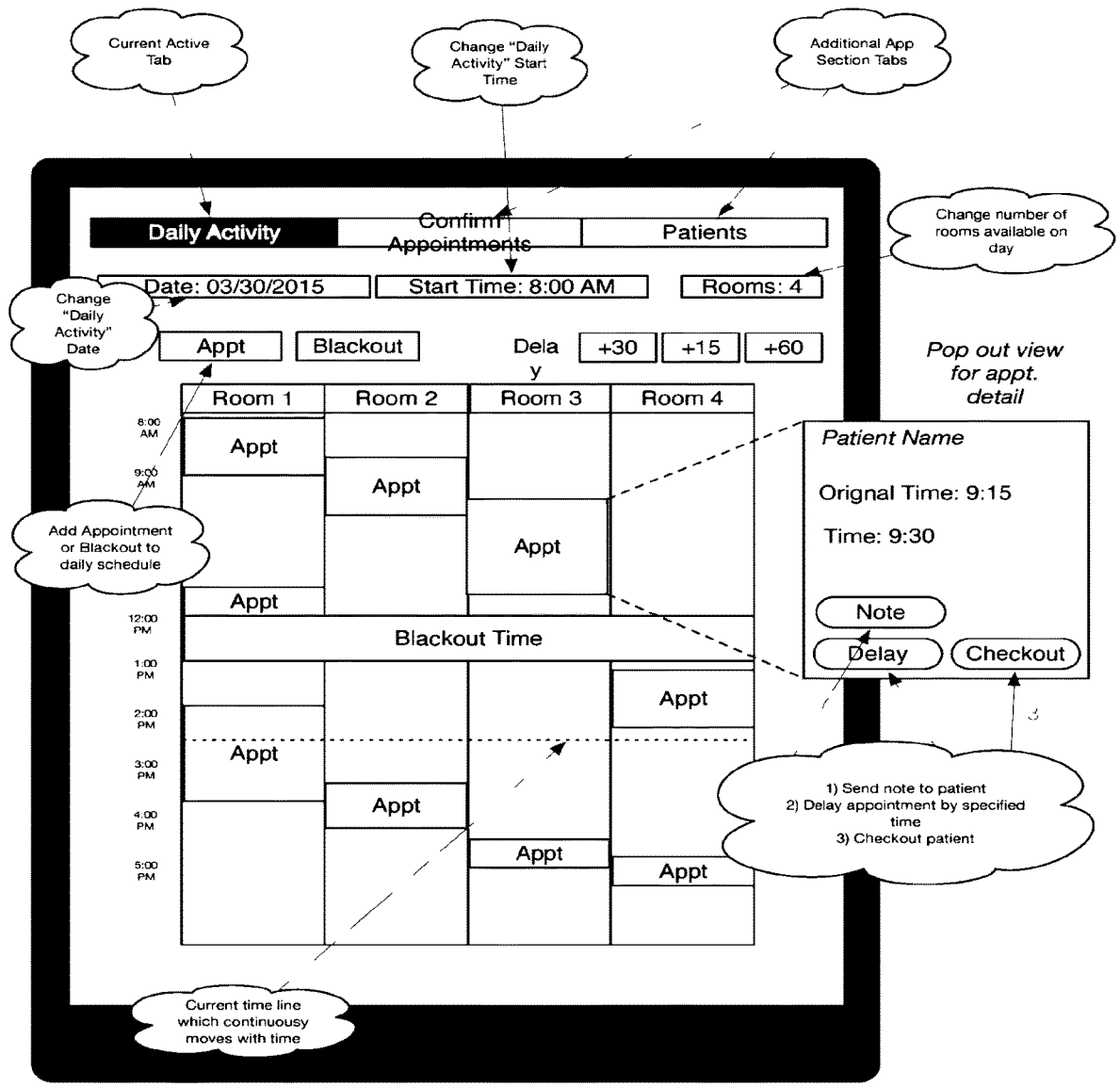
FIG. 17 an interface for the provider device according to another example.

FIG. 17 shows another example of an interface for the provider device 1412. The interface shows multiple tabs linking to different pages. The first page shown is a partial view of the ordered list 1110 as a daily activity.

FIG. 18

Figure 18:
FIG. 18 shows a mobile app shown on the patient device according to an example.

FIG. 18 shows an example of the mobile app shown on the patient device 1414. In an example, the mobile app on the patient device 1414 includes a new appointment request feature. The new appointment request feature includes a home screen, a search feature, a menu, and the appointment survey. FIG. 18 shows an example of the home screen shown on the patient device 1414. The mobile app includes one or more features relating to managing the appointment timing 2100, to communicating between the provider and the patient, and to tracking the proximity-time. In one example the home screen includes an appointment restack indicator, a message section, a phone feature, an appointment timing feature, and a map feature. The appointment restack indicator indicates that a more accurate arrival time for the patient has been calculated. For example, the patient's original appointment was scheduled for 3:15 pm, however the day of the appointment the provider is an hour behind schedule. The patient device 1414 notifies the patient that the more accurate appointment start time is 4:15 pm.

The message section displays notifications or notes from the provider for any pre-appointment behavior modification. In an example, the message section can provide a way for the patient to ask medical questions from their practitioner in a secure and HIPAA-compliant fashion, thus eliminating a need for a phone call or in-person visit. In another example, if the provider doesn't want the patient to eat before the appointment a notification will be shown here to remind the patient to arrive to the appointment with an empty stomach.

Respectively, on the provider device 1412 there can be a list of clinical orders that are requested of the patients. The provider or provider staff can input the respective notification which is sent to the respective patient device 1414. A phone feature allows the patient to start a call to the specific provider, initiating the patient device 1414 to operate a phone feature. Similarly, an email feature will operate an email service feature on the patient device 1414 to email the provider.

The appointment timing feature allows the patient to modify their expected timing and even cancel their appointment through the patient device 1414. Upon the communication of the appointment timing 2100, the provider is immediately notified and the restacking method is triggered. A map feature can display the provider's location on a map on the patient device 1414 and allow the patient to send an address to a map program on the patient device 1414 or open an internet-based map. A set of directions and a real-time estimate for arrival the appointment location 1135 from the patient's location are calculated. The real-time estimate can be based on traffic information, as well as the available mode of transit information.

In one embodiment, the scheduling system 1000 can coordinate with one or more third party transportation systems to provide a taxi or a ride to the provider office. The timing of the ride can be displayed on the patient device 1414 or a separate mobile app.

According to an example, the search feature includes a filter feature, a list feature, and a schedule appointment feature. The filter feature includes a medical specialty, a medical need, a provider's name, a shortest wait, an insurance type, a provider gender, a provider language, a payment type, and a preferred appointment timing. The medical specialty filter allows the patient to filter the available appointments for providers with a given medical specialty. When selected, the patient will only be shown providers that have the credentials for that specialty. For example, if a patient is searching for an appointment with a cardiologist they would select cardiologist and the system would generate a list of cardiologists to schedule an appointment with. In an example, the search feature can access profiles for each provider including their education and professional history.

In one example, the medical need filter allows patients to filter the available appointments by matching explaining their medical need or condition. When the patient doesn't know the appropriate medical specialty, keywords paired with the medical specialties are provided. For example, by selecting the keyword "ear," further questions are suggested to narrow down the appropriate medical specialist between an ENT, audiologist, or general practitioner if the system determines that the ear issue is related to a sinus infection. If the patient's insurance allows for seeing specialists without referrals, the available appointments will reflect a list of ENT's to schedule an appointment with. An option for selecting the provider regardless of insurance coverage is also available. Any private information that is input by the patient will be protected under HIPAA regulations accordingly.

In one example, the provider's name feature allows patients to schedule an appointment with a specific provider. For example, the patient is either referred to a specific provider or knows the name of the provider they wish to see. Typing the provider name in will generate matching provider names that can be then selected and an appointment can then be scheduled.

In one example, the shortest wait feature allows patients to search for an appointment based on which provider is available the soonest. In another example, the shortest wait feature allows patients to search for an appointment based on which provider has the shortest wait time for an appointment the day of the search. In another example, the shortest wait feature allows patients to search for an appointment based on archived appointment timing 2100 data for the wait time previous patient's experience.

In one example, the provider gender feature allows the patient to select if they have a preference for a male or female provider or no preference. From this selection the schedule algorithm generates a list of providers accordingly and an appointment can be scheduled.

In one example, the provider language feature allows the patient to select a specific language they wish for the provider to speak. For example, if the patient needs a Vietnamese speaking provider here is where they would specify Vietnamese speaking, then schedule algorithm will generate a list of Vietnamese speaking providers and an appointment can be scheduled. According to one embodiment, a language translator can be considered either as a provider or as a procedure resource 3000 where their timing needs to be coordinated along with the provider to provide a service to the patient.

In one example, the payment type feature allows the patient to see providers that accept their insurance and those that only take cash. The providers that only take cash can be cheaper because they can make a larger profit off of a cash only transaction.

In one example, the specified appointment timing feature allows the patient to see available appointments for a specified date/time. For example, the patient knows they will be free on a specific date at a specific time and wants to know which providers are available then. Based on the specific date and time, the schedule algorithm will generate a list of providers that are available at that date and time.

The list feature displays the available appointments as list ordered by the soonest available appointment. The list feature allows the patient to actually schedule an appointment with a provider through the scheduling system 1000. An appointment is then added to the patient's list/screen and the day of the appointment the restack indicator keeps track of the more accurate appointment time. Once a patient hits the plus sign to schedule the appointment the provider is sent a request to confirm the appointment.

According to an example, the menu feature includes a 'my account' section, a 'my insurance' section, and a 'my prescriptions' section.

In the 'my account' section there may be a creating an account sub-section that will ask the patient to take a picture of their ID, Insurance card, and method of payment. In one example, this information is used for accuracy, success, and efficiency of the scheduling system 1000. The scanned ID and Insurance is sent to the provider on the day of the patient's appointment. The benefit of the advanced delivery of the patient information is a reduced number of pre-appointment tasks resulting in less waiting time. The payment method is stored with a patient's account in order to automate payment of provider fees so at completion of any appointments scheduled through the scheduling system 1000 the provider receives payment. A benefit here is one less step for the patient to complete at the end of their appointment and also ensures payment to the provider.

Another benefit is the ability to only match appointments with providers accepting the patient's health insurance. In another example, the payment on both the provider's and the patient's behalf can be offered as a service. Benefits of this service include de-risking payment for services through guaranteed payment and a promise to pay the deductible. In addition, allowing the scheduling system 1000 to process the payment allows for efficient submission of a claim to the insurance company.

In the 'my insurance' section the patient's insurance information is stored. This feature can list the insurance benefits the patient receives through their health insurance as well as identify all family members that are covered. In an example, the 'my insurance' section can also automatically determine the co-pay under the patient's health insurance policy in accordance with the provider's charge fee. In an example, a set of contract terms can be sent between the provider and the patient for a promise to pay by the scheduling system 1000. In one case, this will allow the scheduling system 1000 to have a collective bargaining agreement.

The 'my prescriptions' section feature allows patients to have their prescriptions directly sent to their preferred pharmacy or the nearest pharmacy. This feature also keeps a tally of the patient's prescriptions over time. In one case, this feature can generate warnings when the two or more prescriptions should not be taken at the same time. This is a safety feature to prevent the patient from taking prescriptions that should not be mixed.

According to an example, the appointment survey feature includes quantitative and qualitative questions regarding the appointment. The appointment survey can include questions such as remarking on the waiting time before and during the appointment, as well as their experiences with the one or more providers. This data regarding the patient's perception can be used to perform analytics on different methods for assessing the patient's experience.

FIG. 19

FIG. 19 shows an embodiment of a data structure in the scheduling system 1000. In this example, as indicated by matrices, each element in the matrix can include a value or another matrix. For example, a first element in Equation 1 is given by Equation (2) having more than one component. As shown in this example, in this embodiment the set of prediction values 1140 corresponding with each appointment entry component 2000 are in a parallel matrix to an ordered list matrix.

FIG. 20

Figure 20:
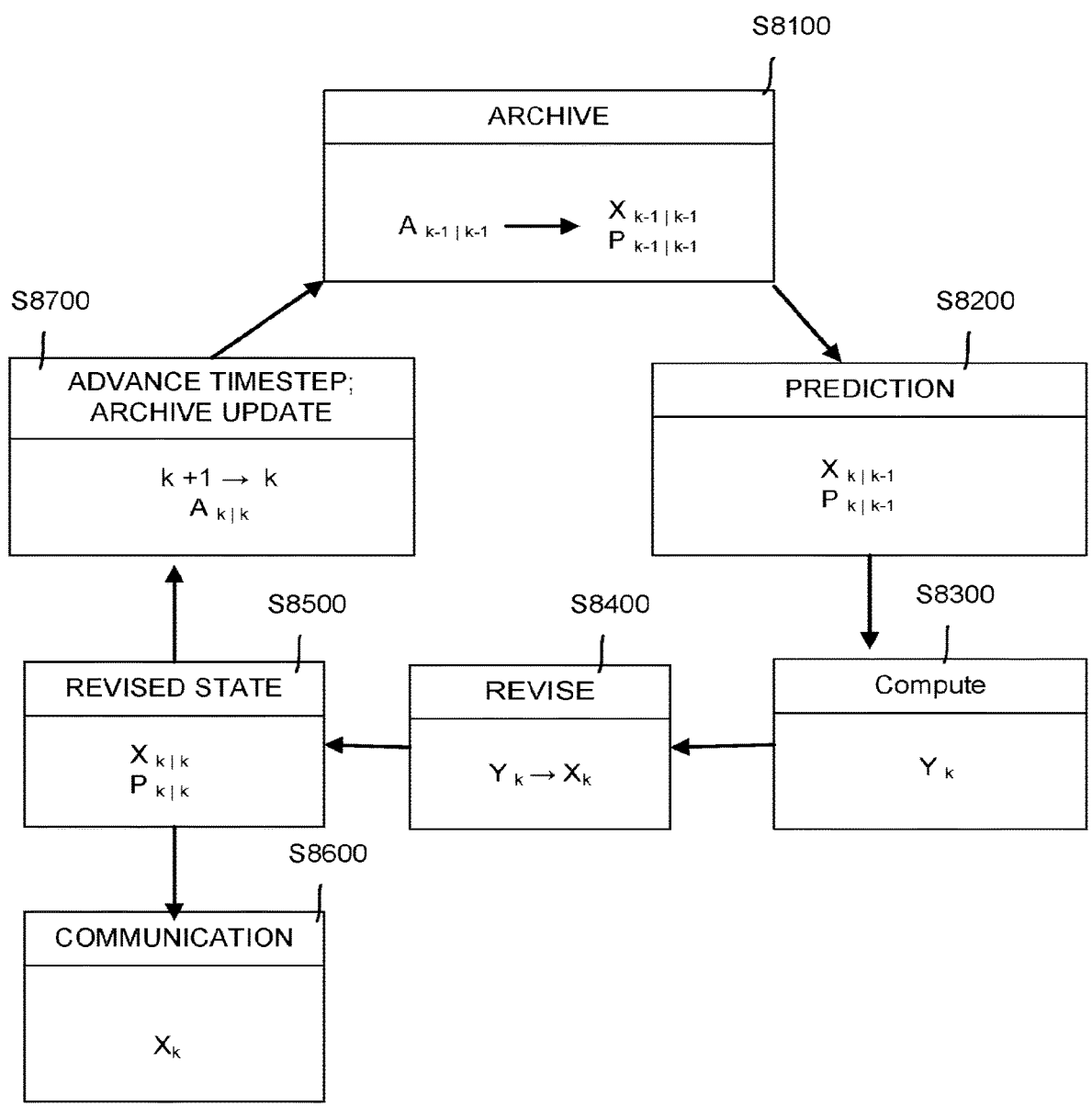
FIG. 20 shows the method shown in FIG. 4A shown as a set of data structures using one or more matrices for each data structure according to an example.

FIG. 20 shows an example to the method S4000 described above shown as a set of data structures using one or more matrices for each data structure where 'k' reflects the current time or state in a series of timesteps or states. At step S8100, the archived timing is used to generate a new appointment entry with the set of PADs and a corresponding set of prediction values. At step S8200, the accumulation of the PADs is used to generate the estimated appointment time for each appointment. At step S8300, the sensor system 1300 senses an actual timestamp associated with the appointment entry. At step S8400, one or more of the PAD's are updated in the ordered list 1110. At step S8500, the ordered list 1110 and the corresponding set of prediction values are updated. At step S8600, the communication is sent to the affected patients. At step S8700, the archived data is updated and the timestep or state is advanced.

FIGS. 21A-21C

Figure 21A:
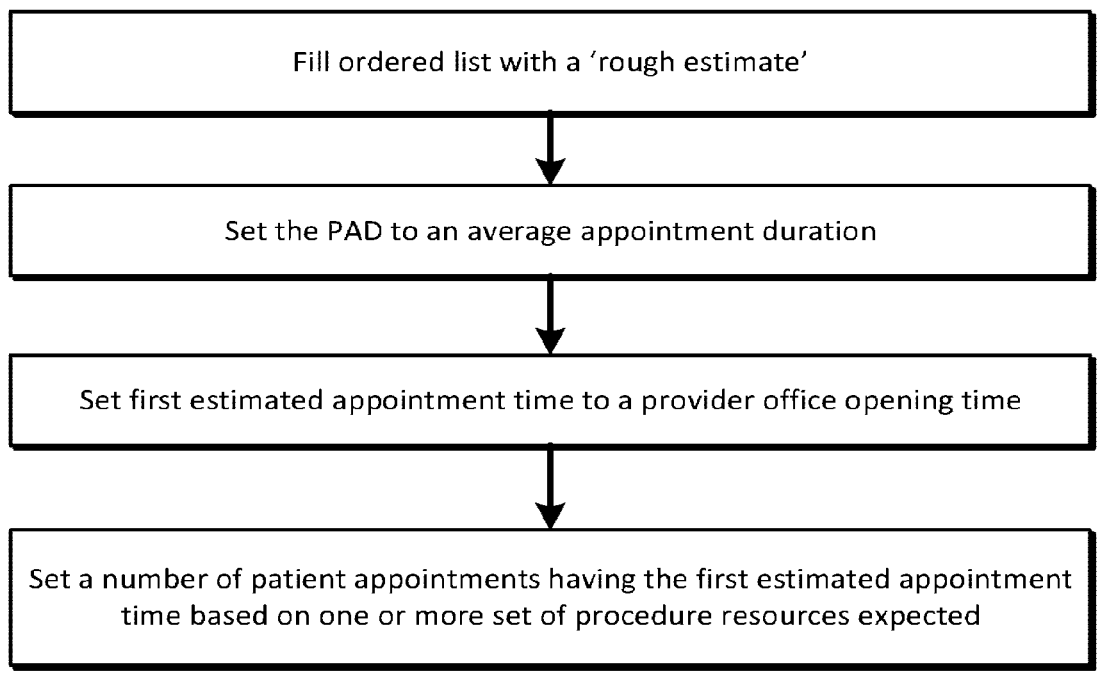
FIG. 21A shows a flow chart of a method for initialization of a new (future) day when an appointment type or medical need is unknown according to an example.
Figure 21B:
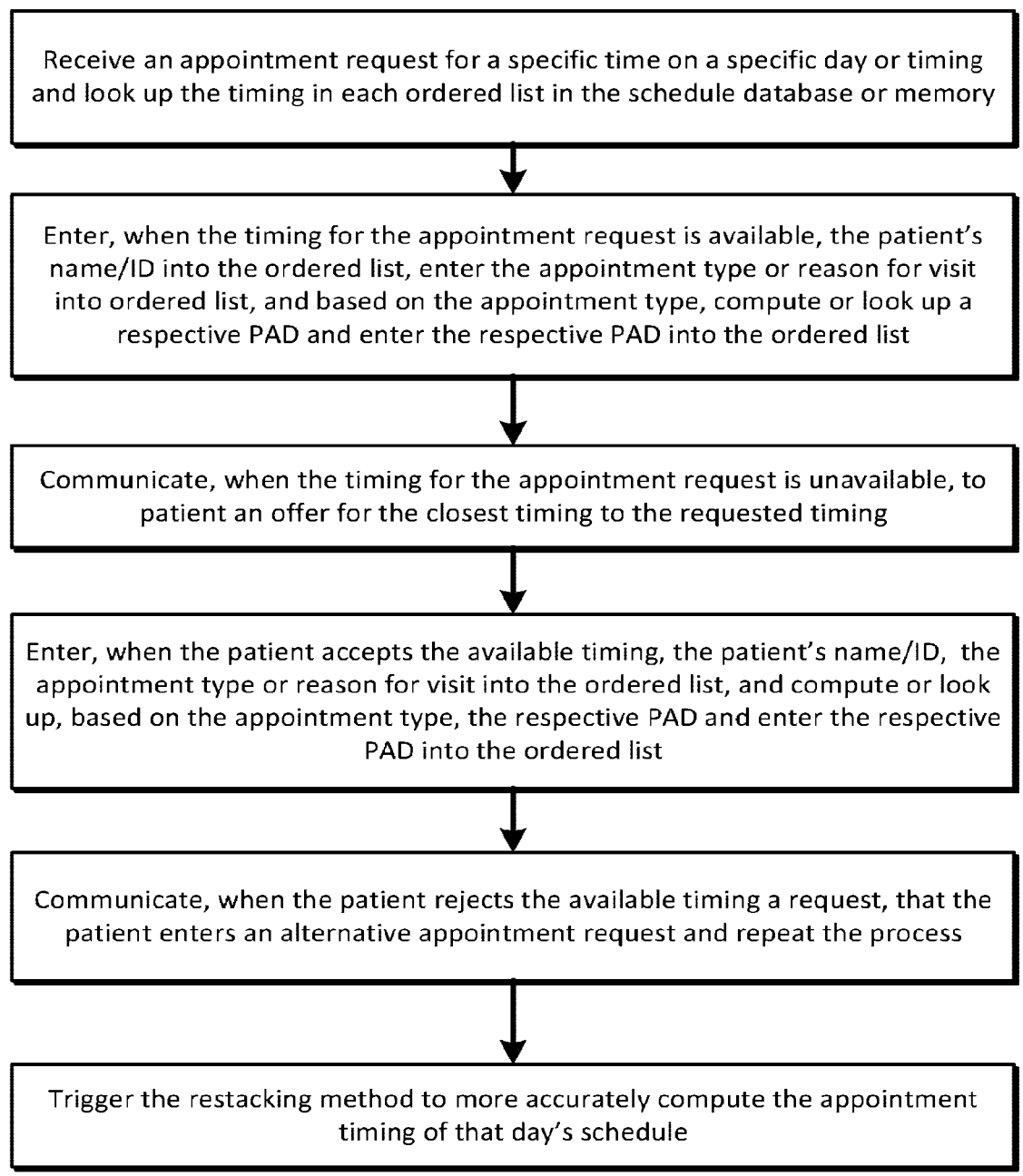
FIG. 21B shows a flow chart of a method for initialization of a new (future) day when the appointment type becomes known according to an example.
Figure 21C:
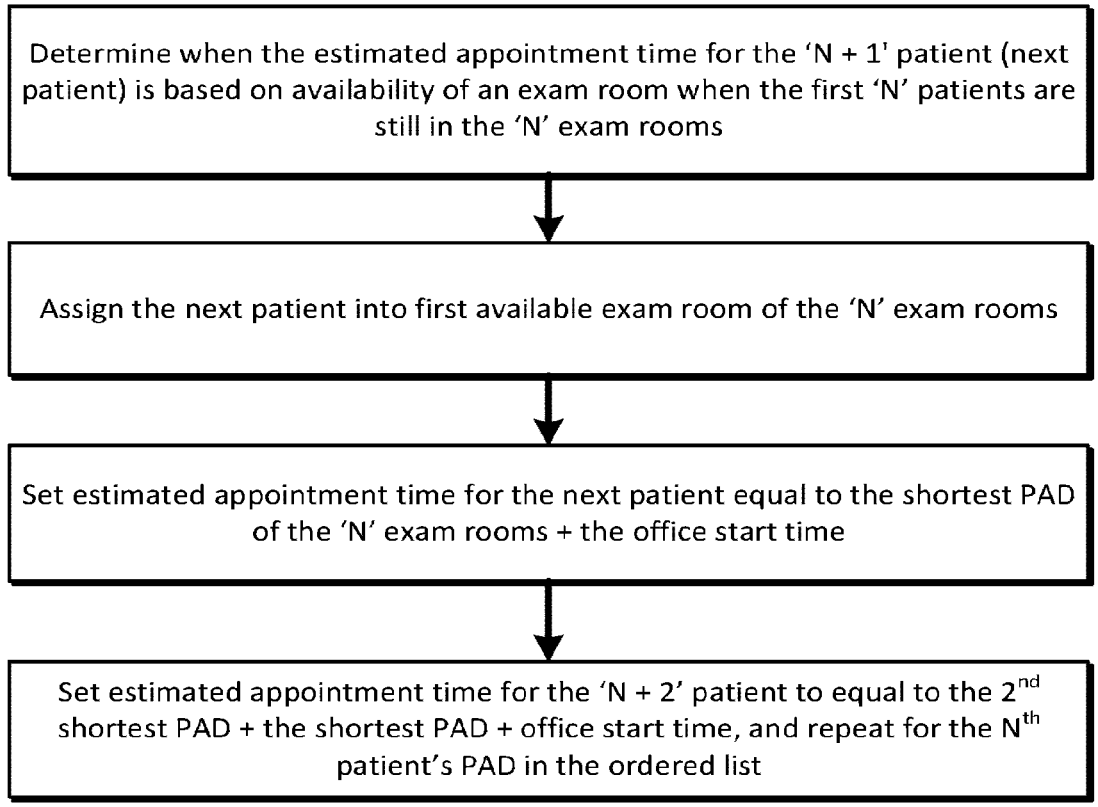
FIG. 21C shows a flow chart of a method for beginning of day handling with availability of 'N' exam rooms according to an example.

FIGS. 21A-21C show examples of methods for initialization of a new appointment for a future day with different steps based on when the appointment type is known or unknown. FIG. 21A shows a flow chart of a method for initialization of a new (future) day when an appointment type or medical need is unknown according to an example. FIG. 21B shows a flow chart of a method for initialization of a new (future) day when the appointment type becomes known according to an example. FIG. 21C shows a flow chart of a method for beginning of day handling with availability of 'N' exam rooms according to an example.

One or more ordered lists 1110 or schedule databases 1100 can be arranged or accessed by one or more future days. Each future day can contain a list of available appointment entries associated will null names, as well as an available appointment duration for each available appointment entry, where the available appointment duration is either assumed or estimated based upon prior days actual duration. Each future day can begin with 'm' number of patient appointment entries, where each patient appointment entry duration is based on a 'filler' duration which may be computed from overall prior average durations of prior appointments, or may be manually entered and is based on human experience. When the appointment type becomes known, the filler duration is replaced with a predicted duration based on the appointment type, the medical need, the one or more appointment states, and/or the actuarial data. The filler duration can be modified to improve each predicted duration.

Prior to each actual duration becoming known, its corresponding predicted duration is predicted. The prediction of each PAD can be done according to several scenarios. The archive 1600 can store a formula that predicts the PAD based on any prior appointment duration and correlation of each prior appointment duration to other factors such as: duration of that patient's prior appointment duration, seniority or age of the patient, time of day, the provider name, the office or facilities, a reason for visit, new/existing patient, seasonal trends, and any daily trends.

Once each actual duration becomes known it can be used to: trigger the scheduling system 1000 to execute the restacking method for the remaining appointments for that day; define whether the appointment is on time or running late; determine when a patient enters or exits the provider office or the exam room; and better predict the PAD of future appointments for that patient.

Turning to FIG. 21A, when the appointment type or the medical need is unknown, the appointment entry can be entered into the ordered list with a 'rough estimate' by setting the PAD to an average appointment duration. The PAD for the average appointment duration can be adjusted due to seasonality or anticipated change in staff or the procedure resources expected. The estimated appointment time can be set as the provider office opening time. The number of patient appointments having the first estimated appointment time can be based on the one or more set of procedure resources expected, such as the number of exam rooms 'N'.

Turning to FIG. 21B, here is an example of the process for handling a patient appointment request for a specific time on a specific day or timing when the appointment type is included. First, look up the timing in each ordered list in the schedule database or memory for availability. When the timing for the appointment request is available, the patient's name/ID, the appointment type or reason for visit, and based on the appointment type, the computed or looked up respective PAD can be entered into the ordered list 1110. When the timing for the appointment request is unavailable, communicate to patient an offer for the closest timing to the requested timing.

When the patient accepts the available appointment timing, the patient's name/ID, the appointment type or reason for visit, and based on the appointment type, the computed or looked up respective PAD can be entered into the ordered list 1110. When the patient rejects the available appointment timing, a communication request that the patient enters an alternative appointment request can be sent and the process can be repeated. Since the initial 'rough estimate' PAD has been replaced by a more accurate PAD and the appointment type or "reason for visit" is now known, trigger the restacking method to more accurately compute the appointment timing of that day's schedule.

The process above was shown with scheduling the appointment timing for the appointments based on the availability of only one procedure resource 3000, the set of exam rooms. According to another example, there can be one or more procedure resources 3000 used to determine the availability of appointment timing to meet the patient appointment request.

Turning to FIG. 21C, at the start of the day, the respective first set of patients are transferred to their respective exam room. In one case, the estimated appointment time for the 'N+1' patient or next patient can be based on availability of an exam room after the first 'N' patients are still in the 'N' exam rooms. Similar to the bubble-up method, the next patient can be called into an exam room as soon as any of the 'N' exam rooms become available. Here, the estimated appointment time for the next patient will equal the shortest PAD of the 'N' exam rooms+the intended office start time. Next, sequentially a cumulative time for all remaining appointments are summed and changes to the appointment timing 2100 of the subsequent patient appointment is calculated. For example, the estimated appointment time for the 'N+2' patient is equal to the 2nd shortest PAD+the shortest PAD+office start time, and so on to the Nth patient's PAD in the ordered list. Once one of these patient appointments is completed, the patient state 2210 is changed to "checked out", the next patient is called into the exam room, and the restack process is performed on the ordered list by using the updated PAD for each patient.

The revised appointment timing 2100 is then communicated to the affected patient for all remaining patients. In one example the communication occurs when the change in timing exceeds the threshold 1470. In another example, performing the restack process includes the step of contacting the one or more patients via phone, email, phone app, text, voice robot caller and communicating the revised appointment timing 2100, and optionally receiving a patient response to accept, reject, or modify the revised appointment timing 2100.

Schedule Forecasting on the Day of Schedule

The system includes elements to improve schedule forecasting on the day of a scheduled appointment, the elements include several components: (i) An ordered schedule of appointments each having an appointment type 1133, an appointment time where each appointment time has an appointment duration that is highly variable and can include a quantity of sub-elements each with a variable time component; (ii) An initial estimation of the appointment duration based on the actuarial data of the appointment type 1133; (iii) A summer to sum the appointment durations and yielding an estimated start time for each appointment; (iv) An ordered list to store the estimated start time associated with the patient scheduled; (v) A notifier on the day of the scheduled appointment for each patient on the ordered list, initially called to the exam room(s) in the estimated start time; (vi) A timer combined with a sensor to start and stop the timer, to measure actual duration of the scheduled appointment; (vii) A bubble-up handler of 1-N exam rooms, measuring occupancy of each exam room by at least one of patient, nurse, administrative staff, provider and upon completion of examination stopping timer using sensor.

A process to improve schedule forecasting on the day of a scheduled appointment, includes the steps of: (i) Updating the initial duration estimate by replacing the estimate with the time duration measure on the timer; (ii) Summing the durations yielding improved forecast or subsequently scheduled appointments; (iii) notifying at least one of the remaining patients scheduled on that same day of the improved forecast of scheduler. This process results in a more accurate estimation of the highly variable duration appointment time by resolving timing variability on the day of the scheduled appointment.

In another example, the process to improve schedule forecasting on the day of a scheduled appointment can include an appointment time waiting room re-stacking algorithm using a bubble up handler of the exam room status such that a longer appointment state duration or unpredictable appointment durations are pushed-down/demoted and predictable or lower appointment durations are pushed up/promoted such that the lightest element represents an exam room that is either recently vacated or about to become vacated. In this case, each exam room has one or more exam room states including at least one of waiting for nurse, waiting for provider, waiting for equipment, waiting for medication, meeting nurse, meeting provider. The total number of exam room states can be variable and depend on the appointment type 1133 or number of appointment states and a respective duration for each exam room state is accordingly set.

Obviously, numerous modifications and variations of the present disclosure are possible in light of the above teachings. Further embodiments have been envisioned including features for repeating appointments based on fixed time interval (i.e. checkup every 3 months), use of machine learning or artificial intelligence to improve the PAD estimate and restacking method, creating virtual tours of the doctor's office that are visible through the patient device, incorporating a messaging platform that can expand to allow for remote diagnosis via photo/video HIPAA compliant communication between patients and practitioners, as well as a rating/score for providers (whether publicly visible or not) so that certain providers can be ranked higher or receive specific endorsements from the scheduling system based on their performance. It is therefore to be understood that within the scope of the appended claims, the invention may be practiced otherwise than as specifically described herein.

The invention claimed is:

1. A system for reduction of patient waiting times at a medical provider site, comprising:
 a scheduling server located across a first connection to the Internet from a healthcare provider and configured to schedule patient appointments at the medical provider site; and
 a sensor and communication system comprising plural sensing devices, each having different spatial accuracy factors representing different spatial precisions and temporal accuracies between the plural sensing devices and each networked in communication with the scheduling server via the first connection to the Internet, the sensing devices comprising at least
1) a mobile patient device located with a patient,
2) At least one provider device operated located at the medical provider site, and
3) a first medical records database at the medical provider site, wherein the scheduling server a) communicates across a second connection to the Internet to query a second medical records database to obtain Health Insurance Portability and Accountability (HIPAA) compliant confidential patient data including prior patient medical information (PPMI) of third party patients, and b) divides the patient appointments at the medical provider site into respective appointment states, the respective states including at least a patient check-in state, a provider examination state, and a patient appointment complete state, wherein the sensing devices sense patient availability at start times for at least one of the respective appointment states using available outputs indicating a proximity-time of the patient at the respective appointment states, wherein the scheduling server is configured to:
a) based on the PPMI of the third party patients, determine respective predicted durations for each of the respective states,
b) based on the spatial accuracy factors representing the different spatial precisions and temporal accuracies, select from the available outputs from the sensing devices an output from the sensing device having a highest precision for the proximity-time of the patient, and determine respective actual durations at each of the respective states from the output from the sensing device having the highest precision for the proximity-time of the patient, and
c) update future predicted appointment times and durations for other patients based on the determined respective actual durations at each of the respective states,
d) predict future patient appointments whereby the patient waiting times at the medical provider site are reduced.

2. The system of claim 1, wherein
the provider device comprises a graphical interface between the provider and the scheduling server,
the graphical interface including a pop-out showing details of a patient appointment time including an original appointment time and an actual clock time, and
the pop-out having a delay icon configured to send delay message to the patient.

3. The system of claim 2, wherein the graphical interface is configured to display available resources including rooms at the provider site along with appointments scheduled in the rooms.

4. The system of claim 1, wherein the scheduling server is configured to, after an appointment state of the respective appointment states is completed, replace a predicted timing for the appointment state with an actual timing.

5. The system of claim 1, wherein the scheduling server is configured to predict timings for remaining schedules at the medical provider site using an actual timestamp provided by one of the sensing devices.

6. The system of claim 1, wherein the respective appointment states include at least one of taking a patient vital and performing a patient procedure.

7. The system of claim 1, wherein
the scheduling server is further configured to receive a message regarding the patient arriving at the medical provider, and send a pop-up message to the medical provider of patient arrival.

8. The system of claim 1, wherein the scheduling server is configured to perform a statistical analysis on the first medical records database in order to predict future visit durations.

9. The system of claim 1, wherein the scheduling server is configured to send encrypted push-pull communications to and from the second medical records database.

10. The system of claim 1, wherein the scheduling server is configured to identify patient appointment locations including one or more of patient waiting rooms, lab rooms, examination rooms, procedure rooms.

11. The system of claim 1, wherein the scheduling server is configured to account for medical personnel and determine medical resource availability in determining patient scheduling.

12. The system of claim 1, wherein the sensor and communication system provides to the scheduling server proximity-time data associated with progression of the respective states of the patient, the proximity-time data including a patient location and a timestamp.

13. The system of claim 1, wherein the scheduling server is configured to send notifications to the mobile patient device of schedule changes in the patient appointments and to receive acceptance of appointment timing from an affected patient having a schedule change.

14. The system of claim 1, wherein the scheduling server is configured to predict durations and delays in the patient appointments.

15. The system of claim 1, wherein
the scheduling server is further configured to assign an initial prediction value of a new appointment entry to a respective prediction value in an archive having a matching associated appointment entry,
the scheduling server is further configured to assign the initial prediction value based on a threshold, and
the threshold is one of a spatial distance and a timing criteria.

16. The system of claim 1, wherein the scheduling server is further configured to a) rank each sensor system communication by a respective spatial accuracy factor, and b) select a highest ranked sensor system communication for further processing.

17. The system of claim 1, wherein the respective appointment states includes a patient-vitals-taken state.

* * * * *